(12) United States Patent
Loose et al.

(10) Patent No.: US 11,160,868 B2
(45) Date of Patent: *Nov. 2, 2021

(54) THERMOREVERSIBLE COMPOSITIONS FOR ADMINISTRATION OF THERAPEUTIC AGENTS

(71) Applicant: Frequency Therapeutics, Inc., Woburn, MA (US)

(72) Inventors: Christopher Loose, Winchester, MA (US); Will McLean, North Haven, CT (US); Megan Harrison, Middletown, CT (US); Michael R. Jirousek, Chardon, OH (US)

(73) Assignee: Frequency Therapeutics, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/239,786

(22) Filed: Jan. 4, 2019

(65) Prior Publication Data

US 2019/0231880 A1    Aug. 1, 2019

Related U.S. Application Data

(62) Division of application No. 15/447,682, filed on Mar. 2, 2017, now Pat. No. 10,213,511.

(60) Provisional application No. 62/302,747, filed on Mar. 2, 2016.

(51) Int. Cl.
| | | |
|---|---|---|
| *A61K 47/34* | (2017.01) | |
| *A61K 47/12* | (2006.01) | |
| *A61K 31/506* | (2006.01) | |
| *A61K 31/4439* | (2006.01) | |
| *A61K 31/551* | (2006.01) | |
| *A61K 9/00* | (2006.01) | |

(52) U.S. Cl.
CPC .......... *A61K 47/34* (2013.01); *A61K 9/0019* (2013.01); *A61K 31/4439* (2013.01); *A61K 31/506* (2013.01); *A61K 31/551* (2013.01); *A61K 47/12* (2013.01)

(58) Field of Classification Search
CPC .......................... A61K 31/4439; A61K 31/506
USPC ....................................................... 514/275
See application file for complete search history.

(56) References Cited

U.S. PATENT DOCUMENTS

| | | |
|---|---|---|
| 5,059,591 A | 10/1991 | Janoff et al. |
| 5,421,818 A | 6/1995 | Arenberg |
| 5,474,529 A | 12/1995 | Arenberg |
| 5,476,446 A | 12/1995 | Arenberg |
| 5,731,144 A | 3/1998 | Toothman et al. |
| 5,731,424 A | 3/1998 | Toothman et al. |
| 5,837,681 A | 11/1998 | Magal |
| 6,045,528 A | 4/2000 | Arenberg |
| 6,124,449 A | 6/2000 | Gold et al. |
| 6,090,383 A | 7/2000 | Dasch et al. |
| 6,177,434 B1 | 1/2001 | Kopke et al. |
| 6,419,928 B1 | 7/2002 | Dasch et al. |
| 6,476,031 B1 | 11/2002 | Chakravarty et al. |
| 6,509,318 B1 | 1/2003 | Bhatnagar et al. |
| 6,593,290 B1 | 7/2003 | Gao |
| 6,943,191 B1 | 9/2005 | Narayanan et al. |
| 7,030,125 B2 | 4/2006 | Munchhof et al. |
| 7,087,626 B2 | 8/2006 | Beight et al. |
| 7,151,169 B2 | 12/2006 | Thompson et al. |
| 7,223,766 B2 | 5/2007 | Dugar et al. |
| 7,387,614 B2 | 6/2008 | Staecker |
| 7,498,031 B2 | 3/2009 | Fujioka et al. |
| 7,514,445 B2 | 4/2009 | Freyne et al. |
| 7,723,486 B2 | 5/2010 | Ledbetter et al. |
| 7,915,280 B2 | 3/2011 | Ferraris et al. |
| 8,071,591 B2 | 12/2011 | Nomura et al. |
| 8,207,216 B2 | 6/2012 | Kozikowski et al. |
| 8,298,825 B1 | 10/2012 | Hochedlinger et al. |
| 8,377,886 B2 | 2/2013 | Susztak et al. |
| 8,575,122 B2 | 11/2013 | Lichter et al. |
| 8,686,042 B2 | 4/2014 | Gil et al. |
| 8,709,385 B2 | 4/2014 | Tamarkin et al. |
| 8,771,754 B2 | 7/2014 | Hallahan |
| 8,784,870 B2 | 7/2014 | Lichter et al. |
| 8,852,626 B2 | 10/2014 | Lichter et al. |
| 9,333,171 B2 | 5/2016 | Lichter et al. |
| 9,347,042 B2 | 5/2016 | Shimmura et al. |
| 9,913,835 B2 | 3/2018 | Loose et al. |
| 9,913,848 B2 | 3/2018 | Loose et al. |
| 9,968,615 B2 | 5/2018 | Loose et al. |
| 10,016,507 B2* | 7/2018 | Loose .................... A61K 31/19 |

(Continued)

FOREIGN PATENT DOCUMENTS

| | | |
|---|---|---|
| CA | 2268331 | 5/1998 |
| CN | 1319968 | 6/2007 |

(Continued)

OTHER PUBLICATIONS

Almeida H. et al., "In situ gelling systems: a strategy to improve the bioavailability of ophthalmic pharmaceutical compositions", *Drug Discovery Today* 2014, vol. 19, No. 4, p. 400-412.

Bohl A. et al. "Development of a specially tailored local drug delivery system for the prevention of fibrosis after insertion of cochlear implants into the inner ear" Journal of *Materials Science: Materials in Medicine* 2012, vol. 23, p. 2151-62,.

(Continued)

*Primary Examiner* — Kevin E Weddington

(74) *Attorney, Agent, or Firm* — Cooley LLP

(57) ABSTRACT

The present invention relates to compositions and methods of inducing the self-renewal of stem/progenitor supporting cells, including inducing the stem/progenitor cells to proliferate while maintaining, in the daughter cells, the capacity to differentiate into hair cells.

18 Claims, 2 Drawing Sheets

(56) References Cited

U.S. PATENT DOCUMENTS

| | | |
|---|---|---|
| 10,041,046 B2 | 8/2018 | Karp et al. |
| 10,041,047 B2 | 8/2018 | Karp et al. |
| 10,201,540 B2 | 2/2019 | Loose et al. |
| 10,213,511 B2 | 2/2019 | Loose et al. |
| 10,220,041 B2 | 3/2019 | Loose et al. |
| 10,568,883 B2 | 2/2020 | Karp et al. |
| 10,954,490 B2 | 3/2021 | Karp et al. |
| 11,033,546 B2 | 6/2021 | Loose et al. |
| 2003/0028905 A1 | 2/2003 | Knaus et al. |
| 2004/0006030 A1 | 1/2004 | Monia et al. |
| 2004/0015781 A1 | 1/2004 | Brown et al. |
| 2004/0038856 A1 | 2/2004 | Chakravarty et al. |
| 2004/0138188 A1 | 7/2004 | Higgins et al. |
| 2004/0147574 A1 | 7/2004 | Munchhof |
| 2004/0204431 A1 | 10/2004 | Scarborough et al. |
| 2005/0032835 A1 | 2/2005 | Pandey et al. |
| 2005/0227936 A1 | 10/2005 | McSwiggen et al. |
| 2005/0245508 A1 | 11/2005 | Weller et al. |
| 2005/0245520 A1 | 11/2005 | Dodic et al. |
| 2005/0287127 A1 | 12/2005 | Li et al. |
| 2005/0287128 A1 | 12/2005 | Guerciolini et al. |
| 2006/0003929 A1 | 1/2006 | Bier et al. |
| 2006/0229266 A1 | 10/2006 | Kumar et al. |
| 2007/0066632 A1 | 3/2007 | Hart et al. |
| 2007/0088080 A1 | 4/2007 | Gordillo et al. |
| 2007/0155722 A1 | 7/2007 | Li et al. |
| 2007/0167918 A1 | 7/2007 | Reed et al. |
| 2008/0015161 A1 | 1/2008 | Vornlocher et al. |
| 2008/0108656 A1 | 5/2008 | Pandey et al. |
| 2009/0006043 A1 | 1/2009 | Petersik et al. |
| 2009/0036382 A1 | 2/2009 | Bressan et al. |
| 2009/0270497 A1 | 10/2009 | Buggy |
| 2009/0325938 A1 | 12/2009 | Lichter et al. |
| 2010/0267141 A1 | 10/2010 | Shi |
| 2010/0292205 A1 | 11/2010 | Lefker et al. |
| 2011/0135756 A1 | 6/2011 | Owens et al. |
| 2011/0166060 A1 | 7/2011 | Simons et al. |
| 2011/0250274 A1 | 10/2011 | Shaked et al. |
| 2011/0305674 A1 | 12/2011 | Edge et al. |
| 2012/0059021 A1 | 3/2012 | Biechele |
| 2012/0196312 A1 | 8/2012 | Sato et al. |
| 2012/0277199 A1 | 11/2012 | Ye et al. |
| 2013/0079329 A1 | 3/2013 | Hood |
| 2013/0189327 A1 | 7/2013 | Ortega et al. |
| 2013/0280177 A1 | 10/2013 | Raman et al. |
| 2013/0324594 A1 | 12/2013 | Guthrie |
| 2014/0243227 A1 | 8/2014 | Clevers et al. |
| 2014/0248696 A1 | 9/2014 | Zhang et al. |
| 2015/0025096 A1 | 1/2015 | Thies et al. |
| 2015/0240212 A1 | 8/2015 | Peterson et al. |
| 2015/0329821 A1 | 11/2015 | Ang et al. |
| 2016/0032240 A1 | 2/2016 | Heller et al. |
| 2016/0194604 A1 | 7/2016 | Karp et al. |
| 2017/0000728 A1 | 1/2017 | Lichter et al. |
| 2017/0071937 A1 | 3/2017 | Karp et al. |
| 2017/0226477 A1 | 8/2017 | Karp et al. |
| 2017/0252340 A1 | 9/2017 | Loose et al. |
| 2017/0252448 A1 | 9/2017 | Loose et al. |
| 2017/0252449 A1 | 9/2017 | Loose et al. |
| 2017/0252450 A1 | 9/2017 | Loose et al. |
| 2017/0349884 A1 | 12/2017 | Karp et al. |
| 2018/0214458 A1 | 8/2018 | Loose et al. |
| 2018/0256590 A1 | 9/2018 | Loose et al. |
| 2019/0017015 A1 | 1/2019 | Karp et al. |
| 2019/0060371 A1 | 2/2019 | McLean |
| 2019/0093079 A1 | 3/2019 | Loose et al. |
| 2019/0201398 A1 | 7/2019 | Loose et al. |
| 2019/0350845 A1 | 11/2019 | Lichter et al. |
| 2020/0323853 A1 | 10/2020 | Karp et al. |
| 2021/0093635 A1 | 4/2021 | Loose et al. |

FOREIGN PATENT DOCUMENTS

| | | | |
|---|---|---|---|
| CN | 101341138 | 11/2012 | |
| CN | 103169649 | 6/2013 | |
| CN | 103361300 | 10/2013 | |
| EP | 0945464 | 9/1999 | |
| EP | 1739087 | 1/2007 | |
| EP | 1961748 | 8/2008 | |
| EP | 2636731 | 9/2013 | |
| EP | 2765188 | 8/2014 | |
| JP | 2012148995 | 8/2012 | |
| WO | WO-1996/040094 | 12/1996 | |
| WO | WO-1998/019700 | 5/1998 | |
| WO | WO-1999/058128 | 11/1999 | |
| WO | WO-2000/012497 | 3/2000 | |
| WO | WO-2000/031135 | 6/2000 | |
| WO | WO-2000/059939 | 10/2000 | |
| WO | WO-2001/085685 | 11/2001 | |
| WO | WO-2002/094833 | 11/2002 | |
| WO | WO-2003/037891 | 5/2003 | |
| WO | WO-2003/097639 | 11/2003 | |
| WO | WO-2004/013135 | 2/2004 | |
| WO | WO-2004/021989 | 3/2004 | |
| WO | WO-2004/026307 | 4/2004 | |
| WO | WO-2004/026865 | 4/2004 | |
| WO | WO-2004/026871 | 4/2004 | |
| WO | WO-2004/067530 | 8/2004 | |
| WO | WO-2005/009939 | 2/2005 | |
| WO | WO-2005/039570 | 5/2005 | |
| WO | WO-2006/018633 | 2/2006 | |
| WO | WO-2006/018967 | 2/2006 | |
| WO | WO-2006/1 00490 | 9/2006 | |
| WO | WO-2007/018818 | 2/2007 | |
| WO | WO-2007/048857 | 5/2007 | |
| WO | WO-2007/102770 | 9/2007 | |
| WO | WO-2008/010852 | 1/2008 | |
| WO | WO 2008/076556 A2 | 6/2008 | |
| WO | WO-2008/077138 | 6/2008 | |
| WO | WO-2009/009737 | 1/2009 | |
| WO | WO-2009006043 A2 * | 1/2009 | ......... A61K 31/5517 |
| WO | WO-2009/017453 | 2/2009 | |
| WO | WO-2009/017455 | 2/2009 | |
| WO | WO-2009/032667 | 3/2009 | |
| WO | WO-2009/132050 | 10/2009 | |
| WO | WO 2010/060088 A2 | 5/2010 | |
| WO | WO-2010/068955 | 6/2010 | |
| WO | WO-2010/075551 | 7/2010 | |
| WO | WO-2010/104205 | 9/2010 | |
| WO | WO-2011/019957 | 2/2011 | |
| WO | WO-2011/050476 | 5/2011 | |
| WO | WO-2011/079841 | 7/2011 | |
| WO | WO-2011/089416 | 7/2011 | |
| WO | WO-2011/116930 | 9/2011 | |
| WO | WO-2011/143511 | 11/2011 | |
| WO | WO-2012/018933 | 2/2012 | |
| WO | WO 2012/103012 A1 | 8/2012 | |
| WO | WO-2013/051722 | 4/2013 | |
| WO | WO-2013/124413 | 8/2013 | |
| WO | WO-2014/003098 | 1/2014 | |
| WO | WO-2014/013255 | 1/2014 | |
| WO | WO 2014/039908 A1 | 3/2014 | |
| WO | WO-2014/050779 | 4/2014 | |
| WO | WO-2014/059383 | 4/2014 | |
| WO | WO-2014/083132 | 6/2014 | |
| WO | WO-2014/159356 | 10/2014 | |
| WO | WO 2014/159356 A1 | 10/2014 | |
| WO | WO-2015/038704 A1 | 3/2015 | |
| WO | WO-2015/168149 | 11/2015 | |
| WO | WO-2015/175783 | 11/2015 | |
| WO | WO-2016/037016 | 3/2016 | |
| WO | WO-2017/120543 | 7/2017 | |
| WO | WO-2017/132530 | 8/2017 | |
| WO | WO-2018/125746 | 7/2018 | |
| WO | WO-2020/072601 | 4/2020 | |
| WO | WO-2020/072602 | 4/2020 | |

OTHER PUBLICATIONS

Engleder E. et al. "Preclinical evaluation of thermoreversible triamcinolone acetonide hydrogels for drug delivery to the inner ear" *International Journal of Pharmaceutics* 2014, vol. 471, p. 297-302,.

(56) References Cited

OTHER PUBLICATIONS

Hoskison E. et al., "Drug delivery to the ear" *Therapeutic Delivery* 2013, vol. 4, No. 1, p. 115-124.
Kanzaki S. et al., "Novel In Vivo Imaging Analysis of an Inner Ear Drug Delivery System in Mice: Comparison of Inner Ear Drug Concentrations over Time after Transtympanic and Systemic Injections", *PloS ONE* 2012, vol. 7, Issue 12, p. e48480,.
Kim. D. et al. "Development of a drug delivery system for the inner ear using poly(amino acid)-based nanoparticles", *Drug delivery*, 2015, vol. 22, No. 3, p. 367-374.
Kimmel, A. "Identification and Characterization of Specific Clones: Strategy for Confirming the Validity of Presumptive Clones", *Methods Enzymol.* 1987, vol. 152, p. 507-511.
Lajud S. et al. "A regulated delivery system for inner ear drug application" *Journal of controlled release: official journal of the Controlled Release Society* 2013, vol. 166, p. 268-276.
Li M et al. "A novel aerosol-mediated drug delivery system for inner ear therapy: intratympanic aerosol methylprednisolone can attenuate acoustic trauma" *IEEE Transactions on Biomedical Engineering* 2013, vol. 60, No. 9, p. 2450-2460.
Li, H. et al. "Pluripotent stem cells from the adult mouse inner ear", Nature Medicine, 2003, vol. 9, No. 10, p. 1293-1299.
Liu Q. et al. "Identification of stage-specific markers during differentiation of hair cells from mouse inner ear stem cells or progenitor cells in vitro", *International Journal of Biochemistry & Cell Biology*, 2015, vol. 60, p. 99-111.
Pararas E. et al. "Microsystems technologies for drug delivery to the inner ear", *Advanced drug delivery reviews* 2012, vol. 64, p. 1650-1660.
Pritz C. et al. "Nanomedicine strategies for drug delivery to the ear", *Nanomedicine* 2013, vol. 8, No. 7,p. 1155-1172.
Rivera T. et al. "Drug delivery to the inner ear: strategies and their therapeutic implications for sensorineural hearing loss", *Current Drug Delivery* 2012, vol. 9, p. 231-242.
Roy S. et al. "Strategies for drug delivery to the human inner ear by multifunctional nanoparticles", *Nanomedicine* 2012, vol. 7, No. 1, p. 55-63.
Staecker H. et al., "Developments in delivery of medications for inner ear disease", *Expert Opinion Drug Delivery* 2013, vol. 10, p. 639-650.
Surovtseva E. et al. "Prestin binding peptides as ligands for targeted polymersome mediated drug delivery to outer hair cells in the inner ear", *International Journal of Pharmaceutics* 2012, vol. 424, p. 121-127.
Wahl et al. "Molecular Hybridization of Nucleic Acids", *Methods in Enzymology*, 1987, vol. 152, p. 399-407.
Wise A. et al. "Drug delivery to the inner ear", *Journal of Neural Engineering* 2012, vol. 9, p. 065002.
Ahn et al. (2014). "GSK3?, but not GSK3?, inhibits the neuronal differentiation of neural progenitor cells as a downstream target of mammalian target of rapamycin complex1." Stem cells and development. 23(10): 1121-33.
"Database accession No. NLM25167568. Yeap Li-Ling et al. (2014)." "Valproate-induced reversible sensorineural hearing loss: a case report with serial audiometry and pharmacokinetic modelling during a valproate rechallenge." Epileptic Disorders : International Epilepsy Journal With Videotape Sep. 2014.
Database accession No. PREV199191056930. Armon C. et al. (1990). "Sensorineural Hearing Loss a Reversible Effect of Valproic Acid." vol. 40, No. 12 pp. 1896-1898, ISSN: 0028-3878.
Database accession No. PREV201600270745. Benajiba Lina et al. (2015). "Identification of a First in Class GSK3-Alpha Selective Inhibitor as a New Differentiation Therapy for AML." Blood,vol. 126, No. 23. ISSN: 0006-4971 (print).
Doble et al. (2007). "Functional redundancy of GSK-3alpha and GSK-3beta in Wnt/beta-catenin signaling shown by using an allelic series of embryonic stem cell lines." Developmental Cell, vol. 12, No. 6, p. 957-971.

Kuo et al. (2015). "In Vivo Cochlear Hair Cell Generation and Survival by Coactivation of beta-Catenin and Atohl." Journal of Neuroscience, vol. 35, No. 30, p. 10786-10798.
Lipinski et al. (2001). "Experimental and computational approaches to estimate solubility and permeability in drug discovery and development settings." Advanced Drug Delivery Reviews, p. 3-26.
Nekrassov et al. (2006). "Additive effects of antiepileptic drugs and pentylenetetrazole on hearing." Neuroscience Letters. 406(3): 276-80.
Park et al. (2009). "Selective GSK-3? inhibitors attenuate the cisplatin-induced cytotoxicity of auditory cells." Hearing research. 257(1-2): 53-62.
Roccio et al. (2015). "Cell cycle reactivation of cochlear progenitor cells in neonatal FUCCI mice by a GSK3 small molecule inhibitor." Scientific reports. 5: 17886.
Uno et al. (2009). "Efficacy of a novel, orally active GSK-3 inhibitor 6-Methyl-N-[3-[[3-(1-methylethoxy)propyl]carbamoyl]-1Hpyrazol-4-yl]pyridine-3-carboxamide in tau transgenic mice." Brain research, 1296, pp. 148-163.
Alford et al. (2014). "American College of Medical Genetics and Genomics Guideline for the Clinical Evaluation and Etiologic Diagnosis of Hearing Loss." Genetics in Medicine: Official Journal of the American College of Medical Genetics. vol. 16, pp. 347-355.
Arnold et al. (2011). "Zinc for Attention-Deficit/Hyperactivity Disorder: Placebo-Controlled Double-Blind Pilot Trial Alone and Combined with Amphetamine." Journal of Child and Adolescent Psychopharmacology, vol. 21(1): 1-19.
Associacao Brasileira de Otorrinolaringologia e Cirurgia Cervicofacial et al. (2012). "Sensorineural Hearing Loss: Radiologic Diagnosis." Revista da Associacao Medica Brasileira, vol. 58, pp. 519-529.
Barker et al. (2007). "Identification of stem cells in small intestines and colon by marker gene Lgr5." Nature Publishing Group. vol. 449, No. 25.
Barker et al. (2010). "Lgr5-'-ve stem cells drive self-renewal in the stomach and build long-lived gastric units in vitro." Cell Stem Cell. vol. 6, 25-36.
Bermingham et al. (1999). "Math 1: An Essential Gene for the Generation of Inner Ear Hair Cells." Science, 284: 1837-1841.
Borenstein, J.T. (2011). "Intracochlear Drug Delivery Systems." Expert Opinion on Drug Delivery, vol. 8, No. 9, pp. 1161-1174.
Bramhall et al. (2014). "Lgr5-Positive Supporting Cells Generate New Hair Cells in the Postnatal Cochlea." Stem Cell Reports. 2(3): 311-322.
Brigande et al. (2009). "Quo vadis, hair cell regeneration?" Nat. Neurosci., 12(6): 679-685.
Buczacki et al. (2013). "Intestinal label-retaining cells are secretory precursors expressing Lgr5," Nature, 495: 65-72.
Butler et al. (2010). "Rational Design and Simple Chemistry Yield a Superior, Neuroprotective HDAC Inhibitor, Tubastatin A," J. Am. Chem. Soc., vol. 132: 10842-10846.
Byfield et al. (2004). "Lateral Signaling Enhances TGF-J3 Response Complexity." Trends Cell Biol., 14(3): 107-111.
Byfield et al. (2004). "SB-505124 Is a Selective Inhibitor of Transforming Growth Factor-J3 Type I Receptors ALK4, ALK5, and ALK7." Molecular Pharmacology. Vol. 65, No. 3, pp. 744-752.
Callahan et al. (2002). "Identification of Novel Inhibitors of the Transforming Growth Factor Betal (TGF-betal) Type 1 Receptor (ALK5)." J. Med. Chem., vol. 45., No. 5, pp. 999-1001.
Cao et al. (2014). "Selective small molecule compounds increase BMP-2 responsiveness by inhibiting Smurfl-mediated Smad1/5 degradation." Scientific reports. 4: 4965.
Chai et al. (2011). "Dynamic Expression of Lgr5, a Wnt Target Gene, in the Developing and Mature Mouse Cochlea." J. Assoc. Res. Otolaryngology. 12(4): 455-469.
Chai et al. (2012). "Wnt signaling induces proliferation of sensory precursors in the postnatal mouse cochlea." Proc. Nat'l. Acad. Sci. USA. 109(21): 8167-8172.
Chen et al. (2005). "Inner Ear Drug Delivery Via a Reciprocating Perfusion System in the Guinea Pig," Journal of Controlled Release : Official Journal of the Controlled Release Society, 110: 1-9.

(56) References Cited

OTHER PUBLICATIONS

Chen et al. (2007) "Preliminary Study on Brain-Targeted Drug Delivery Via Inner Ear," Actapharmaceutica Sinica, 42(10): 1102-1106.

Chen et al. (2009). "Aminoglycoside-induced histone deacetylation and hair cell death in the mouse cochlea," J. Neurochem., 108(5): 1226-1236.

Cox et al. (2014). "Spontaneous Hair Cell Regeneration in the Neonatal Mouse Cochlea in Vivo." Development. vol. 141, No. 4, pp. 816-829.

Crosnier et al. (2006). "Organizing cell renewal in the intestine: stem cells, signals and combinatorial control." Nature Reviews Genetics, 7: 349-359.

Dai et al. (2002). "Human Serum and Glucocorticoid-Inducible Kinase-Like Kinase (SGKL) Phosphorylates Glycogen Synthases Kinase 3 Beta (GSK-3beta) at Serine-9 Through Direct Interation." Biolchem. Biophys. Res. Commun., vol. 293, No. 4, pp. 1191-1196.

Davies et al. (2001). "The Interaction Between J3-Catenin, GSK3J3 and APC After Motogen Induced Cell-Cell Dissociation, and Their Involvement in Signal Transduction Pathways in Prostate Cancer." International Journal of Oncology. vol. 18, No. 4, pp. 843-847.

Davis et al. (2008). "Mesodermal Fate Decisions of a Stem Cell: the Wnt Switch," Cell Mol Life Sci., 65(17):2658-74. (abstract only).

Drottar et al. (2006). "The Histone Deacetylase Inhibitor Sodium Butyrate Protects Against Cisplatin-Induced Hearing Loss in Guinea Pigs," Laryngoscope, 116(2): 292-296.

Dumont et al. (2003). "Targeting the TGFJ3 Signaling Network in Hun1an Neoplasia." Cancer Cell. vol. 3, No. 6, pp. 531-536.

Espinoza et al. (2003). "Phosphorylation by Glycogen Synthase Kinase-3J3 Down-Regulates Notch Activity, a Link for Notch and Wnt Pathways." Journal of Biological Chemistry. vol. 278, No. 34, pp. 32227-32235.

Fakhari et al. (2017). "Thermogelling properties of purified poloxamer407." Heliyon. 3(8): e00390.

Farin et al. (2012). "Redundant sources of Wnt regulate intestinal stem cells and promote formation ofPaneth cells," Gastroenterology, 143: 1518-1529.

Foltz et al. (2002). "Glycogen Synthase Kinase-3J3 Modulates Notch Signaling and Stability." Current Biology, vol. 12, No. 12, pp. 1006-1011.

Ford et al. (2008). "Qualitative and quantitative characterization of the amyloid ? peptide (A?) population in biological matrices using an immunoprecipitation-LC/MS assay." Journal of neuroscience methods. 168.2: 465-474.

Fu et al. (2008). "SM16, an Orally Active TFG-f3 Type I Receptor Inhibitor Prevents Myofibroblast Induction and Vascular Fibrosis in the Rat Carotid Injury Model." Arteriosclerosis, Thrombosis and Vascular Biology, vol. 28, No. 4, pp. 665-671.

Fujioka et al. (2011). "Development of Auditory-Specific Brain Rhythm in Infants," European Journal of Neuroscience, 33:521-529.

Fuller et al. (2012). "Intestinal crypts reproducibly expand in culture", J. Surg. Res., 178(1): 48-54.

Gale et al. (2010). "Cochlear Supporting Cells," Chapter 11 in Oxford Handbook of Auditory Science: The Ear, 31 pages.

Garcia-Berrocal Jr. et al. (2006). "Alternatives to Systemic Steroid Therapy for Refractory Immune-Mediated Inner Ear Disease: A Physiopathologic Approach." Eur. Arch. Otorhinolarynqol. vol. 263, No. 11, pp. 977-982.

Gellibert et al. (2004). "Identification of 1, 5-Naphthyridine Derivatives as a Novel Series of Potent and Selective TGF-Beta Type 1 Receptor Inhibitors." J. Med. Chern. vol. 47, No. 18, pp. 4494-4506.

Gupta et al. (2006). "Fast-Gelling Injectable Blend ofHyaluronan and Methylcellulose for Intrathecal, Localized Delivery to the Injured Spinal Cord." Biomaterials, 27: 2370-2379.

Haegebarth et al. (2009). "Wnt Signaling, Lgr5, and Stem Cells in the Intestine and Skin." The American Jounral of Pathology. vol. 174, No. 3, pp. 715-721.

Haggarty et al. (2003). "Domain-Selective Small-Molecule Inhibitor ofHistone Deacetylase 6 (HDAC6)-Mediated Tubulin Deacetylation", Proc. Nat 'l. Acad Sci. USA, 100(8): 4389-4394.

Halder et al. (2005). "A Specific Inhibitor of TGF-f3 Receptor Kinase, SB-431542, as a Potent Antitumor Agent for Human Cancers." Neoplasia. vol. 7, No. 5, pp. 509-521.

Harding et al. (2005). "The effect of an age-related hearing loss gene (Ahl) on noise induced hearing loss and cochlear damage from low-frequency noise." Hearing Research, 204: 90-100.

Herraiz et al. (2010). "Intratympanic Drug Delivery for the Treatment ofInner Ear Diseases," Acta Otorrinolaringologica Espanola, 61(3): 225-232.

Hong et al. (1998). "Human Dynamin-Like Protein Interacts with the Glycogen Synthase Kinase 3f3." Biochem. Biophys. Res. Commun. vol. 249, No. 3, pp. 697-703.

Hou et al. (2013). "Pluripotent Stem Cells Induced from Mouse Somatic Cells by Small-Molecule Compounds." Science. 341(6146): 651-654.

Huang et al. (2009). "Systematic and Integrative Analysis of Large Gene Lists Using DAVID Bioinformatics Resources," Nature Protocols, 4(1):44-57.

Huang et al. (2009). "RAD18 Transmits DNA Damage Signaling to Elicit Homologous Recombination Repair." Nat. Cell. Biol., vol. 11, No. 5, pp. 592-603.

Huang et al. (2009). "Directed, Efficient, and Versatile Modifications of the *Drosophila* Genome by Genomic Engineering." PNAS. vol. 106, No. 20, pp. 8284-9290.

International Search Report for Int'l Application No. PCT/US2014/023197, titled: "Compositions and Methods for Epithelial Stem Cell Expansion and Culture"; dated May 28, 2014.

International Preliminary Report on Patentability for Int'l Application No. PCT/US2014/023197, titled: "Compositions and Methods for Epithelial Stem Cell Expansion and Culture"; dated Sep. 15, 2015.

International Preliminary Report on Patentability for Int'l Application No. PCT/US2015/048442, titled: "Compositions, Systems, and Methods for Generating Inner Ear Hair Cells For Treatment of Hearing Loss"; dated Mar. 7, 2017.

Isaacson et al. (2003). "Differential Diagnosis and Treatment of Hearing Loss." American Family Physician. vol. 18, pp. 1125-1132.

Itoh et al. (2016). "False HDAC inhibition by aurone compound." Chemical and Pharmaceutical Bulletin, vol. 64, pp. 1124-1128.

Izumikawa et al. (2005). "Auditory Hair Cell Replacement and Hearing Improvement by Atohl Gene Therapy in Deaf Mammals." Nat Med., 11(3): 271-276.

Jeon et al. (2011). "Notch Signaling Alters Sensory or Neuronal Cell Fate Specification OfInner Ear Stem Cells." Journal Neurosci. vol. 31, No. 23, pp. 8351-8358.

Jung et al. (2011). "Isolation and in vitro expansion of human colonic stem cells," Nat. Med., 17, 1225-1227.

Kawamoto, T. (2003). "Use of a New Adhesive Film for the Preparation of Multi-Purpose Fresh-Frozen Sections from Hard Tissues, Whole-Animals, Insects and Plants." Arch. Histol. Cytol. vol. 66, No. 2, pp. 123-143.

Kazanjian et al. (2010). "Atonal homolog 1 is required for growth and differentiation effects of notch/gamma-secretase inhibitors on normal and cancerous intestinal epithelial cells," Gastroenterology, 139: 918-928.

Koch et al. (2013). "Stem cells living with a Notch." The Company of Biologists Ltd. Development, vol. 140, pp. 689-704.

Kujawa et al. (1997). "Conditioning-Related Protection from Acoustic Injury: Effects of Chronic Deefferentation and Sham Surgery," J. Neurophysiol., vol. 78, pp. 3095-3106.

Lanford et al. (1999). "Notch Signaling Pathway Mediates Hair Cell Development in Mammalian Cochlea." Nature Genetics. vol. 21, pp. 289-292.

Lasak et al. (2014). "Hearing Loss: Diagnosis and Management." Primary Care, vol. 41, pp. 19-31.

Lehner et al. (1997). "A Totally Implantable Drug Delivery System for Local Therapy of the Middle and Inner Ear." Ear, Nose, & Throat Journal, 76(8):567-570.

(56) References Cited

OTHER PUBLICATIONS

Li et al. (1998). "Interaction of Glycogen Synthase Kinase 3(3 with the DF3/MUC1 Carcinoma-Associated Antigen and f3-Catenin." Molecular and Cellular Biology, vol. 18, No. 12, pp. 7216-7224.
Li et al. (2003). "Retinoic Acid Stimulates Chondrocyte Differentiation and Enhances Bone Morphogenetic Protein Effects through Induction of Smadl and Smad5." Endocrinology. Vol. 144, No. 6, pp. 2514-2523.
Li et al. (2010). "Generation of iPSCs from mouse fibroblasts with a single gene, Oct4, and small molecules." Cell Research. 21(1): 196-204.
Liu et al. (2012). "In vivo Notch reactivation in differentiating cochlear hair cells induces Sox2 and Proxl expression but does not disrupt hair cell maturation." Dev Dyn., vol. 241, pp. 684-696.
Lu et al. (2008). "The Influence of Glycogen Synthase Kinase 3 in Limiting Cell Addition in the Mammalian Ear," pp. 1059-1075, published online in Wiley InterScience (www.interscience.wiley. com).
Lukacs et al. (2010). "Isolation, cultivation and characterization of adult murine prostate stem cells," Nat. Protoc., 5(4):702-713.
Lumpkin et al. (2003). "Mathl-Driven GFP Expression in the Developing Nervous System of Transgenic Mice," Gene Expr Patters, 3(4): 389-395.
Mai et al. (2005). "Class II IIIa)-selective histone deacetylase inhibitors. 1. Synthesis and biological evaluation of novel (aryloxopropenyl) pyrrolyl hydroxyamides." Journal of medicinal chemistry 48.9: 3344-3353.
Maison et al. (2003). "Olivocochlear Innervation in the Mouse: munocytochemical Maps, Crossed Versus Uncrossed Contributions, and Transmitter Colocalization." J. Comp. Neural., vol. 455, No. 3, pp. 406-416.
Mak et al. (2003). "The Tuberin-Hamartin Complex Negatively Regulates ,8-Catenin Signaling Activity." The Journal of Biological Chemistry. vol. 278, No. 8, 5947-5951.
Martinez-Monedero et al. (2008). "Differentiation of Inner Ear Stem Cells to Functional Sensory Neurons." Developmental Neurobiology. vol. 68, No. 5, pp. 669-684.
McCall et al. (2010). "Drug Delivery for Treatment of Inner Ear Disease: Current State of Knavvledge." Ear and Hearing, vol. 31, No. 2, pp. 156-165.
Meng et al. (2009). "Gamma-Secretase Inhibitors Abrogate Oxaliplatin-Induced Activation of the Notch-1 Signaling Pathway in Colon Cancer Cells Resulting in Enhanced Chemosensitivity." Cancer Research. vol. 69, pp. 573-582.
Mikulec et al. (2008). "Permeability of the Round Window Membrane is Influenced by the Composition of Applied Drug Solutions and by Common Surgical Procedures." Otol. Neurotol. vol. 29, No. 7, pp. 1020-1026.
Mills, D.M. (2006). "Determining the Cause of Hearing Loss: Differential Diagnosis Using a Comparison of Audiometric and Otoacoustic Emission Responses," Ear and Hearing, 27(5):508-525.
Mimasu et al. (2008). "Crystal structure of histone demelhylase LSD1 and tranylcypromine at 2.25 A," Biochemical and Biophysical Research ommunications, vol. 366, pp. 15-22.
Mimura et al. (2006). "Topical Ocular Drug Delivery to Inner Ear Disease and Sinusitis," Southern Medical Journal, 99(11): 1287-1289.
Mizutari et al. (2013). "Notch Inhibition Induces Cochlear Hair Cell Regeneration and Recovery of Hearing after Acoustic Trauma." Neuron, vol. 77, No. 1, pp. 58-69.
Mizutari et al. (2014). "Spontaneous Recovery of Cochlear Fibrocytes After Severe Degeneration Caused by Acute Energy Failure." Frontiers in Phamcacology, vol. 5, No. 198, pp. 1-3.
Moore et al. (2009). "Modulation of Wnt signaling through inhibition of secreted frizzled-related protein I (sFRP-1) with N-substituted piperidinyl diphenylsulfonyl sulfonamides." Journal of medicinal chemistry. 52.1: 105-116.
Mundada et al. (2009). "In Situ Gelling Polymers in Ocular Drug Delivery Systems: A Review," Critical Reviews in Therapeutic Drug Carrier Systems, 26(1):85-118. (Impact Factor-3.99).

Nakagawa et al. (2011). "Local Drug Delivery to the Inner Ear Using Biodegradable Materials," Therapeutic Delivery, 2(6):807-814.
Nakamura et al. (1998). "Axin, An Inhibitor of the Wnt Signalling Pathway, Interacts ,vith f3-Catenin, GSK-3(3 and APC and Reduces the f3-Catenin Level." Genes Cells, vol. 3, No. 6, pp. 395-403.
Okochi et al. (2006). "Secretion of the Notch-1 A?-like peptide during Notch signaling." Journal of Biological Chemistry. 281.12: 7890-7898.
Olsauskas-Kuprys et al. (2013). "Gamma Secretase Inhibitors of Notch Signaling." OncoTargets and Therapy, vol. 6, pp. 943-955.
Oshima et al. (2007). "Phylogenetic Relationships Among Mycoplasmas Based on the Whole Genomic Information," J. Mol. Evol., 65(3):249-258.
Paasche et al. (2003). "Technical Report: Modification of a Cochlear Implant Electrode for Drug Delivery to the Inner Ear," Otology & Neurotology, 24:222-227.
Pararas et al. (2011). "Kinetics of Reciprocating Drug Delivery to the Inner Ear." Journal of Controlled Release: Official Journal of the Controlled Release Society, 152:270-277.
Paulson et al. (2008). "A Novel Controlled Local Drug Delivery System for Inner Ear Disease," Otology/Basic and Clinical Research; The Laryngoscope, vol. 118:706-711.
Peer et al. (2007). "Nanocarriers as an Emerging Platform for Cancer Therapy," Nature Nanotechnology, 2:751-760.
Peterson et al. (2008). "Oral Administration of GW788388, An Inhibitor of TGF-f3 Type I and II Receptor Kinases, Decreases Renal Fibrosis." Kidney International, vol. 73, pp. 705-715.
Plontke et al. (2002). "Pharmacokinetic Considerations in Intratympanic Drug Delivery to the Inner Ear," Acta Oto-Rhino-Laryngologica Belgica, 56(4): 369-370.
Plontke et al. (2002). Transtympanic Endoscopy for Drug Delivery to the Inner Ear Using a New Microendoscope/ Advances in Oto-Rhino-Laryngology, 59: 149-155.
Plontke et al. (2004). "ID-and 3D-Computer Simulation for Experimental Planning and Interpretation of Pharmacokinetic Studies in the Inner Ear After Local Drug Delivery." Altex, vol. 21, Suppl 3, pp. 77-85.
Plontke et al. (2006). "Simulation of Application Strategies for Local Drug Delivery to the Inner Ear." ORL Journal for Oto-Rhino-Laryngology and Its Related Specialties. vol. 68, No. 6, pp. 386-392.
Plontke et al. (2006). "Technical Note on Microcatheter Implantation for Local Inner Ear Drug Delivery: Surgical Technique and Safety Aspects," Otology & Neurotology, 27(7):912-917.
Plontke et al. (2007). "Cochlear Pharmacokinetics With Local Inner Ear Drug Delivery Using a Three-Dimensional Finite-Element Computer Model." Audiology & Neuro-Otology, vol. 12, pp. 37-48.
Plontke et al. (2008). "Dexamethasone Concentration Gradients Along Scala Tympani After Application to the Round Window Membrane," Otology & Neurotology, 29(3):401-406.
Plontke et al. (2009). "Randomized Double Blind, Placebo Controlled Trial on the Safety and Efficacy of Continuous Intratympanic Dexamethasone Delivered Via a Round Window Catheter for Severe to Profound Sudden Idiopathic Sensorineural Hearing Loss After Failure of Systemic Therapy." The Laryngoscope, 119:359-369 (2009).
Plontke, S.K. (2011). "Evaluation of the Round Window Niche Before Local Drug Delivery to the Inner Ear Using a New Mini-Otoscope," Otology & Neurotology, 32(1): 183-185.
Provenzano et al. (2007). "A role for epigenetics in hearing: Establishment and maintenance of auditory specific gene expression patterns," Hearing Res., 233(1-2): 1-13.
Purow, B. (2012). "Notch Inhibition as a Promising New Approach to Cancer Therapy," Advances in Experimental Medicine and Biology, 727:305-319.
Raphael, Y. (1992). "Evidence for Supporting Cell Mitosis in Response to Acoustic Trauma in the Avian Inner Ear." Journal of Neurocytology, 21:663-671.
Richardson et al. (2008). "Novel Drug Delivery Systems for Inner Ear Protection and Regeneration After Hearing Loss," Expert Opinion on Drug Delivery, 5(10): 1059-1076.

(56) References Cited

OTHER PUBLICATIONS

Roy et al. (2010). "Cell-Specific Targeting in the Mouse Inner Ear Using Nanoparticles Conjugated with a Neurotrophin-Derived Peptide Ligand: Potential Tool for Drug Delivery," International Journal of Pharmaceutics, 390: 214-224.
Ryals et al. (2013). "Return of Function After Hair Cell Regeneration," Hearing Research, 297: 113-120.
Sage et al. (2005). "Proliferation of Functional Hair Cells in Vivo in the Absence of the Retinoblastoma Protein." Science. Vol. 307, pp. 1114-1118.
Sage et al. (2006). "Essential role of retinoblastoma protein in mammalian hair cell development and hearing." Proc. Natl. Acad. Sci. USA. vol. 103, pp. 7345-7350.
Sakamoto et al. (2010). "Inner Ear Drug Delivery System from the Clinical Point of View." Acta Oto-Laryngologica, 130:sup563: 101-104.
Salt et al. (2005). "Local Inner Ear Drug Delivery and Phannacokinetics." Drug. Discov. Today, vol. 10, No. 19, pp. 1299-1306.
Salt et al. (2008). "Dependence of Hearing Changes on the Dose of intratympanically Applied Gentamicin: A Meta-Analysis Using Mathematical Simulations of Clinical Drug Delivery Protocols." The Laryngoscope, 118(10): 1793-1800.
Salt et al. (2008). "Dexamethasone Concentration Gradients Along Scala Tympani After Application to the Round Windmv Membrane," Otology & Neurotology, 29(3):401-406.
Salt et al. (2009). "Principles of Local Drug Delivery to the Inner Ear." Audiol. Neurotol. vol. 14, No. 6, pp. 350-360.
Salt, A. (2010). "Guest Editorial: Drug Delivery for Treatment of Inner Ear Disease: Current State of Knowledge." Ear and Hearing, vol. 31, p. 155.
Salt et al. (2011). "Distribution of Dexamethasone and Preservation of Inner Ear Function Following Intratympanic Delivery of a Gel-Based Formulation." Audiology & Neuro-otology, vol. 16, pp. 323-335.
Salvi et al. (2008). "Hair Cell Regeneration, Repair, and Protection." Springer Handbook of Auditory Research. vols. 1-33, 323.
Sataloff, et al. (2001). "Differential Diagnosis of Occupational Hearing Loss." Occupational Health & Safety, 70(9): 126-129.
Sato et al. (2011). "Long-term expansion of epithelial organoids from human colon, adenoma, adenocarcinoma, and Barrett's epithelium," Gastroenterology, 141: 1762-1772.
Sato et al. (2011). "Paneth cells constitute the niche for Lgr5 stem cells in intestinal crypts," Nature, 469:415-418.
Sawyer et al. (2003). "Synthesis and Activity of New Aryl- and Heteroaryl-Substituted Pyrazole Inhibitors of the Transforming Gro'"1h Factor-Beta Type 1 Receptor Kinase Domain." J. Med. Chem., vol. 46, No. 19, pp. 3953-3956.
Sawyer et al. (2004). "Synthesis and Activity of New Aryl- and Heteroaryl-Substituted 5,6-Dihiydro-4HPyrrolo[l,2-b]Pyrazole Inhibitors of the Transforming Growth Factor-Beta Type I Receptor Kinase Domain," Bioorg. Med. Chem. Lett., vol. 14, No. 13, pp. 3581-3584.
Schwarz-Romond et al. (2002). "The Ankyrin Repeat Protein Diversin Recruits Casein Kinase le to the f3-Catenin Degradation Complex and Acts in Both Canonical Wnt and Wnt/JNK Signaling." Genes, Dev., vol. 16, No. 16, pp. 2073-2084.
Scoville et al. (2008). "Current view: intestinal stem cells and signaling," Gastroenterology, 134(3): 849-864.
Seidman, M.D. (1998). "'Glutamate Antagonists, Steroids, and Antioxidants as Therapeutic Options for Hearing Loss and Tinnitus and the Use of an Inner Ear Drug Delivery System." The International Tinnitus Journal, vol. 4, pp. 148-154.
Sekine et al. (2006). "Hathl Up-Regulates Gastric Mucin Gene Expression in Gastric Cells." Biochem. Biophys. Res. Commun., 344(4): 1166-71.
Shariatmadari et al. (2005). "Increased Wnt Levels in the Neural Tube Impair the Function of Adherens Junctions During Neurulation," Mol Cell Neurosci.,30(3): 437-51. Epub (abstract only).

Shi et al. (2010). "Beta-Catenin Up-Regulates Atohl Expression in Neural Progenitor Cells by Interaction with an Atohl 3' Enhancer." The Journal of Biological Chemistry, vol. 285, pp. 392-400.
Shi et al. (2012). "Wnt-Responsive Lgr5-Expressing Stem Cells Are Hair Cell Progenitors in the Cochlea." J Neuroscience, 32 (28): 9639-9648.
Shi et al. (2013). "Generation of Hair Cells in Neonatal Mice by f3-Catenin Overexpression in Lgr5-Positive Cochlear Progenitors." Proc Natl Acad Sci USA, vol. 110, No. 34, p. 13851-13856.
Shih et al. (2007). "Notch Signaling, Gamma-Secretase Inhibitors, and Cancer Therapy." Cancer Research, vol. 67, pp. 1879-1882.
Shoichet et al. (2007). "Intrathecal Drug Delivery Strategy is Safe and Efficacious for Localized Delivery to the Spinal Cord," Progress in Brain Research, 161:385-392.
Snippert et al. (2010). "Intestinal crypt homeostasis results from neutral competition between symmetrically dividing Lgr5 stem cells," Cell, 143: 134-144.
Staecker et al. (2004). "Drug Delivery to the Inner Ear Using Gene Therapy," Otolaryngologic Clinics of North America, vol. 37, pp. 1091-1108.
Swan et al. (2008). "Inner Ear Drug Delivery for Auditory Applications." Adv. Drug. Deliv. Rev., vol. 60, No. 15, pp. 1583-1599.
Tojo et al. (2005). "The ALK-5 Inhibitor A-83-01 Inhibits Smad Signaling and Epithelial-to-Mesenchymal Transition by Transforming Growth Factor-f3." Cancer Sci., vol. 96, No. 11, pp. 791-800.
Valdimarsdottir et al. (2005). "Functions of the TGFf3 Superfamily in Human Embryonic StempCells." APMIS. vol. 113, pp. 773-389.
Van Der Flier et al. (2009). "Stem cells, self-renewal, and differentiation in the intestinal epithelium," Annual Review of Physiology, 71: 241-260.
Van Dussen et al. (2012). "Notch signaling modulates proliferation and differentiation of intestinal crypt base columnar stem cells." The Company of Biologists Ltd., Development 139, pp. 488-497.
Van Es et al. (2005). "Notch/gamma-secretase inhibition turns proliferative cells in intestinal crypts and adenomas into goblet cells," Nature, 435: 959-963.
Van Es et al. (2010). "Intestinal stem cells lacking the Mathl tumour suppressor are refractory to Notch inhibitors." Nat. Commun., 1(18): 1-5.
Van Tomme et al. (2008). "In Situ Gelling Hydrogels for Phannaceutical and Biomedical Applications." Int. J. Pharm., 355(1-2): 1-18.
Von Kries et al. (2000). "Hot Spots in Beta-Catenin for Interactions with LEF-1, Conductin and APC." Nat. Struct. Biol., vol. 7, No. 9, pp. 800-807.
Voytik-Harbin et al. (1998). "Small Intestinal Submucosa: A Tissue-Derived Extracellular Matrix That Promotes Tissue-Specific Growth and Differentiation of Cells in Vitro." Tissue Engineering, 4(2): 157-174.
Wagner et al. (2009). "Modeling, synthesis and biological evaluation of potential retinoid X receptor (RXR) selective agonists: novel analogues of 4-[1-(3, 5, 5, 8, 8-pentamethyl-5, 6, 7, 8-tetrahydro-2-naphthyl) ethynyl] benzoic acid (bexarotene)." Journal of medicinal chemistry. 52.19: 5950-5966.
Wang et al. (2002). "Dynamics of Noise-Induced Cellular Injury and Repair in the Mouse Cochlea," J. of the Assoc. of Research in Otolaryngology, 3:248-268.
Wang et al. (2004). "Suppression of Androgen Receptor-Mediated Transactivation and Cell Growth by the Glycogen Synthase Kinase 3f3 in Prostate Cells." Journal of Biological Chemistry, vol. 279, No. 31, p. 32444-32452.
Warchol et al. (1996). "Regenerative Proliferation in Organ Cultures of the Avian Cochlea: Identification of the Initial Progenitors and Determination of the Latency of the Proliferative Response." The Journal of Neuroscience: the Official Journal of the Society for Neuroscience. vol. 16, pp. 5466-5477.
White et al. (2006). "Mammalian Cochlear Supporting Cells Can Divide and Trans-Differentiate Into Hair Cells." Nature, vol. 441, No. 7096, pp. 984-987.
Wong et al. (2015). "Mechanisms of sensorineural cell damage, death and survival in the cochlea." Frontiers in Aging Neuroscience. vol. 7, Article 58, pp. 1-15.

(56) References Cited

OTHER PUBLICATIONS

Written Opinion of The International Searching Authority for Int'l Application No. PCT/US2014/023197, titled: "Compositions and Methods for Epithelial Stem Cell Expansion and Culture"; dated May 28, 2014.
Wu et al. (2004). Modulation of Notch Signaling by Mastermind-Like (MAML) Transcriptional Co-Activators and Their Involvement in Tumorigenesis/ Seminars in Cancer Biology, 14: 348-356.
Yang et al. (2012). "Functional Features of Trans-Differentiated Hair Cells Mediated by Atoh1 Reveals a Primordial Mechanism." J. ofNeuroscience, 32(11):3712-3725.
Yang et al. (2013). "Ectopic Hair Cell-Like Cell Induction by Math1 Mainly Involves Direct Transdifferentiation in Neonatal Mammalian Cochlea," Neuroscience Letters, 549:7-11.
Yao et al. (2010). "Prostate-regenerating capacity of cultured human adult prostate epithelial cells," Cells Tissues Organs, 191: 203-212.
Yilmaz et al. (2012). "mTORCI in the Paneth cell niche couples intestinal stem-cell function to calorie intake," Nature, 486: 490-495.
Yin et al. (2013). "Niche-Independent High-Purity Cultures ofLgr5+ Intestinal Stem Cells and Their Progeny." Nat. Methods, vol. 11, No. 1, pp. 106-112.
Ying et al. (2008). "The ground state of embryonic stem cell self-renewal," Nature, 453: 519-523.
Yingling et al. (2004). "Development of TGF-B Signalling Inhibitors for Cancer Therapy." Nature Reviews Drug Discovery. vol. 3, No. 12, pp. 1011-1022.
Yu et al. (2010). "In vivo proliferation of postmitotic cochlear supporting cells by acute ablation of the retinoblastoma protein in neonatal mice." J Neurosci, vol. 30, pp. 5927-5936.
Yuge et al. (2004). "Transplanted Human Amniotic Epithelial Cells Express Connexin 26 and Na-Kadenosine Triphophatase in the Inner Ear." Transplantation. vol. 77, No. 9, pp. 1452-1454.
Yui et al. (2012). "Functional engraftment of colon epithelium expanded in vitro from a single adult Lgr5+ stem cell," Nature Medicine, 18(4): 618-623.
Zahnert, T. (2011). "The Differential Diagnosis of Hearing Loss." Deutsches Arzteblatt International. vol. 108, pp. 433-443, quiz 44.
Zhang et al. (2003). "Inhibitory Phosphorylation of Glycogen Synthase Kinase-3 (GSK-3) in Response to Lithium," J. Bio. Chem., 278(3): 33067-33077.
Zhao et al. (2015). "A XEN-like State Bridges Somatic Cells to Pluripotency during Chemical Reprogramming." Cell. 163(7): 1678-1691.
Zheng et al. (2000). "Overexpresson of Math1 Induces Robust Production of Extra Hair Cells in Postnatal Rat Inner Ears," Nature Neuroscience, 3(6): 580-586.
De Los Angeles et al. (2013). "A chemical logic for reprogramming to pluripotency," Cell Research, vol. 23, No. 12, pp. 1337-1338.
International Search Report and Written Opinion for Int'l Application No. PCT/US2015/048442, dated Jan. 29, 2016, 10 pages.
Lin et al. (2011). "Inhibition of Notch Activity Promotes Nonmitotic Regeneration of Hair Cells in the Adult Mouse Utricles," The Journal of Neurosciencce, vol. 31, No. 43, p. 15329-15339.
Zheng. (2009). "Polymers in Pharmaceuticals," China Medical Science and Technology Press, p. 219.

\* cited by examiner

THERMOREVERSIBLE COMPOSITIONS FOR ADMINISTRATION OF THERAPEUTIC AGENTS

RELATED APPLICATIONS

This application is a divisional application of U.S. application Ser. No. 15/447,682, filed on Mar. 2, 2017 (now allowed), which claims the benefit of and priority to U.S. Provisional Application No. 62/302,747, filed Mar. 2, 2016, the entire contents of each of which are incorporated herein by reference in their entireties.

FIELD OF THE INVENTION

The present invention relates to thermoreversible compositions of poloxamers and methods of using same for administration of therapeutic agents

BACKGROUND OF THE INVENTION

Poloxamers are nonionic triblock copolymers composed of a central hydrophobic chain of polyoxypropylene (poly(propylene oxide)) flanked by two hydrophilic chains of polyoxyethylene (poly(ethylene oxide)). Poloxamers are often considered "functional excipients" because they are essential components and play an important role in a formulation.

Poloxamers are synthetic triblock co-polymers with the following general structure formula:

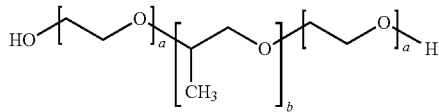

wherein a=2-130 and b=15-67

Non-limiting examples of poloxamers include: poloxamer 124, poloxamer 184, poloxamer 185, poloxamer 188, poloxamer 237, poloxamer 338, and poloxamer 407. The chemical characteristics of each poloxamer are determined by the chain length of the polyethylene (EO) units and the polyoxypropylene (PO) units, molecular weight and degree of hydrophobicity/hydrophilicity. Some poloxamers are liquid at room temperature (124) whereas others are a solid (184, 185, 188, 237, 338, and 407). Poloxamers have a variety of uses including as emulsifying agents, solubilizing agents and stabilizing agents. For example, poloxamer 188 has been used as an emulsifying agent for fluorocarbons used as artificial blood substitutes and in the preparation of solid-dispersions. They are also used as wetting agents in ointments, suppository bases, and gels, as well as tablet binders and coatings. In some cases, poloxamers have been used for solubilizing formulations containing otic therapeutic agents and their delivering. In some cases, a poloxamer formulation is created containing active agents that is liquid when at 4° C. which gels when heated at or above room temperature. This enables the formulation to be injected through a small needle and gel when it hits the middle ear. In these cases the amounts of poloxamer used for solubilization was about 15-17 wt %. At concentrations above 15-17 wt %, poloxamers will typically form gels that are not flowable even with cooled to 4° C., making them unsuitable for injection. There is a need for injectable formulations of therapeutic agents containing a poloxamer with gelation temperatures of at least 10 degrees or at least body temperature, where the poloxamer is at concentrations higher than about 15-17 wt %.

SUMMARY OF THE INVENTION

In one aspect, the present disclosure provides a poloxamer containing pharmaceutical composition having a gelation temperature greater than 10° C., the composition comprising:

a) a pharmaceutically active therapeutic agent or a pharmaceutically acceptable salt thereof;
b) a poloxamer at greater than or equal to 21 wt % of the pharmaceutical composition; and
c) a carboxylic acid containing compound;
wherein the pharmaceutical composition has a gelation temperature of greater than 10° C.

In some embodiments, the poloxamer comprises at least one of Poloxamer 124, Poloxamer 188, Poloxamer 237, Poloxamer 338 or Poloxamer 407. In some embodiments, the poloxamer comprises a mixture of two or more of Poloxamer 124, Poloxamer 188, Poloxamer 237, Poloxamer 338 or Poloxamer 407. In some embodiments, the mixture of two or more poloxamers comprises Poloxamer 407 and Poloxamer 124. In another embodiment, the Poloxamer comprises at least one of Poloxamer 188 and Poloxamer 407 or mixtures thereof. In some embodiments, the poloxamer is Poloxamer 407.

In some embodiments, the poloxamer can be in a concentration between 21 wt % and 40 wt % relative to the composition. In another embodiment, the poloxamer is in a concentration between 21 wt % and 30 wt % relative to the composition. In another embodiment, the poloxamer is in a concentration between 23 wt % and 29 wt % relative to the composition. In another embodiment, the poloxamer is in a concentration between 23 wt % and 27 wt % relative to the composition. In another embodiment, the poloxamer is in a concentration of 25 wt % relative to the composition.

In some embodiments, the gelation temperature of the pharmaceutical composition is between about 11° C. and about 32° C. In some embodiments, the gelation temperature of the pharmaceutical composition is between is between about 15° C. and about 30° C. In some embodiments, the gelation temperature of the pharmaceutical composition is between about 20° C. and about 28° C. In some embodiments, the gelation temperature of the pharmaceutical composition is between about 24° C. and about 26° C.

In some embodiments, the gelation temperature of the pharmaceutical composition is about 15° C. In some embodiments, the gelation temperature of the pharmaceutical composition is about 20° C. In some embodiments, the gelation temperature of the pharmaceutical composition is about 24° C. In some embodiments, the gelation temperature of the pharmaceutical composition is about 26° C. In some embodiments, the gelation temperature of the pharmaceutical composition is about 28° C. In some embodiments, the gelation temperature of the pharmaceutical composition is about 30° C. In some embodiments, the gelation temperature of the pharmaceutical composition is about 32° C.

In any of the foregoing embodiments, the carboxylic acid containing compound is a substituted or unsubstituted $C_5$-$C_9$ straight or branched chain alkyl-$CO_2H$.

In any of the foregoing embodiments, the carboxylic acid containing compound is a substituted $C_5$-$C_9$ straight or branched chain alkyl-$CO_2H$.

In some embodiments, the carboxylic acid containing compound is a substituted $C_5$-$C_9$ straight or branched chain alkyl-CO$_2$H, wherein the substituent is –NH$_2$. In some examples the carboxylic acid containing compound is an amino substituted 2-propylpentanoic acid. In some embodiments, the amino substituted 2-propylpentanoic acid is selected from the group consisting of 5-amino-2-propylpentanoic acid, 4-amino-2-propylpentanoic acid, 3-amino-2-propylpentanoic acid, and 2-amino-2-propylpentanoic acid.

In some embodiments, the carboxylic acid containing compound is an unsubstituted C$_5$-C$_9$ straight or branched chain alkyl-CO$_2$H.

In some embodiments, the carboxylic acid containing compound is an unsubstituted C$_6$-C$_9$ branched straight chain alkyl-CO$_2$H.

In some embodiments, the carboxylic acid containing compound is an unsubstituted C$_8$-C$_9$ branched straight chain alkyl-CO$_2$H.

In some embodiments, the carboxylic acid containing compound is an unsubstituted C$_9$ branched straight chain alkyl-CO$_2$H.

In some embodiments, the unsubstituted C$_9$ branched straight chain alkyl-CO$_2$H carboxylic acid containing compound is Valproic acid.

In some embodiments, the Valproic acid can be in the form of an amide. In some embodiments, the amide form of Valproic acid is the condensation product with an amino acid. In some embodiments, the amide of Valproic acid is selected from the group consisting of

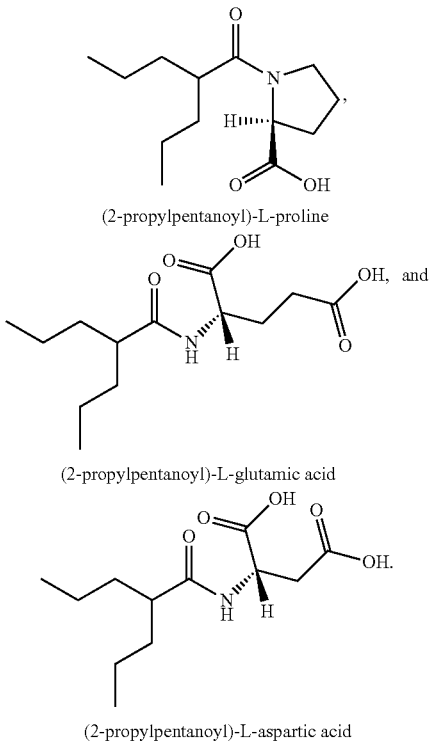

(2-propylpentanoyl)-L-proline (2-propylpentanoyl)-L-glutamic acid (2-propylpentanoyl)-L-aspartic acid In any of the foregoing embodiments, the amount of the carboxylic acid containing compound in the pharmaceutical composition is between at least 2 wt % (weight carboxylic acid containing compound/weight pharmaceutical composition) and 20 wt % (weight carboxylic acid containing compound/weight pharmaceutical composition). In some embodiments, the composition comprises at least 4 wt % carboxylic acid. In other embodiments, the composition comprises at least 8 wt % carboxylic acid. In some embodiments, the composition comprises at least 12 wt % carboxylic acid. In some embodiments, the composition comprises at least 16 wt % carboxylic acid. In still other embodiments, the composition comprises at least 20 wt % carboxylic acid.

In other embodiments, the composition comprises about 4 wt % carboxylic acid. In other embodiments, the composition comprises about 8 wt % carboxylic acid. In other embodiments, the composition comprises about 12 wt % carboxylic acid. In further embodiments, the composition comprises about 16 wt % carboxylic acid. In further embodiments, the composition comprises about 20 wt % carboxylic acid.

In some embodiments of the poloxamer containing pharmaceutical composition, the pharmaceutically active therapeutic agent is selected from the group consisting of a wnt agonist, a GSK3 inhibitor, a 2-pyrimidinylaminoethylamino-2-pyridine containing compound, a N-(1H-pyrazol-4-yl)-nicotinamide containing compound, and a 1,2,3,4-tetrahydro-[1,4]diazepino[6,7]indol-7-yl)-4-(imidazo[1,2-a]pyridin-3-yl)-1H-pyrrole-2,5-dione containing compound.

A further aspect of the present disclosure provides a poloxamer containing pharmaceutical composition having a gelation temperature greater than 10° C., the composition comprising:
  a) a wnt agonist or a pharmaceutically acceptable salt thereof;
  b) Poloxamer 407 at greater than or equal to 21 wt % of the pharmaceutical composition; and
  c) a carboxylic acid containing compound;
wherein the pharmaceutical composition has a gelation temperature of greater than 10° C.

A further aspect of the present disclosure provides a poloxamer containing pharmaceutical composition having a gelation temperature greater than 10° C., the composition comprising:
  a) a GSK3 inhibitor or a pharmaceutically acceptable salt thereof;
  b) Poloxamer 407 at greater than or equal to 21 wt % of the pharmaceutical composition; and
  c) a carboxylic acid containing compound;
wherein the pharmaceutical composition has a gelation temperature of greater than 10° C.

A further aspect of the present disclosure provides a poloxamer containing pharmaceutical composition having a gelation temperature greater than 10° C., the composition comprising
  a) a 2-pyrimidinylaminoethylamino-2-pyridine compound;
  b) Poloxamer 407 at greater than or equal to 21 wt % of the pharmaceutical composition; and
  c) a carboxylic acid containing compound;
wherein the pharmaceutical composition has a gelation temperature of greater than 10° C.

A further aspect of the present disclosure provides poloxamer containing pharmaceutical composition having a gelation temperature greater than 10° C., the composition comprising:
  a) an N-(alkylcarbamoyl)-1H-pyrazol-4-yl)-nicotinamide containing compound or a pharmaceutically acceptable salt thereof;
  b) Poloxamer 407 at greater than or equal to 21 wt % of the pharmaceutical composition; and
  c) a carboxylic acid containing compound;
wherein the pharmaceutical composition has a gelation temperature of greater than 10° C.

A further aspect of the present disclosure provides a poloxamer containing pharmaceutical composition having a gelation temperature greater than 10° C., the composition comprising:
    a) 1,2,3,4-tetrahydro-[1,4]diazepino[6,7]indol-7-yl)-1H-pyrrole-2,5-dione containing compound or a pharmaceutically acceptable salt thereof;
    b) Poloxamer 407 at greater than or equal to 21 wt % of the pharmaceutical composition; and
    c) a carboxylic acid containing compound;
wherein the pharmaceutical composition has a gelation temperature of greater than 10° C.

A further aspect of the present disclosure provides a poloxamer containing pharmaceutical composition having a gelation temperature greater than 10° C., the composition comprising:
    a) a compound of Formula I:

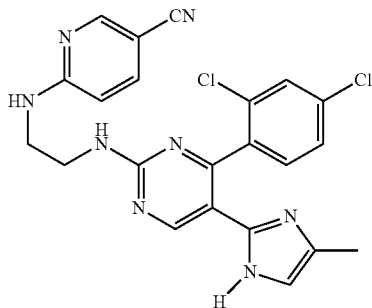

Formula I or a pharmaceutically acceptable salt thereof;
    b) Poloxamer 407 in weight percentage of more than 21% wt; and
    c) Valproic acid;
wherein the amount of Valproic acid in the pharmaceutical composition is between at least 2 wt % (weight carboxylic acid containing compound/weight pharmaceutical composition) and 20 wt % (weight carboxylic acid containing compound/weight pharmaceutical composition). In some embodiments, the composition comprises at least 4 wt % Valproic acid. In some embodiments, the composition comprises at least 8 wt % Valproic acid. In other embodiments, the composition comprises at least 12 wt % Valproic acid. In some embodiments, the composition comprises at least 16 wt % Valproic acid. In other embodiments, the composition comprises at least 20 wt % Valproic acid.

In other embodiments, the composition comprising Formula I, comprises between about 2 wt % Valproic acid and about 20 wt %. In other embodiments, the composition comprising Formula I, comprises about 2 wt % Valproic acid. In other embodiments, the composition comprising Formula I, comprises about 4 wt % Valproic acid. In other embodiments, the composition comprising Formula I, comprises about 8 wt % Valproic acid. In other embodiments, the composition comprising Formula I, comprises about 12 wt % Valproic acid. In further embodiments, the composition comprising Formula I, comprises about 16 wt % Valproic acid. In further embodiments, the composition comprising Formula I, comprises about 20 wt % Valproic acid.

A further aspect of the present disclosure provides a poloxamer containing pharmaceutical composition having a gelation temperature greater than 10° C., the composition comprising:
    a) a compound of Formula II

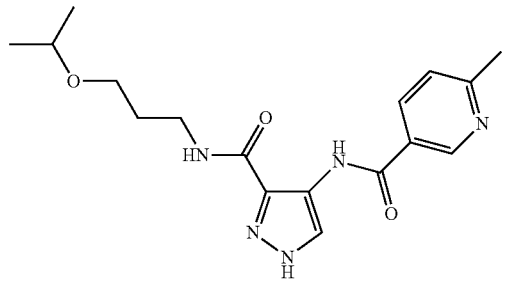

Formula II or a pharmaceutically acceptable salt thereof;
    b) Poloxamer 407 in weight percentage of more than 21% wt; and
    c) Valproic acid;
wherein the amount of Valproic acid in the pharmaceutical composition is between at least 2 wt % (weight carboxylic acid containing compound/weight pharmaceutical composition) and 20 wt %. In some embodiments, the composition comprising the compound of Formula II, comprises at least 4 wt % Valproic acid. In some embodiments, the composition comprising the compound of Formula II, comprises at least 8 wt % Valproic acid. In other embodiments, the composition comprising the compound of Formula II, comprises at least 12 wt % Valproic acid. In some embodiments, the composition comprising the compound of Formula II, comprises at least 16 wt % Valproic acid. In other embodiments, the composition comprising the compound of Formula II, comprises at least 20 wt % Valproic acid.

In other embodiments, the composition comprising Formula II, comprises between about 2 wt % Valproic acid and about 20 wt %. In other embodiments, the composition comprising Formula II, comprises about 2 wt % Valproic acid. In other embodiments, the composition comprising Formula II, comprises about 4 wt % Valproic acid. In other embodiments, the composition comprising Formula II, comprises about 8 wt % Valproic acid. In other embodiments, the composition comprising Formula II, comprises about 12 wt % Valproic acid. In further embodiments, the composition comprising Formula II, comprises about 16 wt % Valproic acid. In further embodiments, the composition comprising Formula II, comprises about 20 wt % Valproic acid.

A further aspect of the present disclosure provides a poloxamer containing pharmaceutical composition having a gelation temperature greater than 10° C., the composition comprising:
    a) a compound of Formula III

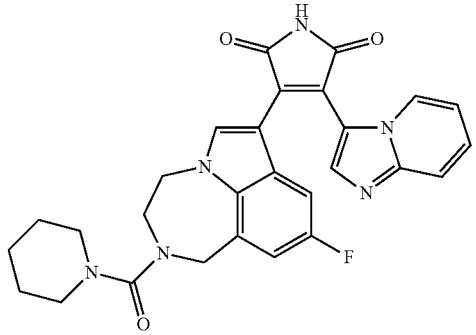

Formula III or a pharmaceutically acceptable salt thereof;

b) Poloxamer 407 in weight percentage of more than 21% wt; and c) Valproic acid;

wherein the amount of Valproic acid in the pharmaceutical composition is between at least 2 wt % (weight carboxylic acid containing compound/weight pharmaceutical composition) and 20 wt %.

In some embodiments, the composition comprising the compound of Formula III, comprises at least 4 wt % Valproic acid. In some embodiments, the composition comprising the compound of Formula III, comprises at least 8 wt % Valproic acid. In other embodiments, the composition comprising the compound of Formula III, comprises at least 12 wt % Valproic acid. In some embodiments, the composition comprising the compound of Formula III, comprises at least 16 wt % Valproic acid. In other embodiments, the composition comprising the compound of Formula III, comprises at least 20 wt % Valproic acid.

In other embodiments, the composition comprising Formula III, comprises between about 2 wt % Valproic acid and about 20 wt %. In other embodiments, the composition comprising Formula III, comprises about 2 wt % Valproic acid. In other embodiments, the composition comprising Formula III, comprises about 4 wt % Valproic acid. In other embodiments, the composition comprising Formula III, comprises about 8 wt % Valproic acid. In other embodiments, the composition comprising Formula III, comprises about 12 wt % Valproic acid. In further embodiments, the composition comprising Formula III, comprises about 16 wt % Valproic acid. In further embodiments, the composition comprising Formula III, comprises about 20 wt % Valproic acid.

DETAILED DESCRIPTION OF THE DISCLOSURE

Figure 1:
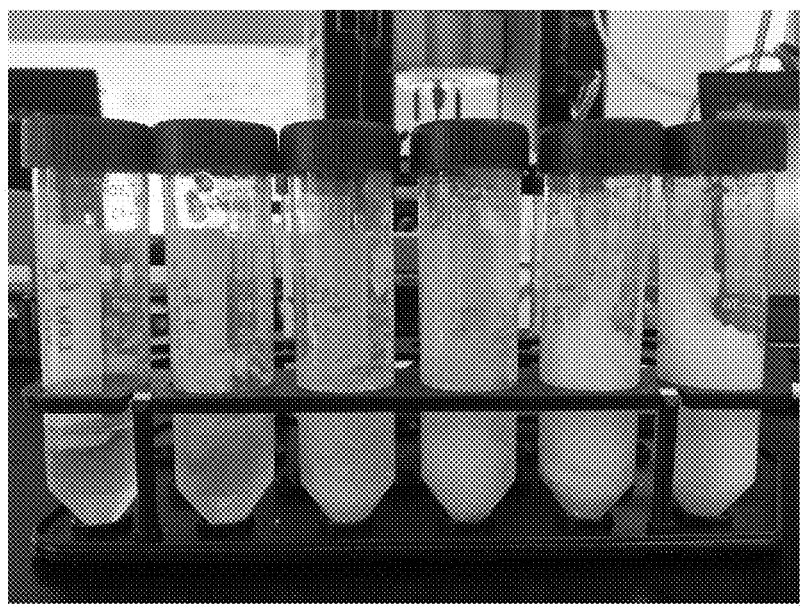
FIG. 1 is a photograph showing the solubility of Poloxamer 407 (P407) at 16.7% of w/w (16.7 grams Poloxamer 407 to 83.3 grams of a solution that contains % 1 Molar valproic acid sodium salt/5% weight DMSO and water), 28.6% w/w, 33.3% w/w, 37.5% w/w, 41.2% w/w, and 50.0% w/w in 1M Valproic acid sodium salt and 5% dimethylsulfoxide (DMSO) in water. Percent w/w of Poloxamer 407 left to right as shown: 16.7%, 28.6%, 33.3%, 37.5%, 41.2%, and 50.0%.

The present disclosure provides poloxamer containing pharmaceutical compositions which exhibit a gelation temperature greater than 10° C. These compositions comprise pharmaceutically active therapeutic agents or their pharmaceutically acceptable salts. Moreover, these pharmaceutical compositions comprise both poloxamer at greater than or equal to 21 wt % of the pharmaceutical composition and a carboxylic acid containing compound and have a gelation temperature of greater than 10° C. The carboxylic acid containing compound is in an amount of between at least 2 wt % and 20 wt %. These compositions are described herein as well as some non-limiting uses of same.

Definitions

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration" refers to introducing a substance into a subject. In some embodiments, administration is auricular, intraauricular, intracochlear, intravestibular, or transtympanically, e.g., by injection. In some embodiments, administration is directly to the inner ear, e.g., injection through the round or oval window, otic capsule, or vestibular canals. In some embodiments, administration is directly into the inner ear via a cochlear implant delivery system. In some embodiments, the substance is injected transtympanically to the middle ear. In certain embodiments "causing to be administered" refers to administration of a second component after a first component has already been administered (e.g., at a different time and/or by a different actor).

An "antibody" refers to an immunoglobulin polypeptide, or fragment thereof, having immunogen binding ability.

As used herein, an "agonist" is an agent that causes an increase in the expression or activity of a target gene, protein, or a pathway, respectively. Therefore, an agonist can bind to and activate its cognate receptor in some fashion, which directly or indirectly brings about this physiological effect on the target gene or protein. An agonist can also increase the activity of a pathway through modulating the activity of pathway components, for example, through inhibiting the activity of negative regulators of a pathway. Therefore, a "Wnt agonist" can be defined as an agent that increases the activity of Wnt pathway, which can be measured by increased TCF/LEF-mediated transcription in a cell. Therefore, a "Wnt agonist" can be a true Wnt agonist that binds and activates a Frizzled receptor family member, including any and all of the Wnt family proteins, an inhibitor of intracellular beta-catenin degradation, and activators of TCF/LEF.

An "antagonist" refers to an agent that binds to a receptor, and which in turn decreases or eliminates binding by other molecules.

"Anti-sense" refers to a nucleic acid sequence, regardless of length, that is complementary to the coding strand or mRNA of a nucleic acid sequence. Antisense RNA can be introduced to an individual cell, tissue or organanoid. An anti-sense nucleic acid can contain a modified backbone, for example, phosphorothioate, phosphorodithioate, or other modified backbones known in the art, or may contain non-natural internucleoside linkages.

As referred to herein, a "complementary nucleic acid sequence" is a nucleic acid sequence capable of hybridizing with another nucleic acid sequence comprised of complementary nucleotide base pairs. By "hybridize" is meant pair to form a double-stranded molecule between complementary nucleotide bases (e.g., adenine (A) forms a base pair with thymine (T), as does guanine (G) with cytosine (C) in DNA) under suitable conditions of stringency. (See, e.g., Wahl, G. M. and S. L. Berger (1987) Methods Enzymol. 152:399; Kimmel, A. R. (1987) Methods Enzymol. 152: 507).

"Auricular administration" refers to a method of using a catheter or wick device to administer a composition across the tympanic membrane to the inner ear of the subject. To facilitate insertion of the wick or catheter, the tympanic membrane may be pierced using a suitably sized syringe or pipette. The devices could also be inserted using any other methods known to those of skill in the art, e.g., surgical implantation of the device. In particular embodiments, the wick or catheter device may be a stand-alone device, meaning that it is inserted into the ear of the subject and then the composition is controllably released to the inner ear. In other particular embodiments, the wick or catheter device may be attached or coupled to a pump or other device that allows for the administration of additional compositions. The pump may be automatically programmed to deliver dosage units or may be controlled by the subject or medical professional.

"Biocompatible Matrix" as used herein is a polymeric carrier that is acceptable for administration to humans for the release of therapeutic agents. A Biocompatible Matrix may be a biocompatible gel or foam.

"Cell Aggregate" as used herein shall mean a body cells in the Organ of Corti that have proliferated to form a cluster of a given cell type that is greater than 40 microns in diameter and/or produced a morphology in which greater than 3 cell layers reside perpendicular to the basilar membrane. A "Cell Aggregate" can also refer a process in which cell division creates a body of cells that cause one or more cell types to breach the reticular lamina, or the boundary between endolymph and perilymph "Cell Density" as used herein in connection with a specific cell type is the mean number of that cell type per area in a Representative Microscopy Sample. The cell types may include but are not limited to $Lgr5^+$ cells, hair cells, or supporting cells. The Cell Density may be assessed with a given cell type in a given organ or tissue, including but not limited to the cochlea or Organ of Corti. For instance, the $Lgr5^+$ Cell Density in the Organ of Corti is the Cell Density of $Lgr5^+$ cells as measured across the Organ of Corti. Typically, supporting cells and $Lgr5^+$ cells will be enumerated by taking cross sections of the Organ of Corti. Typically, hair cells will be enumerated by looking down at the surface of the Organ of Corti, though cross sections may be used in some instances, as described in a Representative Microscopy Sample. Typically, Cell Density of $Lgr5^+$ cells will be measured by analyzing whole mount preparations of the Organ of Corti and counting the number of Lgr5 cells across a given distance along the surface of the epithelia, as described in a Representative Microscopy Sample. Hair cells may be identified by their morphological features such as bundles or hair cell specific stains (e.g., Myosin VIIa, Prestin, vGlut3, Pou4f3, Espin, conjugated-Phalloidin, PMCA2, Ribeye, Atohl, etc). Lgr5+ cells may be identified by specific stains or antibodies (e.g., Lgr5-GFP transgenic reporter, anti-Lgr5 antibody, etc.)

"Cochlear Concentration" as used herein will be the concentration of a given agent as measured through sampling cochlear fluid. Unless otherwise noted, the sample should contain a substantial enough portion of the cochlear fluid so that it is approximately representative of the average concentration of the agent in the cochlea. For example, samples may be drawn from a vestibular canal, and a series of fluid samples drawn in series such that individual samples are comprised of cochlear fluid in specified portions of the cochlea "Complementary nucleic acid sequence" refers to a nucleic acid sequence capable of hybridizing with another nucleic acid sequence comprised of complementary nucleotide base pairs.

"Cross-Sectional Cell Density" as used herein in connection with a specific cell type is the mean number of that cell type per area of cross section through a tissue in a Representative Microscopy Sample. Cross sections of the Organ of Corti can also be used to determine the number of cells in a given plane. Typically, hair cells Cross-sectional Cell Density will be measured by analyzing whole mount preparations of the Organ of Corti and counting the number of hair cells across a given distance in cross sections taken along a portion of the epithelia, as described in a Representative Microscopy Sample. Typically, Cross-sectional Cell Density of $Lgr5^+$ cells will be measured by analyzing whole mount preparations of the Organ of Corti and counting the number of $Lgr5^+$ cells across a given distance in cross sections taken along a portion of the epithelia, as described in a Representative Microscopy Sample. Hair cells may be identified by their morphological features such as bundles or hair cell specific stains (suitable stains include e.g., Myosin VIIa, Prestin, vGlut3, Pou4f3, conjugated-Phalloidin, PMCA2, Atohl, etc.). $Lgr5^+$ cells may be identified by specific stains or antibodies (suitable stains and antibodies include fluorescence in situ hybridization of Lgr5 mRNA, Lgr5-GFP transgenic reporter system, anti-Lgr5 antibodies, etc.).

"Decreasing" refers to decreasing by at least 5%, for example, 5, 6, 7, 8, 9, 10, 15, 20, 25, 30, 35, 40, 45, 50, 55, 60, 65, 70, 75, 80, 85, 90, 95, 99 or 100%, for example, as compared to the level of reference.

"Decreases" also means decreases by at least 1-fold, for example, 1, 2, 3, 4, 5, 6, 7, 8, 9, 10, 15, 20, 30, 40, 50, 60, 70, 80, 90, 100, 200, 500, 1000-fold or more, for example, as compared to the level of a reference.

"Differentiation Period" as used herein is the duration of time in which there is an Effective Stemness Driver Concentration "Effective Concentration" may be the Effective Stemness Driver Concentration for a Stemness Driver.

"Effective Release Rate" (mass/time) as used herein is the Effective Concentration (mass/volume)*30 uL/1 hour.

"Effective Stemness Driver Concentration" is the minimum concentration of a Stemness Driver that induces at least 1.5-fold increase in number of LGR5+ cells in a Stem Cell Proliferation Assay compared to the number of Lgr5+ cells in a Stem Cell Proliferation Assay performed without the Stemness Driver and with all other components present at the same concentrations.

"Eliminate" means to decrease to a level that is undetectable.

"Engraft" or "engraftment" refers to the process of stem or progenitor cell incorporation into a tissue of interest in vivo through contact with existing cells of the tissue. "Epithelial progenitor cell" refers to a multipotent cell which has the potential to become restricted to cell lineages resulting in epithelial cells.

"Epithelial stem cell" refers to a multipotent cell which has the potential to become committed to multiple cell lineages, including cell lineages resulting in epithelial cells.

"Fragment" refers to a portion of a polypeptide or nucleic acid molecule. This portion contains, at least 10%, 20%, 30%, 40%, 50%, 60%, 70%, 80%, or 90% of the entire length of the reference nucleic acid molecule or polypeptide.

A fragment may contain 10, 20, 30, 40, 50, 60, 70, 80, 90, or 100, 200, 300, 400, 500, 600, 700, 800, 900, or 1000 nucleotides or amino acids.

"Gelation Temperature," as used herein is defined as meaning the temperature below which a composition is in liquid form and above which the composition forms a semi-solid, for example, a gel.

"GSK3beta," "GSK3β," and "GSK3B" as used interchangeably herein are acronyms for glycogen synthase kinase 3 beta, "GSK3 inhibitor" is a composition that inhibits the activity of any GSK3.

"GSK3beta inhibitor" is a composition that inhibits the activity of GSK3beta.

"GSK3alpha," "GSK3a," and "GSK3A" as used interchangeably herein are acronyms for glycogen synthase kinase 3 alpha, "GSK3alpha inhibitor" is a composition that inhibits the activity of GSK3alpha.

"Hybridize" refers to pairing to form a double-stranded molecule between complementary nucleotide bases (e.g., adenine (A) forms a base pair with thymine (T), as does guanine (G) with cytosine (C) in DNA) under suitable conditions of stringency. (See, e.g., Wahl, G. M. and S. L. Berger (1987) Methods Enzymol. 152:399; Kimmel, A. R. (1987) Methods Enzymol. 152:507).

An "inhibitor" refers to an agent that causes a decrease in the expression or activity of a target gene or protein, respectively. An "antagonist" can be an inhibitor, but is more specifically an agent that binds to a receptor, and which in turn decreases or eliminates binding by other molecules.

As used herein, an "inhibitory nucleic acid" is a double-stranded RNA, RNA interference, miRNA, siRNA, shRNA, or antisense RNA, or a portion thereof, or a mimetic thereof, that when administered to a mammalian cell results in a decrease in the expression of a target gene. Typically, a nucleic acid inhibitor comprises at least a portion of a target nucleic acid molecule, or an ortholog thereof, or comprises at least a portion of the complementary strand of a target nucleic acid molecule. Typically, expression of a target gene is reduced by 10%, 25%, 50%, 75%, or even 90-100%.

"In vitro Lgr5 activity" refers to the level of expression or activity of Lgr5 in an in vitro population of cells. It may be measured, for example, in cells derived from a Lgr5-GFP expressing mouse such as a B6.129P2-Lgr5tm1(cre/ERT2) Cle/J mouse (also known as Lgr5-EGFP-IRES-creERT2 or Lgr5-GFP mouse, Jackson Lab Stock No: 008875) by dissociating cells to single cells, staining with propidium iodide (PI), and analyzing the cells using a flow cytometer for Lgr5-GFP expression. Inner ear epithelial cells from wild-type (non-Lgr5-GFP) mice that passing the same culturing and analyzing procedures can be used as a negative control. Typically, two populations of cells are shown in the bivariate plot with GFP/FITC as one variable, which include both GFP positive and GFP negative populations. Lgr5-positive cells are identified by gating GFP positive cell population. The percentage of Lgr5-positive cells is measured by gating GFP positive cell population against both GFP negative population and the negative control. The number of Lgr5-positive cells is calculated by multiplying the total number of cells by the percentage of Lgr5-positive cells. For cells derived from non-Lgr5-GFP mice, Lgr5 activity can be measured using an anti-Lgr5 antibody or quantitative-PCR on the Lgr5 gene.

"In vivo Lgr5 activity" as used herein is the level of expression or activity of Lgr5 in a subject. It may be measured, for example, by removing an animal's inner ear and measuring Lgr5 protein or Lgr5 mRNA. Lgr5 protein production can be measured using an anti-Lgr5 antibody to measure fluorescence intensity as determined by imaging cochlear samples, where fluorescence intensity is used as a measure of Lgr5 presence. Western blots can be used with an anti-Lgr5 antibody, where cells can be harvested from the treated organ to determine increases in Lgr5 protein. Quantitative-PCR or RNA in situ hybridization can be used to measure relative changes in Lgr5 mRNA production, where cells can be harvested from the inner ear to determine changes in Lgr5 mRNA. Alternatively, Lgr5 expression can be measured using an Lgr5 promoter driven GFP reporter transgenic system, where the presence or intensity GFP fluoresce can be directly detected using flow cytometry, imaging, or indirectly using an anti-GFP antibody.

"Increases" also means increases by at least 1-fold, for example, 1, 2, 3, 4, 5, 6, 7, 8, 9, 10, 15, 20, 30, 40, 50, 60, 70, 80, 90, 100, 200, 500, 1000-fold or more, for example, as compared to the level of a as compared to the level of a reference standard.

"Increasing" refers to increasing by at least 5%, for example, 5, 6, 7, 8, 9, 10, 15, 20, 25, 30, 35, 40, 45, 50, 55, 60, 65, 70, 75, 80, 85, 90, 95, 99, 100% or more, for example, as compared to the level of a reference.

"Intraauricular administration" refers to administration of a composition to the middle or inner ear of a subject by directly injecting the composition.

"Intracochlear" administration refers to direct injection of a composition across the tympanic membrane and across the round or oval window membrane into the cochlea.

"Intravestibular" administration refers to direct injection of a composition across the tympanic membrane and across the round or oval window membrane into the vestibular organs.

"Isolated" refers to a material that is free to varying degrees from components which normally accompany it as found in its native state. "Isolate" denotes a degree of separation from original source or surroundings.

"Lgr5" is an acronym for the Leucine-rich repeat-containing G-protein coupled receptor 5, also known as G-protein coupled receptor 49 (GPR49) or G-protein coupled receptor 67 (GPR67). It is a protein that in humans is encoded by the Lgr5 gene.

"Lgr5 activity" is defined as the level of activity of Lgr5 in a population of cells. In an in vitro cell population, Lgr5 activity may be measured in an in vitro Lgr5 Activity assay. In an in vivo cell population, Lgr5 activity may be measured in an in vivo Lgr5 Activity assay.

"Lgr5$^+$ cell" or "Lgr5-positive cell" as used herein is a cell that expresses Lgr5. "Lgr5$^-$ cell" as used herein is a cell that is not Lgr5$^+$.

"Lineage Tracing" as used herein is using a mouse line that enables fate tracing of any cell that expresses a target gene at the time of reporter induction. This can include hair cell or supporting cells genes (Sox2, Lgr5, MyosinVIIa, Pou4f3, etc). For example, lineage tracing may use an Lgr5-EGFP-IRES-creERT2 mouse crossed with a reporter mouse, which upon induction, allows one to trace the fate of cells that expressed Lgr5 at the time of induction. By further example, Lgr5 cells can be isolated into single cells and cultured in a Stem Cell Proliferation Assay to generate colonies, then subsequently differentiated in a Differentiation Assay and analyzed for cell fate by staining for hair cell and/or supporting cell proteins and determinning the reporter colocalization with either hair cell or supporting cell staining to determine the Lgr5 cells' fate. In addition, lineage tracing can be performed in cochlear explants to track supporting cell or hair cell fate within the intact organ after treatment. For example, Lgr5 cell fate can be determined by isolating the cochlea from a Lgr5-EGFP-IRES-creERT2 mouse crossed with a reporter mouse, and inducing the reporter in Lgr5 cells before or during treatment. The organ can then be analyzed for cell fate by staining for hair cell and/or supporting cell proteins and determinning the reporter colocalization with either hair cell or supporting cell staining to determine the Lgr5 cells' fate. In addtion, lineage tracing can be performed in vivo track supporting cell or hair cell fate within the intact organ after treatment. For example, Lgr5 cell fate can be determined inducing a reporter in an Lgr5-EGFP-IRES-creERT2 mouse crossed with a reporter mouse, treating the animal, then isolating the cochlea. The organ can then be analyzed for cell fate by staining for hair cell and/or supporting cell proteins and determinning the reporter colocalization with either hair cell or supporting cell staining to determine the Lgr5 cells' fate. Lineage tracing may be performed using alternative reporters of interest as is standard in the art.

"Mammal" refers to any mammal including but not limited to human, mouse, rat, sheep, monkey, goat, rabbit, hamster, horse, cow or pig.

"Mean Release Time" as used herein is the time in which one-half of an agent is released into phosphate buffered saline from a carrier in a Release Assay.

"Native Morphology" as used herein is means that tissue organization largely reflects the organization in a healthy tissue.

"Non-human mammal", as used herein, refers to any mammal that is not a human.

As used in relevant context herein, the term "number" of cells can be 0, 1, or more cells.

"Organ of Corti" as used herein refers to the sensory cells (inner and outer hair cells) of the hearing organ located in the cochlea.

"Organoid" or "epithelial organoid" refers to a cell cluster or aggregate that resembles an organ, or part of an organ, and possesses cell types relevant to that particular organ.

"Population" of cells refers to any number of cells greater than 1, but is at least $1\times10^3$ cells, at least $1\times10^4$ cells, at least at least $1\times10^5$ cells, at least $1\times10^6$ cells, at least $1\times10^7$ cells, at least $1\times10^8$ cells, at least $1\times10^9$ cells, or at least $1\times10^{10}$ cells.

"Progenitor cell" as used herein refers to a cell that, like a stem cell, has the tendency to differentiate into a specific type of cell, but is already more specific than a stem cell and is pushed to differentiate into its "target" cell.

"Proliferation Period" as used herein is the duration of time in which there is an Effective Stemness Driver Concentration.

"Reference" means a standard or control condition (e.g., untreated with a test agent or combination of test agents).

"Release Assay" as used herein is a test in which the rate of release of an agent from a Biocompatible Matrix through dialysis membrane to a saline environment. An exemplary Release Assay may be performed by placing 30 microliters of a composition in 1 ml Phosphate Buffered Saline inside saline dialysis bag with a suitable cutoff, and placing the dialysis bag within 10 mL of Phosphate Buffered Saline at 37 C. The dialysis membrane size may be chosen based on agent size in order to allow the agent being assessed to exit the membrane. For small molecule release, a 3.5-5 kDa cutoff may be used. The Release Rate for a composition may change over time and may be measured in 1 hour increments.

"Representative Microscopy Sample" as used herein describes a sufficient number of fields of view within a cell culture system, a portion of extracted tissue, or an entire extracted organ that the average feature size or number being measured can reasonably be said to represent the average feature size or number if all relevant fields were measured. For example, in order to assess the hair cell counts at a frequency range on the Organ of Corti, ImageJ software (NIH) can used to measure the total length of cochlear whole mounts and the length of individual counted segments. The total number of inner hair cells, outer hair cells, and supporting cells can be counted in the entire or fraction of any of the four cochlear segments of 1200-1400 µm (apical, mid-apical, mid-basal, and basal) at least 3 fields of view at 100 µm field size would be reasonably considered a Representative Microscopy Sample. A Representative Microscopy sample can include measurements within a field of view, which can be measured as cells per a given distance. A Representative Microscopy sample can be used to assess morphology, such as cell-cell contacts, cochlear architecture, and cellular components (e.g., bundles, synapses).

"Rosette Patterning" is a characteristic cell arrangement in the cochlea in which <5% hair cells are adjacent to other hair cells.

The term "sample" refers to a volume or mass obtained, provided, and/or subjected to analysis. In some embodiments, a sample is or comprises a tissue sample, cell sample, a fluid sample, and the like. In some embodiments, a sample is taken from (or is) a subject (e.g., a human or animal subject). In some embodiments, a tissue sample is or comprises brain, hair (including roots), buccal swabs, blood, saliva, semen, muscle, or from any internal organs, or cancer, precancerous, or tumor cells associated with any one of these. A fluid may be, but is not limited to, urine, blood, ascites, pleural fluid, spinal fluid, and the like. A body tissue can include, but is not limited to, brain, skin, muscle, endometrial, uterine, and cervical tissue or cancer, precancerous, or tumor cells associated with any one of these. In an embodiment, a body tissue is brain tissue or a brain tumor or cancer. Those of ordinary skill in the art will appreciate that, in some embodiments, a "sample" is a "primary sample" in that it is obtained from a source (e.g., a subject); in some embodiments, a "sample" is the result of processing of a primary sample, for example to remove certain potentially contaminating components and/or to isolate or purify certain components of interest.

"Self-renewal" refers to the process by which a stem cell divides to generate one (asymmetric division) or two (symmetric division) daughter cells with development potentials that are indistinguishable from those of the mother cell. Self-renewal involves both proliferation and the maintenance of an undifferentiated state.

"siRNA" refers to a double stranded RNA. Optimally, an siRNA is 18, 19, 20, 21, 22, 23 or 24 nucleotides in length and has a 2 base overhang at its 3' end. These dsRNAs can be introduced to an individual cell or culture system. Such siRNAs are used to downregulate mRNA levels or promoter activity.

"Stem cell" refers to a multipotent cell having the capacity to self-renew and to differentiate into multiple cell lineages.

"Stem Cell Differentiation Assay" as used herein is an assay to determine the differentiation capacity of stem cells. In an exemplary Stem Cell Differentiation Assay, the number of cells for an initial cell population is harvested from a Atoh1-GFP mouse between the age of 3 to 7 days, by isolating the Organ of Corti sensory epithelium, dissociating the epithelium into single cells, and passing the cells through a 40 um cell strainer. Approximately 5000 cells are entrapped in 40 µl of culture substrate (for example: Matrigel (Corning, Growth Factor Reduced)) and placed at the center of wells in a 24-well plate with 500 µl of an appropriate culture media, growth factors and agent being tested. Appropriate culture media and growth factors include Advanced DMEM/F12 with media Supplements (1× N2, 1× B27, 2 mM Glutamax, 10 mM HEPES, 1 mM N-acetylcysteine, and 100 U/ml Penicillin/100 µg/ml Streptomycin) and growth factors (50 ng/ml EGF, 50 ng/ml bFGF, and 50 ng/ml IGF-1) as well as the agent(s) being assessed are added into each well. Cells are cultured for 10 days in a standard cell culture incubator at 37° C. and 5% $CO_2$, with media change every 2 days. These cells are then cultured by removing the Stem Cell Proliferation Assay agents and replacing with Basal culture media and molecules to drive differentiation. An appropriate Basal culture media is Advanced DMEM/F12 supplemented with 1× N2, 1× B27, 2 mM Glutamax, 10 mM HEPES, 1 mM N-acetylcysteine, and 100 U/ml Penicillin/100 µg/ml Streptomycin and appropriate molecules to drive differentiation are 3 µM CHIR99021 and 5 µM DAPT for 10 days, with media change every 2 days. The number of hair cells in a population may be measured by using flow cytometry for GFP. Hair cell differentiation level can further be assessed using qPCR to measure hair cell marker (e.g., Myo7a) expression level normalized using suitable and unregulated references or housekeeping genes (e.g., Hprt). Hair cell differentiation level can also be assessed by immunostaining for hair cell markers (e.g.,Myosin7a, vGlut3, Espin, PMCAs, Ribeye, conjugated-phalloidin, Atoh1, Pou4f3, etc). Hair cell differentiation level can also be assessed by Western Blot for Myosin7a, vGlut3, Espin, PMCAs, Prestin, Ribeye, Atoh1, and Pou4f3.

"Stem Cell Assay" as used herein is an assay in which a cell or a cell population are tested for a series of criteria to determine whether the cell or cell population are stem cells or enriched in stem cells or stem cell markers. In a stem cell assay, the cell/cell populations are tested for stem cell characteristics such as expression of Stem Cell Markers, and further optionally are tested for stem cell function, including the capacity of self-renewal and differentiation.

"Stem Cell Proliferator" as used herein is a composition that induces an increase in a population of cells which have the capacity for self-renewal and differentiation.

"Stem Cell Proliferation Assay" as used herein is an assay to determine the capacity for agent(s) to induce the creation of stem cells from a starting cell population. In an exemplary Stem Cell Proliferation Assay, the number of cells for an initial cell population is harvested from a Lgr5-GFP mouse such as a B6.129P2-Lgr5tm1(cre/ERT2)Cle/J mouse (also known as Lgr5-EGFP-IRES-creERT2 or Lgr5-GFP mouse, Jackson Lab Stock No: 008875) between the age of 3 to 7 days, by isolating the Organ of Corti sensory epithelium and dissociating the epithelium into single cells. Approximately 5000 cells are entrapped in 40 µl of culture substrate (for example: Matrigel (Corning, Growth Factor Reduced)) and placed at the center of wells in a 24-well plate with 500 µl of an appropriate culture media, growth factors and agent being tested. Appropriate culture media and growth factors include Advanced DMEM/F12 with media Supplements (1× N2, 1× B27, 2 mM Glutamax, 10 mM HEPES, 1 mM N-acetylcysteine, and 100 U/ml Penicillin/100 µg/ml Streptomycin) and growth factors (50 ng/ml EGF, 50 ng/ml bFGF, and 50 ng/ml IGF-1) as well as the agent(s) being assessed are added into each well. Cells are cultured for 10 days in a standard cell culture incubator at 37° C. and 5% $CO_2$, with media change every 2 days. The number of $Lgr5^+$ cells is quantified by counting the number of cells identified as Lgr5+ in an In vitro Lgr5 activity assay. The fraction of cells that are $Lgr5^+$ is quantified by dividing the number of cells identified as $Lgr5^+$ in a cell population by the total number of cells present in the cell population. The average $Lgr5^+$ activity of a population is quantified by measuring the average mRNA expression level of Lgr5 of the population normalized using suitable and unregulated references or housekeeping genes (e.g., Hprt). The number of hair cells in a population may be measured by staining with hair cell marker (e.g., Myosin VIIa), or using an endogenous reporter of hair cell genes (e.g.,Pou4f3-GFP, Atoh1-nGFP) and analyzing using flow cytometry. The fraction of cells that are hair cells is quantified by dividing the number of cells identified as hair cells in a cell population by the total number of cells present in the cell population. Lgr5 activity can be measured by qPCR.

"Stem Cell Markers" as used herein can be defined as gene products (e.g., protein, RNA, etc) that specifically expressed in stem cells. One type of stem cell marker is gene products that are directly and specifically support the maintenance of stem cell identity. Examples include Lgr5 and Sox2. Additional stem cell markers can be identified using assays that have been described in the literature. To determine whether a gene is required for maintenance of stem cell identity, gain-of-function and loss-of-function studies can be used. In gain-of-function studies, over expression of specific gene product (the stem cell marker) would help maintain the stem cell identity. While in loss-of-function studies, removal of the stem cell marker would cause loss of the stem cell identity or induced the differentiation of stem cells. Another type of stem cell marker is gene that only expressed in stem cells but does not necessary to have specific function to maintain the identity of stem cells. This type of markers can be identified by comparing the gene expression signature of sorted stem cells and non-stem cells by assays such as micro-array and qPCR. This type of stem cell marker can be found in the literature. (e.g., Liu Q. et al., *Int J Biochem Cell Biol*. 2015 March; 60:99-111. http://www.ncbi.nlm.nih.gov/pubmed/25582750). Potential stem cell markers include Ccdc121, Gdf10, Opcm1, Phex, etc. The expression of stem cell markers such as Lgr5 or Sox2 in a given cell or cell population can be measure using assays such as qPCR, immunohistochemistry, western blot, and RNA hybridization. The expression of stem cell markers can also be measured using transgenic cells express reporters which can indicate the expression of the given stem cell markers, e.g., Lgr5-GFP or Sox2-GFP. Flow cytometry analysis can then be used to measure the activity of reporter expression. Fluorescence microscopy can also be used to directly visualize the expression of reporters. The expression of stem cell markers may further be determined using microarray analysis for global gene expression profile analysis. The gene expression profile of a given cell population or purified cell population can be compared with the gene expression profile of the stem cell to determine similarity between the 2 cell populations. Stem cell function can be measured by colony forming assay or sphere forming assay, self-renewal assay and differentiation assay. In colony (or sphere) forming assay, when cultured in appropriate culture media, the stem cell should be able to form colonies, on cell culture surface (e.g., cell culture dish) or embedded in cell culture substrate (e.g., Matrigel) or be able to form spheres when cultured in suspension. In colony/sphere forming assay, single stem cells are seeded at low cell density in appropriate culture media and allowed to proliferate for a given period of time (7-10 days). Colony formed are then counted and scored for stem cell marker expression as an indicator of stemness of the original cell. Optionally, the colonies that formed are then picked and passaged to test its self-renewal and differentiation potential. In self-renewal assay, when cultured in appropriate culture media, the cells should maintain stem cell marker (e.g., Lgr5) expression over at least one (e.g., 1, 2, 3, 4, 5, 10, 20, etc) cell divisions. In a Stem Cell Differentiation Assay, when cultured in appropriate differentiation media, the cells should be able to generate hair cell which can be identified by hair cell marker expression measured by qPCR, immunostaining, western blot, RNA hybridization or flow cytometry.

"Stemness Driver" as used herein is a composition that induces proliferation of $LGR5^+$ cells, upregulates Lgr5 in cells, or maintains Lgr5 expression in cells, while maintaining the potential for self-renewal and the potential to differentiate into hair cells. Generally, stemness drivers upregulate at least one biomarker of post-natal stem cells. Stemness Drivers include but are not limited to Wnt agonists and GSK3Beta inhibitors.

"Subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

"Supporting Cell" as used herein in connection with a cochlear epithelium comprises epithelial cells within the organ of Corti that are not hair cells. This includes inner pillar cells, outer pillar cells, inner phalangeal cells, Deiter cells, Hensen cells, Boettcher cells, and/or Claudius cells.

"Synergy" or "synergistic effect" is an effect which is greater than the sum of each of the effects taken separately; a greater than additive effect.

"TgfBeta inhibitor" as used herein is a composition that reduces activity of TgfB eta "Thermoreversible gel" means a material that reversibly changes from a liquid to a gel with a change in temperature.

"Tissue" is an ensemble of similar cells from the same origin that together carries out a specific function including, for example, tissue of cochlear, such as the Organ of Corti.

"Transtympanic" administration refers to direct injection of a composition across the tympanic membrane into the middle ear.

"Treating" as used herein in connection with a cell population means delivering a substance to the population to effect an outcome. In the case of in vitro populations, the substance may be directly (or even indirectly) delivered to the population. In the case of in vivo populations, the substance may be delivered by administration to the host subject.

"Valproic acid" (VPA) has chemical formula $C_8E11602$ and the following alternate name: 2-propylpentanoic acid. Its chemical structure is as follows:

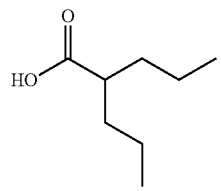

As used herein, the term "Valproic acid" also includes derivatives of Valproic Acid including its salts, amides, prodrugs and esters.

"Wnt activation" as used herein in connection with a composition is an activation of the Wnt signaling pathway.

The use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical compositions.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, /toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. For example, inorganic salts include, but are not limited to, ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Non-limiting examples of organic bases used in certain embodiments include isopropylamine, diethylamine, ethanolamine, trimethylamine, dicyclohexylamine, choline and caffeine.

"w/w" refers to the ratio of reagents in a composition measured using the weight of the reagent in grams, milligrams, or kilograms.

"wt %" refers to the percent of that agent in the composition measured using the weight of the agent measured in grams, milligrams, or kilograms.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

One aspect the present disclosure provides a poloxamer containing pharmaceutical composition having a gelation temperature greater than 10° C., the composition comprising:

a) a pharmaceutically active therapeutic agent or a pharmaceutically acceptable salt thereof;
b) a poloxamer at greater than or equal to 21 wt % of the pharmaceutical composition; and
c) a carboxylic acid containing compound;
wherein the pharmaceutical composition to have a gelation temperature of greater than 10° C.

In some embodiments, the poloxamer comprises at least one of Poloxamer 124, Poloxamer 188, Poloxamer 237, Poloxamer 338 or Poloxamer 407. In some embodiments, the poloxamer comprises mixtures of two or more of Poloxamer 124, Poloxamer 188, Poloxamer 237, Poloxamer 338 or Poloxamer 407. In some embodiments, the mixture of two or more poloxamers comprises Poloxamer 407 and Poloxamer 124. In another embodiment, the Poloxamer comprises at least one of Poloxamer 188 and Poloxamer 407 or mixtures thereof. In some embodiments, the poloxamer is Poloxamer 407.

In some embodiments, the poloxamer can be in a concentration between 21 wt % and 40 wt % relative to the composition. In another embodiment, the poloxamer is in a concentration between 21 wt % and 30 wt % relative to the composition. In another embodiment, the poloxamer is in a concentration between 23 wt % and 29 wt % relative to the composition. In another embodiment, the poloxamer is in a concentration between 23 wt % and 27 wt % relative to the composition. In another embodiment, the poloxamer is in a concentration of 25 wt % relative to the composition.

In some embodiments, the gelation temperature of the pharmaceutical composition is between about 11° C. and about 32° C. In some embodiments, the gelation temperature of the pharmaceutical composition is between is between about 15° C. and about 30° C. In some embodiments, the gelation temperature of the pharmaceutical composition is between about 20° C. and about 28° C. In some embodiments, the gelation temperature of the pharmaceutical composition is between about 24° C. and about 26° C. In some embodiments, the gelation temperature of the pharmaceutical composition is about 15° C. In some embodiments, the gelation temperature of the pharmaceutical composition is about 20° C. In some embodiments, the gelation temperature of the pharmaceutical composition is about 24° C. In some embodiments, the gelation temperature of the pharmaceutical composition is about 26° C. In some embodiments, the gelation temperature of the pharmaceutical composition is about 28° C. In some embodiments, the gelation temperature of the pharmaceutical composition is about 30° C. In some embodiments, the gelation temperature of the pharmaceutical composition is about 32° C.

In any of the foregoing embodiments, the carboxylic acid containing compound is a substituted or unsubstituted $C_5$-$C_9$ straight or branched chain alkyl-$CO_2H$.

In any of the foregoing embodiments, the carboxylic acid containing compound is a substituted $C_5$-$C_9$ straight or branched chain alkyl-$CO_2H$.

In some embodiments, the carboxylic acid containing compound is a substituted $C_5$-$C_9$ straight or branched chain alkyl-$CO_2H$, wherein the substituent is —$NH_2$. In some examples the carboxylic acid containing compound is an amino substituted 2-propylpentanoic acid. In some embodiments, the amino substituted 2-propylpentanoic acid is selected from the group consisting of 5-amino-2-propylpentanoic acid, 4-amino-2-propylpentanoic acid, 3-amino-2-propylpentanoic acid, and 2-amino-2-propylpentanoic acid.

In some embodiments, the carboxylic acid containing compound is an unsubstituted $C_5$-$C_9$ straight or branched chain alkyl-$CO_2H$.

In some embodiments, the carboxylic acid containing compound is an unsubstituted $C_6$-$C_9$ branched straight chain alkyl-$CO_2H$.

In some embodiments, the carboxylic acid containing compound is an unsubstituted $C_8$-$C_9$ branched straight chain alkyl-$CO_2H$.

In some embodiments, the carboxylic acid containing compound is an unsubstituted $C_9$ branched straight chain alkyl-$CO_2H$.

In some embodiments, the unsubstituted $C_9$ branched straight chain alkyl-$CO_2H$ carboxylic acid containing compound is Valproic acid.

In some embodiments, the Valproic acid can be in the form of an amide.

In some embodiments, the amide form of Valproic acid is the condensation product with an amino acid. In some embodiments, the amide of Valproic acid is selected from the group consisting of

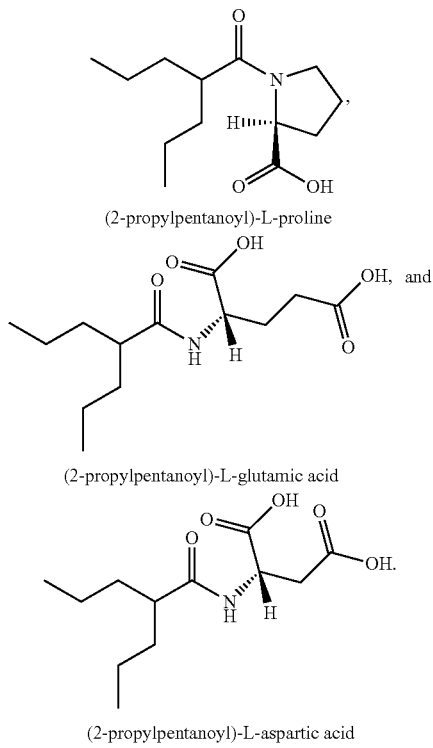

(2-propylpentanoyl)-L-proline (2-propylpentanoyl)-L-glutamic acid (2-propylpentanoyl)-L-aspartic acid In any of the foregoing embodiments, the amount of the carboxylic acid containing compound in the pharmaceutical composition is between at least 2 wt % (weight carboxylic acid containing compound/weight pharmaceutical composition) and 20 wt %. In some embodiments, the composition comprises at least 4 wt % carboxylic acid. In other embodiments, the composition comprises at least 8 wt % carboxylic acid. In some embodiments, the composition comprises at least 12 wt % carboxylic acid. In some embodiments, the composition comprises at least 16 wt % carboxylic acid. In still other embodiments, the composition comprises at least 20 wt % carboxylic acid.

In other embodiments, the composition comprises about 4 wt % carboxylic acid. In other embodiments, the composition comprises about 8 wt % carboxylic acid. In other embodiments, the composition comprises about 12 wt % carboxylic acid. In further embodiments, the composition comprises about 16 wt % carboxylic acid. In further embodiments, the composition comprises about 20 wt % carboxylic acid.

In some embodiments of the poloxamer containing pharmaceutical composition, the pharmaceutically active therapeutic agent is selected from the group consisting of a wnt agonist, a GSK3 inhibitor, a 2-pyrimidinylaminoethylamino-2-pyridine containing compound, a N-(1H-pyrazol-4-yl)-nicotinamide containing compound, and a 1,2,3,4-tetrahydro-[1,4]diazepino[6,7]indol-7-yl)-4-(imidazo[1,2-a]pyridin-3-yl)-1H-pyrrole-2,5-dione containing compound.

A further aspect of the present disclosure provides a poloxamer containing pharmaceutical composition having a gelation temperature greater than 10° C., the composition comprising a) a wnt agonist or a pharmaceutically acceptable salt thereof;

b) Poloxamer 407 at greater than or equal to 21 wt % of the pharmaceutical composition; and c) a carboxylic acid containing compound;

wherein the pharmaceutical composition has a gelation temperature of greater than 10° C.

In some embodiments, the wnt agonist is selected from the group consisting of

| WNT Agonists | CAS Number |
| --- | --- |
| Compound 1 | 1084833-94-2 |
| Compound 25 | 1084834-05-8 |
| BML-284 | 853220-52-7 |
| IQ 1 | 331001-62-8 |
| DCA | 56-47-3 |
| QS 11 | 944328-88-5 |
| WASP-1, ZINC00087877 | 352328-82-6 |
| WAY 316606 | 915759-45-4 |
| WAY-262611 | 1123231-07-1 |
| HLY78 | 854847-61-3 |
| SKL2001 | 909089-13-0 |

In other embodiments, the wnt agonist is selected from the group consisting of the Compound 1, Compound 25, BML-284, QS-11, WAY 316606, WAY-262611, SKL2001, and ISX-9.

In some embodiments, Poloxamer 407 can be in a concentration between 21 wt % and 40 wt % relative to the composition. In another embodiment, the Poloxamer 407 is in a concentration between 21 wt % and 30 wt % relative to the composition. In another embodiment, the Poloxamer 407 is in a concentration between 23 wt % and 29 wt % relative to the composition. In another embodiment, the Poloxamer 407 is in a concentration between 23 wt % and 27 wt % relative to the composition. In another embodiment, the Poloxamer 407 is in a concentration of 25 wt % relative to the composition.

In some embodiments, the gelation temperature of the pharmaceutical composition is between about 11° C. and about 32° C. In some embodiments, the gelation temperature of the pharmaceutical composition is between is between about 15° C. and about 30° C. In some embodiments, the gelation temperature of the pharmaceutical composition is between about 20° C. and about 28° C. In some embodiments, the gelation temperature of the pharmaceutical composition is between about 24° C. and about 26° C. In some embodiments, the gelation temperature of the pharmaceutical composition is about 15° C. In some embodiments, the gelation temperature of the pharmaceutical composition is about 20° C. In some embodiments, the gelation temperature of the pharmaceutical composition is about 24° C. In some embodiments, the gelation temperature of the pharmaceutical composition is about 26° C. In some embodiments, the gelation temperature of the pharmaceutical composition is about 28° C. In some embodiments, the gelation temperature of the pharmaceutical composition is about 30° C. In some embodiments, the gelation temperature of the pharmaceutical composition is about 32° C.

In any of the foregoing embodiments, the carboxylic acid containing compound is a substituted or unsubstituted $C_5$-$C_9$ straight or branched chain alkyl-$CO_2H$.

In any of the foregoing embodiments, the carboxylic acid containing compound is a substituted $C_5$-$C_9$ straight or branched chain alkyl-$CO_2H$.

In some embodiments, the carboxylic acid containing compound is a substituted $C_5$-$C_9$ straight or branched chain alkyl-$CO_2H$, wherein the substituent is —$NH_2$. In some examples the carboxylic acid containing compound is an amino substituted 2-propylpentanoic acid. In some embodiments, the amino substituted 2-propylpentanoic acid is selected from the group consisting of 5-amino-2-propylpentanoic acid, 4-amino-2-propylpentanoic acid, 3-amino-2-propylpentanoic acid, and 2-amino-2-propylpentanoic acid.

In some embodiments, the carboxylic acid containing compound is an unsubstituted $C_5$-$C_9$ straight or branched chain alkyl-$CO_2H$.

In some embodiments, the carboxylic acid containing compound is an unsubstituted $C_6$-$C_9$ branched straight chain alkyl-$CO_2H$.

In some embodiments, the carboxylic acid containing compound is an unsubstituted $C_8$-$C_9$ branched straight chain alkyl-$CO_2H$.

In some embodiments, the carboxylic acid containing compound is an unsubstituted $C_9$ branched straight chain alkyl-$CO_2H$.

In some embodiments, the unsubstituted $C_9$ branched straight chain alkyl-$CO_2H$ carboxylic acid containing compound is Valproic acid.

In some embodiments, the Valproic acid can be in the form of an amide. In some embodiments, the amide form of Valproic acid is the condensation product with an amino acid.

In some embodiments, the amide of Valproic acid is selected from the group consisting of

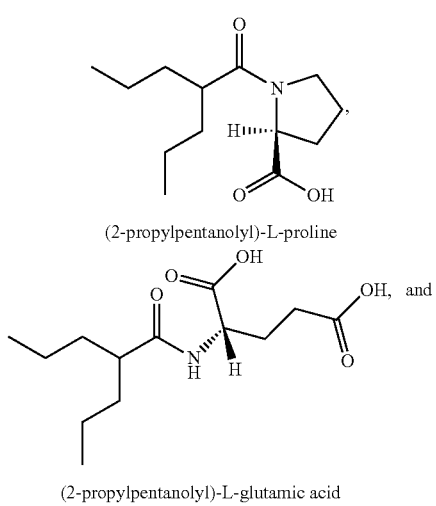

(2-propylpentanolyl)-L-proline (2-propylpentanolyl)-L-glutamic acid

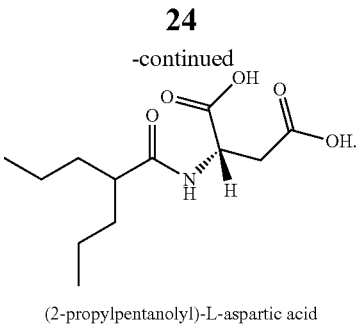

(2-propylpentanolyl)-L-aspartic acid

In any of the foregoing embodiments, the amount of the carboxylic acid containing compound in the pharmaceutical composition is between at least 2 wt % (weight carboxylic acid containing compound/weight pharmaceutical composition) and 20 wt %. In some embodiments, the composition comprises at least 4 wt % carboxylic acid. In other embodiments, the composition comprises at least 8 wt % carboxylic acid. In some embodiments, the composition comprises at least 12 wt % carboxylic acid. In some embodiments, the composition comprises at least 16 wt % carboxylic acid. In still other embodiments, the composition comprises at least 20 wt % carboxylic acid.

In other embodiments, the composition comprises about 4 wt % carboxylic acid. In other embodiments, the composition comprises about 8 wt % carboxylic acid. In other embodiments, the composition comprises about 12 wt % carboxylic acid. In further embodiments, the composition comprises about 16 wt % carboxylic acid. In further embodiments, the composition comprises about 20 wt % carboxylic acid.

A further aspect of the present disclosure provides a poloxamer containing pharmaceutical composition having a gelation temperature greater than 10° C., the composition comprising:
a) a GSK3 inhibitor or a pharmaceutically acceptable salt thereof;
b) Poloxamer 407 at greater than or equal to 21 wt % of the pharmaceutical composition; and
c) a carboxylic acid containing compound;
wherein the pharmaceutical composition has a gelation temperature of greater than 10° C.

In some embodiments, the pharmaceutically active therapeutic agent is a GSK3 inhibitor. In some embodiments, the GSK3 inhibitor is a GSK3 alpha inhibitor. In some embodiments, the GSK alpha inhibitor is selected from the group consisting of

| GSKalpha inhibitor | CAS Number |
|---|---|
| GSK-3 inhibitor XXII | 1195901-31-5 |
| AT 7519 | 844442-38-2 |
| Compound 4a | 1627557-91-8 |
| Compound 4t | 1627558-10-4 |
| Compound 4z | 1627558-16-0 |
| Compound 14 | 583038-63-5 |
| Compound 23 | 583038-76-0 |
| Pyrazolopyridine 34 | 583039-27-4 |
| Compound 18 | 405223-20-3 |
| Compound 19 | 405223-71-4 |
| Compound 15b | 1374671-66-5 |
| Compound 14d | 1374671-64-3 |
| Compound 27 | 1820758-44-8 |
| AZD1080 | 612487-72-6 |
| Compound 39 | 1772824-10-8 |
| Compound 29 | 1772823-37-6 |
| Compound 33 | 1772823-64-9 |

| GSKalpha inhibitor | CAS Number |
|---|---|
| Tivantinib | 905854-02-6 |
| I5 | 264217-24-5 |
| Compound 90 | 91322-11-1 |
| Compound 92 | 1043429-30-6 |
| Compound Λ-OS1 | 1291104-51-2 |
|  | 1292843-11-8 |
| Compound 3 | 1498285-39-4 |
|  | 1498285-48-5 |
| Compound (R)-DW12 | 1047684-07-0 |
| BRD4003 chiral | 1597439-60-5 |
| BRD4003 chiral | 1597439-59-2 |
| Compound 8 | 1597439-01-4 |
| Compound 9 | 1597439-02-5 |
|  | 2056261-29-9 |
| Compound 11 | 1597439-12-7 |
| BRD1172 | 1597438-86-2 |
| Compound 16 | 1597440-17-9 |
| BRD1652 | 1597438-93-1 |
| AR-A014418 | 487021-52-3 |
| CREB knockdown |  |

In some embodiments, the GSK3-alpha inhibitors are selected from the group consisting of GSK-alpha Inhibitor XXII, Compound 4a, Compound 4t, Compound 4z, Compound 14, Compound 23, Compound 18, Compound 19, Compound 15b, Compound 14d, AZD-1080, Compound 39, Compound 29, Compound 33, Compound 92, and Compound A-OS1

In some embodiments, the pharmaceutically active therapeutic agent is a GSK3 inhibitor is a GSK3 beta inhibitor.

In some embodiments, the GSK3 Inhibitor is selected from the group consisting of:

| GSK3β Inhibitor | CAS Reg. No. |
|---|---|
| Valproic Acid, Sodium Salt | 99-66-1 |
| Bikinin | 188011-69-0 |
| Hymenialdisine | 82005-12-7 |
| Aloisine A | 496864-16-5 |
| Aloisine B | 496864-14-3 |
| TWS119 | 1507095-58-0 |
| CT20026 | 403808-63-9 |
| CHIR99021 (CT99021) | 252917-06-9 |
| CHIR98014 (CT98014) | 252935-94-7 |
| CHIR98023 (CT98023) | 252904-84-0 |
| CHIR98024 (CT98024) | 556813-39-9 |
| GSK-3β Inhibitor XVIII | 1139875-74-3 |
| CGP60474 | 164658-13-3 |
| AZD2858 (AR28) | 486424-20-8 |
| CID 755673 | 521937-07-5 |
| TCS 2002 | 1005201-24-0 |
| Dibromocantharelline | 101481-34-9 |
| ML320 | 1597438-84-0 |
| Flavopiridol | 146426-40-6 |
| Compound 100 | 744255-19-4 |
| Hymenidin | 107019-95-4 |
| 6-Bromoindirubin-3-acetoxime | 667463-85-6 |
| GSK-3 Inhibitor IX | 667463-62-9 |
| Indirubin-3'-monoxime | 160807-49-8 |
| 5-Iodo-indirubin-3'-monoxime | 331467-03-9 |
| Indirubin-5-sulfonic acid sodium salt | 331467-05-1 |
| Indirubin | 479-41-4 |
| GSK-3 Inhibitor X | 740841-15-0 |
| Lithium Chloride |  |
| Beryllium |  |
| Zinc |  |
| Tungstate |  |
| Compound 39 | 1772824-10-8 |
| Compound 29 | 1772823-37-6 |
| Compound 33 | 1772823-64-9 |
| Compound 29 | 436866-61-4 |
| Compound 46 | 682807-74-5 |
| Compound 5a | 436866-54-5 |
| GF109203x | 176504-36-2 |
| Ro318220 | 125314-64-9 |
| Bisindolylmaleimide X HCl | 131848-97-0 |
| Enzastaurin (LY317615) | 170364-57-5 |
| I5 | 264217-24-5 |
| SB-216763 | 280744-09-4 |
| SB-415286 (SB-41528) | 264218-23-7 |
| 3F8 | 159109-11-2 |
| TCS 21311 | 1260181-14-3 |
| GSK-3 inhibitor 1 | 603272-51-1 |
| LY2090314 | 603288-22-8 |
| 603281-31-8 | 603281-31-8 |
| IM-12 | 1129669-05-1 |
| Compound 34 | 396091-16-0 |
| KT 5720 | 108068-98-0 |
| Isogranulatimide | 244148-46-7 |
| GSK-3β Inhibitor XI | 626604-39-5 |
| BIP-135 | 941575-71-9 |
| CP21R7 | 125314-13-8 |
| Tivantinib | 905854-02-6 |
| Compound Λ-OS1 | 1291104-51-2, |
|  | 1292843-11-8 |
| HB12 | 800384-87-6 |
| DW12 | 861251-33-4 |
| NP309 | 937810-13-4 |
| (RRu)-HB1229 |  |
| (RRu)-NP549 |  |
| Compound 3 | 1498285-39-4, |
|  | 1498285-48-5 |
| Compound (R)-DW12 | 1047684-07-0 |
| Staurosporine | 62996-74-1 |
| GSK-3beta Inhibitor XXVI | 871843-09-3 |
| Manzamine A | 104196-68-1 |
| TC-G 24 | 1257256-44-2 |
| Compound 14d | 1374671-64-3 |
| Compound 15b | 1374671-66-5 |
| Compound 20x | 1005201-80-8 |
| GSK-3 Inhibitor II | 478482-75-6 |
| GSK3 Inhibitor, 2 | 1377154-01-2 |
| SU9516 | 77090-84-1 |
| AZD-1080 | 612487-72-6 |
| Kenpaullone | 142273-20-9 |
| Compound 17b | 408532-42-3 |
| Azakenpaullone | 676596-65-9 |
| Alsterpaullone | 237430-03-4 |
| Alsterpaullone CN Ethyl | 852529-97-0 |
| Cazpaullone | 914088-64-5 |
| FRATtide |  |
| L803 |  |
| L803-mts |  |
| GSK-3 Inhibitor XXII | 1195901-31-5 |
| Compound 4a | 1627557-91-8 |
| Compound 4t | 1627558-10-4 |
| Compound 4z | 1627558-16-0 |
| AT 7519 | 844442-38-2 |
| Pyrazolopyridine 9 | 923029-74-7 |
| Pyrazolopyridine 18 | 405221-39-8 |
| Pyrazolopyridine 34 | 583039-27-4 |
| Compound 14 | 583038-63-5 |
| Compound 23 | 583038-76-0 |
| Compound 14 | 583038-63-5 |
| Compound 18 | 405223-20-3 |
| Compound 19 | 405223-71-4 |
| NSC 693868 (Compound 1) | 40254-90-8 |
| Compound 150 | 1282042-18-5 |
| GSK-3 Inhibitor XIII | 404828-08-6 |
| VP0.7 | 331963-23-6 |
|  | 1132813-46-7 |
|  | 1132812-98-6 |
|  | 950727-66-9 |
| NSC 693868 (Compound 1) | 40254-90-8 |
| Compound 17 | 62673-69-2 |
| GSK-3β Inhibitor VII | 99-73-0 |
| GSK-3β Inhibitor VI | 62673-69-2 |
| Palinurin | 254901-27-4 |
| Tricantin | 853885-55-9 |
| GSK-3β Inhibitor I | 327036-89-5 |

-continued

| GSK3β Inhibitor | CAS Reg. No. |
|---|---|
| NP031115 | 1400575-57-6 |
| NP031112 (Tideglusib) | 865854-05-3 |
| Compound 90 | 91322-11-1 |
| Compound 92 | 1043429-30-6 |
| GSK-3β Inh. VIII AR-A014418 | 487021-52-3 |
| A-1070722 | 1384424-80-9 |
| NP-103 | No Structure |
| CG-301338 | No Structure |
| SAR 502250 | No Structure |
| XD-4241 | No Structure |
| CEP-16805 | No Structure |
| AZ13282107 | No Structure |
| SAR 502250 (Sanofi) | 1073653-58-3 |
| Compound 27 | 2025388-25-2 |
| Compound 12 | 2025388-10-5 |

In certain embodiments, the GSK3β Inhibitor are selected from the group consisting of Valproic Acid Sodium Salt, CT20026, CHIR99021 (CT99021), CHIR98014 (CT98014), CHIR98023 (CT98023), CHIR98024 (CT98024), TCS 2002, Compound 39, Compound 29, Compound 33, TCS 21311, LY2090314, 603281-31-8, Compound 34, Compound 14d, Compound 15b, Compound 20x, AZD-1080, Kenpaullone, Cazpaullone, GSK-3 Inhibitor XXII, Compound 4a, Compound 4t, Compound 4z, Pyrazolopyridine 9, Compound 14, Compound 23, Compound 14, Compound 18, and Compound 19.

In certain embodiments, the GSK3β Inhibitor are selected from the group consisting of Valproic Acid Sodium Salt, CHIR99021 (CT99021), CHIR98014 (CT98014), CHIR98023 (CT98023), CHIR98024 (CT98024), Compound 39, Compound 29, LY2090314, 603281-31-8, Compound 34, Compound 14d, Compound 15b, Compound 20x, AZD-1080, Cazpaullone, GSK-3 Inhibitor XXII, Compound 4t, Compound 4z, Pyrazolopyridine 9, Compound 14, Compound 23, Compound 14, Compound 18, and Compound 19.

In some embodiments, the Poloxamer 407 can be in a concentration between 21 wt % and 40 wt % relative to the composition. In another embodiment, the Poloxamer 407 is in a concentration between 21 wt % and 30 wt % relative to the composition. In another embodiment, the Poloxamer 407 is in a concentration between 23 wt % and 29 wt % relative to the composition. In another embodiment, the Poloxamer 407 is in a concentration between 23 wt % and 27 wt % relative to the composition. In another embodiment, the Poloxamer 407 is in a concentration of 25 wt % relative to the composition.

In some embodiments, the gelation temperature of the pharmaceutical composition is between about 11° C. and about 32° C. In some embodiments, the gelation temperature of the pharmaceutical composition is between is between about 15° C. and about 30° C. In some embodiments, the gelation temperature of the pharmaceutical composition is between about 20° C. and about 28° C. In some embodiments, the gelation temperature of the pharmaceutical composition is between about 24° C. and about 26° C. In some embodiments, the gelation temperature of the pharmaceutical composition is about 15° C. In some embodiments, the gelation temperature of the pharmaceutical composition is about 20° C. In some embodiments, the gelation temperature of the pharmaceutical composition is about 24° C. In some embodiments, the gelation temperature of the pharmaceutical composition is about 26° C. In some embodiments, the gelation temperature of the pharmaceutical composition is about 28° C. In some embodiments, the gelation temperature of the pharmaceutical composition is about 30° C. In some embodiments, the gelation temperature of the pharmaceutical composition is about 32° C.

In any of the foregoing embodiments, the carboxylic acid containing compound is a substituted or unsubstituted $C_5$-$C_9$ straight or branched chain alkyl-$CO_2H$.

In any of the foregoing embodiments, the carboxylic acid containing compound is a substituted $C_5$-$C_9$ straight or branched chain alkyl-$CO_2H$.

In some embodiments, the carboxylic acid containing compound is a substituted $C_5$-$C_9$ straight or branched chain alkyl-$CO_2H$, wherein the substituent is —$NH_2$. In some examples the carboxylic acid containing compound is an amino substituted 2-propylpentanoic acid. In some embodiments, the amino substituted 2-propylpentanoic acid is selected from the group consisting of 5-amino-2-propylpentanoic acid, 4-amino-2-propylpentanoic acid, 3-amino-2-propylpentanoic acid, and 2-amino-2-propylpentanoic acid.

In some embodiments, the carboxylic acid containing compound is an unsubstituted $C_5$-$C_9$ straight or branched chain alkyl-$CO_2H$.

In some embodiments, the carboxylic acid containing compound is an unsubstituted $C_6$-$C_9$ branched straight chain alkyl-$CO_2H$.

In some embodiments, the carboxylic acid containing compound is an unsubstituted $C_8$-$C_9$ branched straight chain alkyl-$CO_2H$.

In some embodiments, the carboxylic acid containing compound is an unsubstituted $C_9$ branched straight chain alkyl-$CO_2H$.

In some embodiments, the unsubstituted $C_9$ branched straight chain alkyl-$CO_2H$ carboxylic acid containing compound is Valproic acid.

In some embodiments, the Valproic acid can be in the form of an amide. In some embodiments, the amide form of Valproic acid is the condensation product with an amino acid. In some embodiments, the amide of Valproic acid is selected from the group consisting of

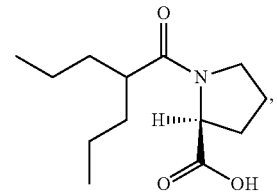

(2-propylpentanolyl)-L-proline

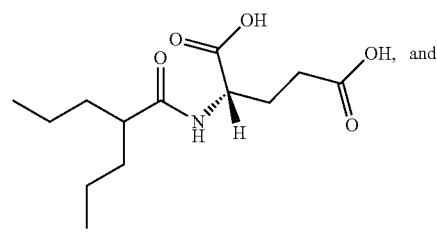

(2-propylpentanolyl)-L-glutamic acid

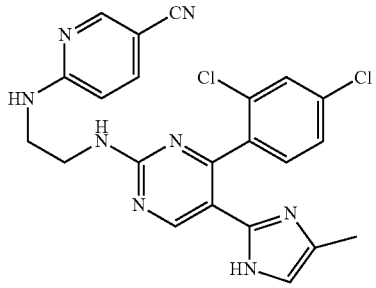

(2-propylpentanolyl)-L-aspartic acid

In any of the foregoing embodiments, the amount of the carboxylic acid containing compound in the pharmaceutical composition is between at least 2 wt % (weight carboxylic acid containing compound/weight pharmaceutical composition) and 20 wt %. In some embodiments, the composition comprises at least 4 wt % carboxylic acid. In other embodiments, the composition comprises at least 8 wt % carboxylic acid. In some embodiments, the composition comprises at least 12 wt % carboxylic acid. In some embodiments, the composition comprises at least 16 wt % carboxylic acid. In still other embodiments, the composition comprises at least 20 wt % carboxylic acid.

In other embodiments, the composition comprises about 4 wt % carboxylic acid. In other embodiments, the composition comprises about 8 wt % carboxylic acid. In other embodiments, the composition comprises about 12 wt % carboxylic acid. In further embodiments, the composition comprises about 16 wt % carboxylic acid. In further embodiments, the composition comprises about 20 wt % carboxylic acid.

A further aspect of the present disclosure provides a poloxamer containing pharmaceutical composition having a gelation temperature greater than 10° C., the composition comprising:

a) a 2-pyrimidinylaminoethylamino-2-pyridine compound;
b) Poloxamer 407 at greater than or equal to 21 wt % of the pharmaceutical composition; and
c) a carboxylic acid containing compound;

wherein the pharmaceutical composition has a gelation temperature of greater than 10° C.

In some embodiments, the 2-pyrimidinylaminoethylamino-2-pyridine compound is a 2,4-dichlorophenyl-5-(1H-imidazol-2-yl)-2-pyrimidinylaminoethylamino-3-pyridine compound. In some embodiments, the pyrimidine containing compound is 6-[[2-[[4-(2,4-Dichlorophenyl)-5-(5-methyl-1H-imidazol-2-yl)-2-pyrimidinyl]amino]ethyl]amino]-3-pyridinecarbonitrile which has the Formula I and pharmaceutically acceptable salts thereof:

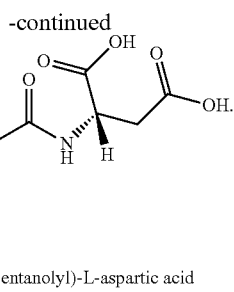

Formula I

The compound of Formula I is also known as CHIR99021.

In some embodiments, the Poloxamer 407 can be in a concentration between 21 wt % and 40 wt % relative to the composition. In another embodiment, the Poloxamer 407 is in a concentration between 21 wt % and 30 wt % relative to the composition. In another embodiment, the Poloxamer 407 is in a concentration between 23 wt % and 29 wt % relative to the composition. In another embodiment, the Poloxamer 407 is in a concentration between 23 wt % and 27 wt % relative to the composition. In another embodiment, the Poloxamer 407 is in a concentration of 25 wt % relative to the composition.

In some embodiments, the gelation temperature of the pharmaceutical composition is between about 11° C. and about 32° C. In some embodiments, the gelation temperature of the pharmaceutical composition is between is between about 15° C. and about 30° C. In some embodiments, the gelation temperature of the pharmaceutical composition is between about 20° C. and about 28° C. In some embodiments, the gelation temperature of the pharmaceutical composition is between about 24° C. and about 26° C. In some embodiments, the gelation temperature of the pharmaceutical composition is about 15° C. In some embodiments, the gelation temperature of the pharmaceutical composition is about 20° C. In some embodiments, the gelation temperature of the pharmaceutical composition is about 24° C. In some embodiments, the gelation temperature of the pharmaceutical composition is about 26° C. In some embodiments, the gelation temperature of the pharmaceutical composition is about 28° C. In some embodiments, the gelation temperature of the pharmaceutical composition is about 30° C. In some embodiments, the gelation temperature of the pharmaceutical composition is about 32° C.

In any of the foregoing embodiments, the carboxylic acid containing compound is a substituted or unsubstituted $C_5$-$C_9$ straight or branched chain alkyl-$CO_2H$.

In any of the foregoing embodiments, the carboxylic acid containing compound is a substituted $C_5$-$C_9$ straight or branched chain alkyl-$CO_2H$.

In some embodiments, the carboxylic acid containing compound is a substituted $C_5$-$C_9$ straight or branched chain alkyl-$CO_2H$, wherein the substituent is —$NH_2$. In some examples the carboxylic acid containing compound is an amino substituted 2-propylpentanoic acid. In some embodiments, the amino substituted 2-propylpentanoic acid is selected from the group consisting of 5-amino-2-propylpentanoic acid, 4-amino-2-propylpentanoic acid, 3-amino-2-propylpentanoic acid, and 2-amino-2-propylpentanoic acid.

In some embodiments, the carboxylic acid containing compound is an unsubstituted $C_5$-$C_9$ straight or branched chain alkyl-$CO_2H$.

In some embodiments, the carboxylic acid containing compound is an unsubstituted $C_6$-$C_9$ branched straight chain alkyl-$CO_2H$.

In some embodiments, the carboxylic acid containing compound is an unsubstituted $C_8$-$C_9$ branched straight chain alkyl-$CO_2H$.

In some embodiments, the carboxylic acid containing compound is an unsubstituted $C_9$ branched straight chain alkyl-$CO_2H$.

In some embodiments, the unsubstituted $C_9$ branched straight chain alkyl-$CO_2H$ carboxylic acid containing compound is Valproic acid.

In some embodiments, the Valproic acid can be in the form of an amide. In some embodiments, the amide form of Valproic acid is the condensation product with an amino acid. In some embodiments, the amide of Valproic acid is selected from the group consisting of

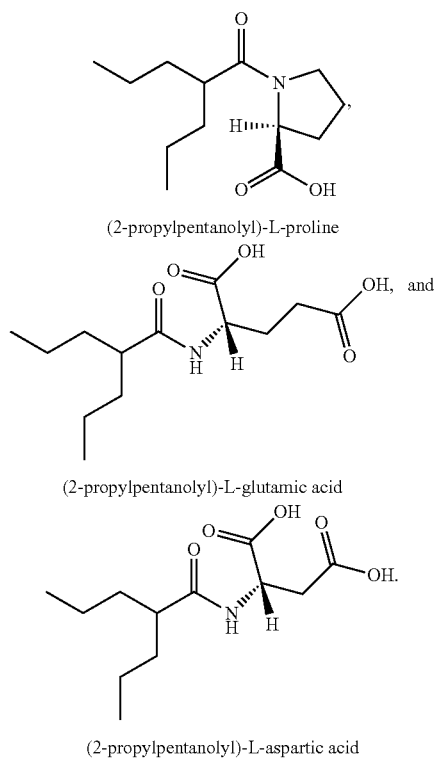

(2-propylpentanolyl)-L-proline (2-propylpentanolyl)-L-glutamic acid (2-propylpentanolyl)-L-aspartic acid In any of the foregoing embodiments, the amount of the carboxylic acid containing compound in the pharmaceutical composition is between at least 2 wt % (weight carboxylic acid containing compound/weight pharmaceutical composition) and 20 wt %. In some embodiments, the composition comprises at least 4 wt % carboxylic acid. In other embodiments, the composition comprises at least 8 wt % carboxylic acid. In some embodiments, the composition comprises at least 12 wt % carboxylic acid. In some embodiments, the composition comprises at least 16 wt % carboxylic acid. In still other embodiments, the composition comprises at least 20 wt % carboxylic acid.

In other embodiments, the composition comprises about 4 wt % carboxylic acid. In other embodiments, the composition comprises about 8 wt % carboxylic acid. In other embodiments, the composition comprises about 12 wt % carboxylic acid. In further embodiments, the composition comprises about 16 wt % carboxylic acid. In further embodiments, the composition comprises about 20 wt % carboxylic acid.

A further aspect of the present disclosure provides poloxamer containing pharmaceutical composition having a gelation temperature greater than 10° C., the composition comprising:
  a) an N-(alkylcarbamoyl)-1H-pyrazol-4-yl)-nicotinamide containing compound or a pharmaceutically acceptable salt thereof;
  b) Poloxamer 407 at greater than or equal to 21 wt % of the pharmaceutical composition; and
  c) a carboxylic acid containing compound;
wherein the pharmaceutical composition has a gelation temperature of greater than 10° C.

In some embodiments, the N-(1H-pyrazol-4-yl)-nicotinamide containing compound is an N-(alkylcarbamoyl)-1H-pyrazol-4-yl)-nicotinamide containing compound. In some embodiments, the N-(1H-pyrazol-4-yl)-nicotinamide containing compound is N-(3-((3-isopropoxypropyl)carbamoyl)-1H-pyrazol-4-yl)-6-methylnicotinamide which has the Formula II and pharmaceutically acceptable salts thereof:

Formula II

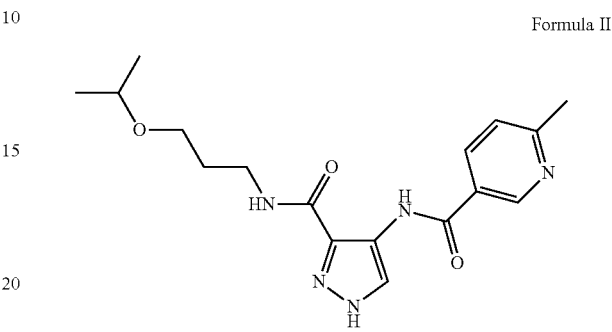

The compound of Formula II is also known as GSK-3 Inhibitor XXII.

In some embodiments, the Poloxamer 407 can be in a concentration between 21 wt % and 40 wt % relative to the composition. In another embodiment, the Poloxamer 407 is in a concentration between 21 wt % and 30 wt % relative to the composition. In another embodiment, the Poloxamer 407 is in a concentration between 23 wt % and 29 wt % relative to the composition. In another embodiment, the Poloxamer 407 is in a concentration between 23 wt % and 27 wt % relative to the composition. In another embodiment, the Poloxamer 407 is in a concentration of 25 wt % relative to the composition.

In some embodiments, the gelation temperature of the pharmaceutical composition is between about 11° C. and about 32° C. In some embodiments, the gelation temperature of the pharmaceutical composition is between is between about 15° C. and about 30° C. In some embodiments, the gelation temperature of the pharmaceutical composition is between about 20° C. and about 28° C. In some embodiments, the gelation temperature of the pharmaceutical composition is between about 24° C. and about 26° C. In some embodiments, the gelation temperature of the pharmaceutical composition is about 15° C. In some embodiments, the gelation temperature of the pharmaceutical composition is about 20° C. In some embodiments, the gelation temperature of the pharmaceutical composition is about 24° C. In some embodiments, the gelation temperature of the pharmaceutical composition is about 26° C. In some embodiments, the gelation temperature of the pharmaceutical composition is about 28° C. In some embodiments, the gelation temperature of the pharmaceutical composition is about 30° C. In some embodiments, the gelation temperature of the pharmaceutical composition is about 32° C.

In any of the foregoing embodiments, the carboxylic acid containing compound is a substituted or unsubstituted $C_5$-$C_9$ straight or branched chain alkyl-$CO_2H$.

In any of the foregoing embodiments, the carboxylic acid containing compound is a substituted $C_5$-$C_9$ straight or branched chain alkyl-$CO_2H$.

In some embodiments, the carboxylic acid containing compound is a substituted $C_5$-$C_9$ straight or branched chain alkyl-$CO_2H$, wherein the substituent is —$NH_2$. In some examples the carboxylic acid containing compound is an amino substituted 2-propylpentanoic acid. In some embodiments, the amino substituted 2-propylpentanoic acid is selected from the group consisting of 5-amino-2-propylpentanoic acid, 4-amino-2-propylpentanoic acid, 3-amino-2-propylpentanoic acid, and 2-amino-2-propylpentanoic acid.

In some embodiments, the carboxylic acid containing compound is an unsubstituted $C_5$-$C_9$ straight or branched chain alkyl-$CO_2H$.

In some embodiments, the carboxylic acid containing compound is an unsubstituted $C_6$-$C_9$ branched straight chain alkyl-$CO_2H$.

In some embodiments, the carboxylic acid containing compound is an unsubstituted $C_8$-$C_9$ branched straight chain alkyl-$CO_2H$.

In some embodiments, the carboxylic acid containing compound is an unsubstituted $C_9$ branched straight chain alkyl-$CO_2H$.

In some embodiments, the unsubstituted $C_9$ branched straight chain alkyl-$CO_2H$ carboxylic acid containing compound is Valproic acid.

In some embodiments, the Valproic acid can be in the form of an amide. In some embodiments, the amide form of Valproic acid is the condensation product with an amino acid.

In some embodiments, the amide of Valproic acid is selected from the group consisting of

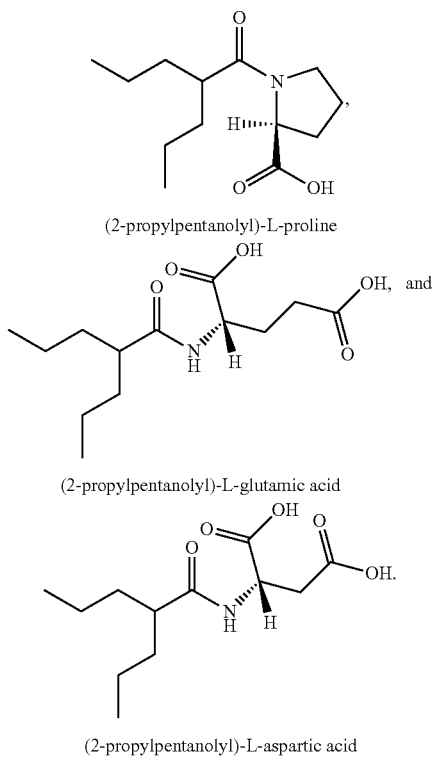

In any of the foregoing embodiments, the amount of the carboxylic acid containing compound in the pharmaceutical composition is between at least 2 wt % (weight carboxylic acid containing compound/weight pharmaceutical composition) and 20 wt %. In some embodiments, the composition comprises at least 4 wt % carboxylic acid. In other embodiments, the composition comprises at least 8 wt % carboxylic acid. In some embodiments, the composition comprises at least 12 wt % carboxylic acid. In some embodiments, the composition comprises at least 16 wt % carboxylic acid. In still other embodiments, the composition comprises at least 20 wt % carboxylic acid.

In other embodiments, the composition comprises about 4 wt % carboxylic acid. In other embodiments, the composition comprises about 8 wt % carboxylic acid. In other embodiments, the composition comprises about 12 wt % carboxylic acid. In further embodiments, the composition comprises about 16 wt % carboxylic acid. In further embodiments, the composition comprises about 20 wt % carboxylic acid.

A further aspect of the present disclosure provides poloxamer containing pharmaceutical composition having a gelation temperature greater than 10° C., the composition comprising:
  a) a 1,2,3,4-tetrahydro-[1,4]diazepino[6,7,1-hi]indole containing compound;
  b) Poloxamer 407 at greater than or equal to 21 wt % of the pharmaceutical composition; and
  c) a carboxylic acid containing compound;
wherein the pharmaceutical composition has a gelation temperature of greater than 10° C.

In some embodiments, the 1,2,3,4-tetrahydro-[1,4]diazepino[6,7,1-hi]indole containing compound is a 3-(1,2,3,4-tetrahydro-[1,4]diazepino[6,7,1-hi]indol-7-yl)-1H-pyrrole-2,5-dione containing compound. In some embodiments, the 1,2,3,4-tetrahydro-[1,4]diazepino[6,7,1-hi]indole containing compound is a 3-(imidazo[1,2-a]pyridin-3-yl)-4-(1,2,3,4-tetrahydro-[1,4]diazepino[6,7,1-hi]indol-7-yl)-1H-pyrrole-2,5-dione containing compound. In some embodiments, 1,2,3,4-tetrahydro-[1,4]diazepino[6,7,1-hi]indole containing compound is 3-(9-fluoro-2-(piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione which has the Formula III and pharmaceutically acceptable salts thereof:

Formula III

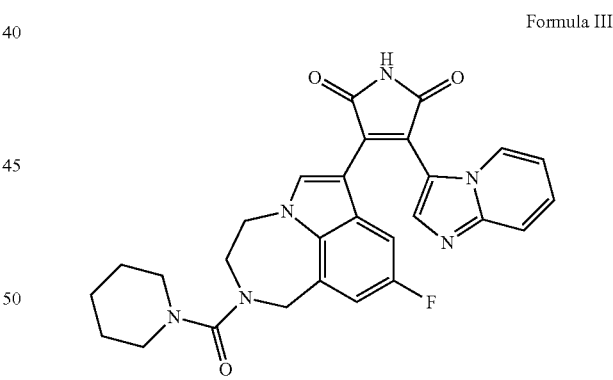

The compound of Formula III is also known as LY2090314.

In some embodiments, the Poloxamer 407 can be in a concentration between 21 wt % and 40 wt % relative to the composition. In another embodiment, the Poloxamer 407 is in a concentration between 21 wt % and 30 wt % relative to the composition. In another embodiment, the Poloxamer 407 is in a concentration between 23 wt % and 29 wt % relative to the composition. In another embodiment, the Poloxamer 407 is in a concentration between 23 wt % and 27 wt % relative to the composition. In another embodiment, the Poloxamer 407 is in a concentration of 25 wt % relative to the composition.

In some embodiments, the gelation temperature of the pharmaceutical composition is between about 11° C. and about 32° C. In some embodiments, the gelation temperature of the pharmaceutical composition is between is between about 15° C. and about 30° C. In some embodiments, the gelation temperature of the pharmaceutical composition is between about 20° C. and about 28° C. In some embodiments, the gelation temperature of the pharmaceutical composition is between about 24° C. and about 26° C. In some embodiments, the gelation temperature of the pharmaceutical composition is about 15° C. In some embodiments, the gelation temperature of the pharmaceutical composition is about 20° C. In some embodiments, the gelation temperature of the pharmaceutical composition is about 24° C. In some embodiments, the gelation temperature of the pharmaceutical composition is about 26° C. In some embodiments, the gelation temperature of the pharmaceutical composition is about 28° C. In some embodiments, the gelation temperature of the pharmaceutical composition is about 30° C. In some embodiments, the gelation temperature of the pharmaceutical composition is about 32° C.

In any of the foregoing embodiments, the carboxylic acid containing compound is a substituted or unsubstituted $C_5$-$C_9$ straight or branched chain alkyl-$CO_2H$.

In any of the foregoing embodiments, the carboxylic acid containing compound is a substituted $C_5$-$C_9$ straight or branched chain alkyl-$CO_2H$.

In some embodiments, the carboxylic acid containing compound is a substituted $C_5$-$C_9$ straight or branched chain alkyl-$CO_2H$, wherein the substituent is —$NH_2$. In some examples the carboxylic acid containing compound is an amino substituted 2-propylpentanoic acid. In some embodiments, the amino substituted 2-propylpentanoic acid is selected from the group consisting of 5-amino-2-propylpentanoic acid, 4-amino-2-propylpentanoic acid, 3-amino-2-propylpentanoic acid, and 2-amino-2-propylpentanoic acid.

In some embodiments, the carboxylic acid containing compound is an unsubstituted $C_5$-$C_9$ straight or branched chain alkyl-$CO_2H$.

In some embodiments, the carboxylic acid containing compound is an unsubstituted $C_6$-$C_9$ branched straight chain alkyl-$CO_2H$.

In some embodiments, the carboxylic acid containing compound is an unsubstituted $C_8$-$C_9$ branched straight chain alkyl-$CO_2H$.

In some embodiments, the carboxylic acid containing compound is an unsubstituted $C_9$ branched straight chain alkyl-$CO_2H$.

In some embodiments, the unsubstituted $C_9$ branched straight chain alkyl-$CO_2H$ carboxylic acid containing compound is Valproic acid.

In some embodiments, the Valproic acid can be in the form of an amide. In some embodiments, the amide form of Valproic acid is the condensation product with an amino acid. In some embodiments, the amide of Valproic acid is selected from the group consisting of

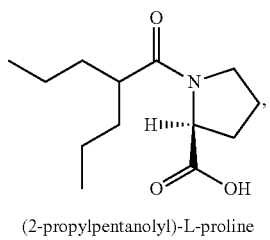

(2-propylpentanolyl)-L-proline

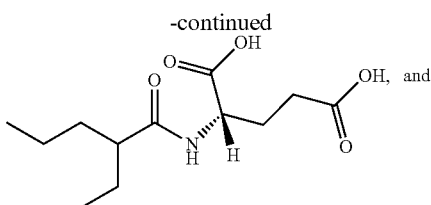

(2-propylpentanolyl)-L-glutamic acid

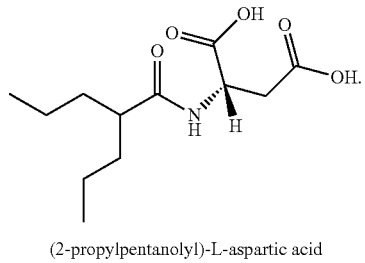

(2-propylpentanolyl)-L-aspartic acid

In any of the foregoing embodiments, the amount of the carboxylic acid containing compound in the pharmaceutical composition is between at least 2 wt % (weight carboxylic acid containing compound/weight pharmaceutical composition) and 20 wt %. In some embodiments, the composition comprises at least 4 wt % carboxylic acid. In other embodiments, the composition comprises at least 8 wt % carboxylic acid. In some embodiments, the composition comprises at least 12 wt % carboxylic acid. In some embodiments, the composition comprises at least 16 wt % carboxylic acid. In still other embodiments, the composition comprises at least 20 wt % carboxylic acid.

In other embodiments, the composition comprises about 4 wt % carboxylic acid. In other embodiments, the composition comprises about 8 wt % carboxylic acid. In other embodiments, the composition comprises about 12 wt % carboxylic acid. In further embodiments, the composition comprises about 16 wt % carboxylic acid. In further embodiments, the composition comprises about 20 wt % carboxylic acid.

A further aspect of the present disclosure provides a poloxamer containing pharmaceutical composition having a gelation temperature greater than 10° C., the composition comprising:

a) a wnt agonist or a pharmaceutically acceptable salt thereof;

b) Poloxamer 407 at greater than or equal to 21 wt % of the pharmaceutical composition; and c) Valproic acid;

wherein the pharmaceutical composition has a gelation temperature of greater than 10° C.

In some embodiments, the Poloxamer 407 can be in a concentration between 21 wt % and 40 wt % relative to the composition. In another embodiment, the Poloxamer 407 is in a concentration between 21 wt % and 30 wt % relative to the composition. In another embodiment, the Poloxamer 407 is in a concentration between 23 wt % and 29 wt % relative to the composition. In another embodiment, the Poloxamer 407 is in a concentration between 23 wt % and 27 wt % relative to the composition. In another embodiment, the Poloxamer 407 is in a concentration of 25 wt % relative to the composition.

In some embodiments, the gelation temperature of the pharmaceutical composition is between about 11° C. and about 32° C. In some embodiments, the gelation temperature of the pharmaceutical composition is between is between about 15° C. and about 30° C. In some embodiments, the gelation temperature of the pharmaceutical composition is between about 20° C. and about 28° C. In some embodiments, the gelation temperature of the pharmaceutical composition is between about 24° C. and about 26° C. In some embodiments, the gelation temperature of the pharmaceutical composition is about 15° C. In some embodiments, the gelation temperature of the pharmaceutical composition is about 20° C. In some embodiments, the gelation temperature of the pharmaceutical composition is about 24° C. In some embodiments, the gelation temperature of the pharmaceutical composition is about 26° C. In some embodiments, the gelation temperature of the pharmaceutical composition is about 28° C. In some embodiments, the gelation temperature of the pharmaceutical composition is about 30° C. In some embodiments, the gelation temperature of the pharmaceutical composition is about 32° C.

In any of the foregoing embodiments, the amount of the Valproic acid in the pharmaceutical composition is between least 2 wt % (weight Valproic acid/weight pharmaceutical composition) and 20 wt %. In some embodiments, the composition comprises at least 4 wt % Valproic acid. In other embodiments, the composition comprises at least 8 wt % Valproic acid. In some embodiments, the composition comprises at least 12 wt % Valproic acid. In some embodiments, the composition comprises at least 16 wt % Valproic acid. In still other embodiments, the composition comprises at least 20 wt % Valproic acid.

In other embodiments, the composition comprises about 4 wt % Valproic acid. In other embodiments, the composition comprises about 8 wt % Valproic acid. In other embodiments, the composition comprises about 12 wt % Valproic acid. In further embodiments, the composition comprises about 16 wt % Valproic acid. In further embodiments, the composition comprises about 20 wt % Valproic acid.

A further aspect of the present disclosure provides a poloxamer containing pharmaceutical composition having a gelation temperature greater than 10° C., the composition comprising:

a) a GSK3 inhibitor or a pharmaceutically acceptable salt thereof;

b) Poloxamer 407 at greater than or equal to 21 wt % of the pharmaceutical composition; and c) Valproic acid;

wherein the pharmaceutical composition has a gelation temperature of greater than 10° C.

In some embodiments, the Poloxamer 407 can be in a concentration between 21 wt % and 40 wt % relative to the composition. In another embodiment, the Poloxamer 407 is in a concentration between 21 wt % and 30 wt % relative to the composition. In another embodiment, the Poloxamer 407 is in a concentration between 23 wt % and 29 wt % relative to the composition. In another embodiment, the Poloxamer 407 is in a concentration between 23 wt % and 27 wt % relative to the composition. In another embodiment, the Poloxamer 407 is in a concentration of 25 wt % relative to the composition.

In some embodiments, the gelation temperature of the pharmaceutical composition is between about 11° C. and about 32° C. In some embodiments, the gelation temperature of the pharmaceutical composition is between is between about 15° C. and about 30° C. In some embodiments, the gelation temperature of the pharmaceutical composition is between about 20° C. and about 28° C. In some embodiments, the gelation temperature of the pharmaceutical composition is between about 24° C. and about 26° C. In some embodiments, the gelation temperature of the pharmaceutical composition is about 15° C. In some embodiments, the gelation temperature of the pharmaceutical composition is about 20° C. In some embodiments, the gelation temperature of the pharmaceutical composition is about 24° C. In some embodiments, the gelation temperature of the pharmaceutical composition is about 26° C. In some embodiments, the gelation temperature of the pharmaceutical composition is about 28° C. In some embodiments, the gelation temperature of the pharmaceutical composition is about 30° C. In some embodiments, the gelation temperature of the pharmaceutical composition is about 32° C.

In any of the foregoing embodiments, the amount of the Valproic acid in the pharmaceutical composition is between least 2 wt % (weight Valproic acid/weight pharmaceutical composition) and 20 wt %. In some embodiments, the composition comprises at least 4 wt % Valproic acid. In other embodiments, the composition comprises at least 8 wt % Valproic acid. In some embodiments, the composition comprises at least 12 wt % Valproic acid. In some embodiments, the composition comprises at least 16 wt % Valproic acid. In still other embodiments, the composition comprises at least 20 wt % Valproic acid.

In other embodiments, the composition comprises about 4 wt % Valproic acid. In other embodiments, the composition comprises about 8 wt % Valproic acid. In other embodiments, the composition comprises about 12 wt % Valproic acid. In further embodiments, the composition comprises about 16 wt % Valproic acid. In further embodiments, the composition comprises about 20 wt % Valproic acid.

A further aspect of the present disclosure provides poloxamer containing pharmaceutical composition having a gelation temperature greater than 10° C., the composition comprising:

a) a 2-pyrimidinylaminoethylamino-2-pyridine compound;

b) Poloxamer 407 at greater than or equal to 21 wt % of the pharmaceutical composition; and c) Valproic acid;

wherein the pharmaceutical composition has a gelation temperature of greater than 10° C.

In some embodiments, the 2-pyrimidinylaminoethylamino-2-pyridine compound is a 2,4-dichlorophenyl-5-(1H-imidazol-2-yl)-2-pyrimidinylaminoethylamino-2-pyridine compound. In some embodiments, the pyrimidine containing compound is 6-[[2-[[4-(2,4-Dichlorophenyl)-5-(5-methyl-1H-imidazol-2-yl)-2-pyrimidinyl]amino]ethyl]amino]-3-pyridinecarbonitrile which has the Formula I and pharmaceutically acceptable salts thereof:

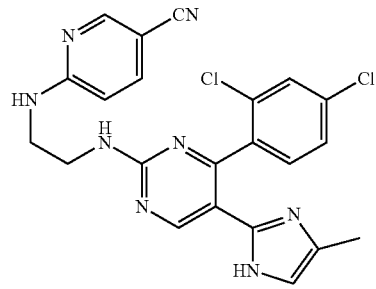

Formula I

In some embodiments, the Poloxamer 407 can be in a concentration between 21 wt % and 40 wt % relative to the composition. In another embodiment, the Poloxamer 407 is in a concentration between 21 wt % and 30 wt % relative to the composition. In another embodiment, the Poloxamer 407 is in a concentration between 23 wt % and 29 wt % relative to the composition. In another embodiment, the Poloxamer 407 is in a concentration between 23 wt % and 27 wt % relative to the composition. In another embodiment, the Poloxamer 407 is in a concentration of 25 wt % relative to the composition.

In some embodiments, the gelation temperature of the pharmaceutical composition is between about 11° C. and about 32° C. In some embodiments, the gelation temperature of the pharmaceutical composition is between is between about 15° C. and about 30° C. In some embodiments, the gelation temperature of the pharmaceutical composition is between about 20° C. and about 28° C. In some embodiments, the gelation temperature of the pharmaceutical composition is between about 24° C. and about 26° C. In some embodiments, the gelation temperature of the pharmaceutical composition is about 15° C. In some embodiments, the gelation temperature of the pharmaceutical composition is about 20° C. In some embodiments, the gelation temperature of the pharmaceutical composition is about 24° C. In some embodiments, the gelation temperature of the pharmaceutical composition is about 26° C. In some embodiments, the gelation temperature of the pharmaceutical composition is about 28° C. In some embodiments, the gelation temperature of the pharmaceutical composition is about 30° C. In some embodiments, the gelation temperature of the pharmaceutical composition is about 32° C.

In any of the foregoing embodiments, the amount of the Valproic acid in the pharmaceutical composition is between least 2 wt % (weight Valproic acid/weight pharmaceutical composition) and 20 wt %. In some embodiments, the composition comprises at least 4 wt % Valproic acid. In other embodiments, the composition comprises at least 8 wt % Valproic acid. In some embodiments, the composition comprises at least 12 wt % Valproic acid. In some embodiments, the composition comprises at least 16 wt % Valproic acid. In still other embodiments, the composition comprises at least 20 wt % Valproic acid.

In other embodiments, the composition comprises about 4 wt % Valproic acid. In other embodiments, the composition comprises about 8 wt % Valproic acid. In other embodiments, the composition comprises about 12 wt % Valproic acid. In further embodiments, the composition comprises about 16 wt % Valproic acid. In further embodiments, the composition comprises about 20 wt % Valproic acid.

A further aspect of the present disclosure provides poloxamer containing pharmaceutical composition having a gelation temperature greater than 10° C., the composition comprising:
  a) an N-(1H-pyrazol-4-yl)-nicotinamide containing compound or a pharmaceutically acceptable salt thereof;
  b) Poloxamer 407 at greater than or equal to 21 wt % of the pharmaceutical composition; and
  c) Valproic acid;
wherein the pharmaceutical composition has a gelation temperature of greater than 10° C.

In some embodiments, the N-(1H-pyrazol-4-yl)-nicotinamide containing compound is an N-(alkylcarbamoyl)-1H-pyrazol-4-yl)-nicotinamide containing compound.

In some embodiments, the N-(1H-pyrazol-4-yl)-nicotinamide containing compound is N-(3-((3 sopropoxypropyl)carbamoyl)-1H-pyrazol-4-yl)-6-methylnicotinamide which has the structure in Formula II and pharmaceutically acceptable salts thereof:

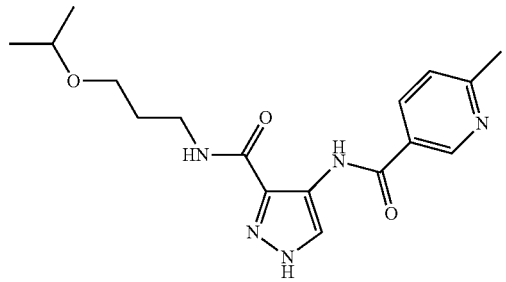

Formula II

In some embodiments, the Poloxamer 407 can be in a concentration between 21 wt % and 40 wt % relative to the composition. In another embodiment, the Poloxamer 407 is in a concentration between 21 wt % and 30 wt % relative to the composition. In another embodiment, the Poloxamer 407 is in a concentration between 23 wt % and 29 wt % relative to the composition. In another embodiment, the Poloxamer 407 is in a concentration between 23 wt % and 27 wt % relative to the composition. In another embodiment, the Poloxamer 407 is in a concentration of 25 wt % relative to the composition.

In some embodiments, the gelation temperature of the pharmaceutical composition is between about 11° C. and about 32° C. In some embodiments, the gelation temperature of the pharmaceutical composition is between is between about 15° C. and about 30° C. In some embodiments, the gelation temperature of the pharmaceutical composition is between about 20° C. and about 28° C. In some embodiments, the gelation temperature of the pharmaceutical composition is between about 24° C. and about 26° C. In some embodiments, the gelation temperature of the pharmaceutical composition is about 15° C. In some embodiments, the gelation temperature of the pharmaceutical composition is about 20° C. In some embodiments, the gelation temperature of the pharmaceutical composition is about 24° C. In some embodiments, the gelation temperature of the pharmaceutical composition is about 26° C. In some embodiments, the gelation temperature of the pharmaceutical composition is about 28° C. In some embodiments, the gelation temperature of the pharmaceutical composition is about 30° C. In some embodiments, the gelation temperature of the pharmaceutical composition is about 32° C.

In any of the foregoing embodiments, the amount of the Valproic acid in the pharmaceutical composition is between least 2 wt % (weight Valproic acid/weight pharmaceutical composition) and 20 wt %. In some embodiments, the composition comprises at least 4 wt % Valproic acid. In other embodiments, the composition comprises at least 8 wt % Valproic acid. In some embodiments, the composition comprises at least 12 wt % Valproic acid. In some embodiments, the composition comprises at least 16 wt % Valproic acid. In still other embodiments, the composition comprises at least 20 wt % Valproic acid.

In other embodiments, the composition comprises about 4 wt % Valproic acid. In other embodiments, the composition comprises about 8 wt % Valproic acid. In other embodiments, the composition comprises about 12 wt % Valproic acid. In further embodiments, the composition comprises about 16 wt % Valproic acid. In further embodiments, the composition comprises about 20 wt % Valproic acid.

A further aspect of the present disclosure provides a poloxamer containing pharmaceutical composition having a gelation temperature greater than 10° C., the composition comprising:

a) a 1,2,3,4-tetrahydro-[1,4]diazepino[6,7,1-hi]indolyl) containing compound containing compound or a pharmaceutically acceptable salt thereof;

b) Poloxamer 407 at greater than or equal to 21 wt % of the pharmaceutical composition; and c) Valproic acid;

wherein the pharmaceutical composition has a gelation temperature of greater than 10° C.

In some embodiments, the 1,2,3,4-tetrahydro-[1,4]diazepino[6,7,1-hi]indolyl) containing compound is a 1,2,3,4-tetrahydro-[1,4]diazepino[6,7,1-hi]indol-7-yl)-1H-pyrrole-2,5-dione containing compound. In some embodiments, the 1,2,3,4-tetrahydro-[1,4]diazepino[6,7,1-hi]indolyl) containing compound is a 1,2,3,4-tetrahydro-[1,4]diazepino[6,7,1-hi]indol-7-yl)-4-(imidazo[1,2-a]pyridin-3-yl)-1H-pyrrole-2,5-dione containing compound. In some embodiments, the 1,2,3,4-tetrahydro-[1,4]diazepino[6,7,1-hi]indolyl) containing compound is 3-(9-fluoro-2-(piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione which has the Formula III and pharmaceutically acceptable salts thereof:

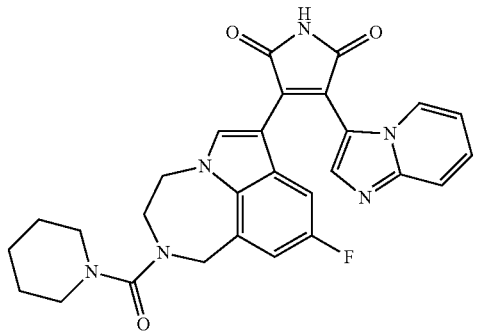

Formula III

In some embodiments, the Poloxamer 407 can be in a concentration between 21 wt % and 40 wt % relative to the composition. In another embodiment, the Poloxamer 407 is in a concentration between 21 wt % and 30 wt % relative to the composition. In another embodiment, the Poloxamer 407 is in a concentration between 23 wt % and 29 wt % relative to the composition. In another embodiment, the Poloxamer 407 is in a concentration between 23 wt % and 27 wt % relative to the composition. In another embodiment, the Poloxamer 407 is in a concentration of 25 wt % relative to the composition.

In some embodiments, the gelation temperature of the pharmaceutical composition is between about 11° C. and about 32° C. In some embodiments, the gelation temperature of the pharmaceutical composition is between is between about 15° C. and about 30° C. In some embodiments, the gelation temperature of the pharmaceutical composition is between about 20° C. and about 28° C. In some embodiments, the gelation temperature of the pharmaceutical composition is between about 24° C. and about 26° C. In some embodiments, the gelation temperature of the pharmaceutical composition is about 15° C. In some embodiments, the gelation temperature of the pharmaceutical composition is about 20° C. In some embodiments, the gelation temperature of the pharmaceutical composition is about 24° C. In some embodiments, the gelation temperature of the pharmaceutical composition is about 26° C. In some embodiments, the gelation temperature of the pharmaceutical composition is about 28° C. In some embodiments, the gelation temperature of the pharmaceutical composition is about 30° C. In some embodiments, the gelation temperature of the pharmaceutical composition is about 32° C.

In any of the foregoing embodiments, the amount of the Valproic acid in the pharmaceutical composition is between least 2 wt % (weight Valproic acid/weight pharmaceutical composition) and 20 wt %. In some embodiments, the composition comprises at least 4 wt % Valproic acid. In other embodiments, the composition comprises at least 8 wt % Valproic acid. In some embodiments, the composition comprises at least 12 wt % Valproic acid. In some embodiments, the composition comprises at least 16 wt % Valproic acid. In still other embodiments, the composition comprises at least 20 wt % Valproic acid.

In other embodiments, the composition comprises about 4 wt % Valproic acid. In other embodiments, the composition comprises about 8 wt % Valproic acid. In other embodiments, the composition comprises about 12 wt % Valproic acid. In further embodiments, the composition comprises about 16 wt % Valproic acid. In further embodiments, the composition comprises about 20 wt % Valproic acid.

A further aspect of the present disclosure provides a poloxamer containing pharmaceutical composition having a gelation temperature greater than 10° C., the composition comprising a) a compound of the Formula I

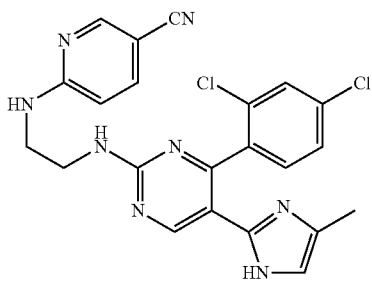

Formula I or a pharmaceutically acceptable salt thereof;

b) Poloxamer 407 in weight percentage of more than 21% wt; and c) Valproic acid;

wherein the pharmaceutical composition has a gelation temperature of greater than 10° C.

In some embodiments, the Poloxamer 407 can be in a concentration between 21 wt % and 40 wt % relative to the composition. In another embodiment, the Poloxamer 407 is in a concentration between 21 wt % and 30 wt % relative to the composition. In another embodiment, the Poloxamer 407 is in a concentration between 23 wt % and 29 wt % relative to the composition. In another embodiment, the Poloxamer 407 is in a concentration between 23 wt % and 27 wt % relative to the composition. In another embodiment, the Poloxamer 407 is in a concentration of 25 wt % relative to the composition.

In some embodiments, the gelation temperature of the pharmaceutical composition is between about 11° C. and about 32° C. In some embodiments, the gelation temperature of the pharmaceutical composition is between is between about 15° C. and about 30° C. In some embodiments, the gelation temperature of the pharmaceutical composition is between about 20° C. and about 28° C. In some embodiments, the gelation temperature of the pharmaceutical composition is between about 24° C. and about 26° C. In some embodiments, the gelation temperature of the pharmaceutical composition is about 15° C. In some embodiments, the gelation temperature of the pharmaceutical composition is about 20° C. In some embodiments, the gelation temperature of the pharmaceutical composition is about 24° C. In some embodiments, the gelation temperature of the pharmaceutical composition is about 26° C. In some embodiments, the gelation temperature of the pharmaceutical composition is about 28° C. In some embodiments, the gelation temperature of the pharmaceutical composition is about 30° C. In some embodiments, the gelation temperature of the pharmaceutical composition is about 32° C.

In any of the foregoing embodiments, the amount of the Valproic acid in the pharmaceutical composition is between least 2 wt % (weight Valproic acid/weight pharmaceutical composition) and 20 wt %. In some embodiments, the composition comprises at least 4 wt % Valproic acid. In other embodiments, the composition comprises at least 8 wt % Valproic acid. In some embodiments, the composition comprises at least 12 wt % Valproic acid. In some embodiments, the composition comprises at least 16 wt % Valproic acid. In still other embodiments, the composition comprises at least 20 wt % Valproic acid.

In other embodiments, the composition comprises about 4 wt % Valproic acid. In other embodiments, the composition comprises about 8 wt % Valproic acid. In other embodiments, the composition comprises about 12 wt % Valproic acid. In further embodiments, the composition comprises about 16 wt % Valproic acid. In further embodiments, the composition comprises about 20 wt % Valproic acid.

A further aspect of the present disclosure provides a poloxamer containing pharmaceutical composition having a gelation temperature greater than 10° C., the composition comprising:
 a) a compound of Formula II

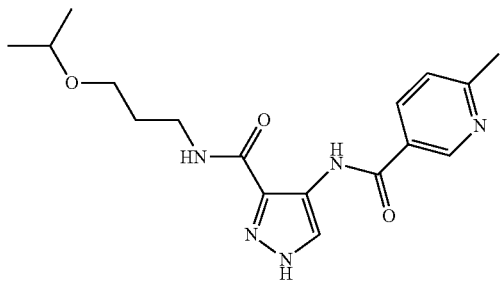

Formula II or a pharmaceutically acceptable salt thereof;
 b) Poloxamer 407 in weight percentage of more than 21% wt; and
 c) Valproic acid;
wherein the pharmaceutical composition has a gelation temperature of greater than 10° C.

In some embodiments, the Poloxamer 407 can be in a concentration between 21 wt % and 40 wt % relative to the composition. In another embodiment, the Poloxamer 407 is in a concentration between 21 wt % and 30 wt % relative to the composition. In another embodiment, the Poloxamer 407 is in a concentration between 23 wt % and 29 wt % relative to the composition. In another embodiment, the Poloxamer 407 is in a concentration between 23 wt % and 27 wt % relative to the composition. In another embodiment, the Poloxamer 407 is in a concentration of 25 wt % relative to the composition.

In some embodiments, the gelation temperature of the pharmaceutical composition is between about 11° C. and about 32° C. In some embodiments, the gelation temperature of the pharmaceutical composition is between is between about 15° C. and about 30° C. In some embodiments, the gelation temperature of the pharmaceutical composition is between about 20° C. and about 28° C. In some embodiments, the gelation temperature of the pharmaceutical composition is between about 24° C. and about 26° C. In some embodiments, the gelation temperature of the pharmaceutical composition is about 15° C. In some embodiments, the gelation temperature of the pharmaceutical composition is about 20° C. In some embodiments, the gelation temperature of the pharmaceutical composition is about 24° C. In some embodiments, the gelation temperature of the pharmaceutical composition is about 26° C. In some embodiments, the gelation temperature of the pharmaceutical composition is about 28° C. In some embodiments, the gelation temperature of the pharmaceutical composition is about 30° C. In some embodiments, the gelation temperature of the pharmaceutical composition is about 32° C.

In any of the foregoing embodiments, the amount of the Valproic acid in the pharmaceutical composition is between least 2 wt % (weight Valproic acid/weight pharmaceutical composition) and 20 wt %. In some embodiments, the composition comprises at least 4 wt % Valproic acid. In other embodiments, the composition comprises at least 8 wt % Valproic acid. In some embodiments, the composition comprises at least 12 wt % Valproic acid. In some embodiments, the composition comprises at least 16 wt % Valproic acid. In still other embodiments, the composition comprises at least 20 wt % Valproic acid.

In other embodiments, the composition comprises about 4 wt % Valproic acid. In other embodiments, the composition comprises about 8 wt % Valproic acid. In other embodiments, the composition comprises about 12 wt % Valproic acid. In further embodiments, the composition comprises about 16 wt % Valproic acid. In further embodiments, the composition comprises about 20 wt % Valproic acid.

A further aspect of the present disclosure provides a poloxamer containing pharmaceutical composition having a gelation temperature greater than 10° C., the composition comprising
 a) a compound of Formula III

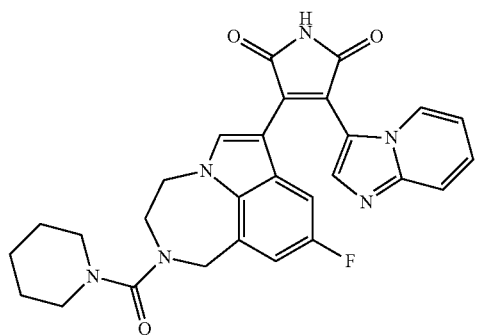

Formula III or a pharmaceutically acceptable salt thereof;
b) Poloxamer 407 in weight percentage of more than 21% wt; and
c) Valproic acid;
wherein the pharmaceutical composition has a gelation temperature of greater than 10° C.

In some embodiments, the Poloxamer 407 can be in a concentration between 21 wt % and 40 wt % relative to the composition. In another embodiment, the Poloxamer 407 is in a concentration between 21 wt % and 30 wt % relative to the composition. In another embodiment, the Poloxamer 407 is in a concentration between 23 wt % and 29 wt % relative to the composition. In another embodiment, the Poloxamer 407 is in a concentration between 23 wt % and 27 wt % relative to the composition. In another embodiment, the Poloxamer 407 is in a concentration of 25 wt % relative to the composition.

In some embodiments, the gelation temperature of the pharmaceutical composition is between about 11° C. and about 32° C. In some embodiments, the gelation temperature of the pharmaceutical composition is between is between about 15° C. and about 30° C. In some embodiments, the gelation temperature of the pharmaceutical composition is between about 20° C. and about 28° C. In some embodiments, the gelation temperature of the pharmaceutical composition is between about 24° C. and about 26° C. In some embodiments, the gelation temperature of the pharmaceutical composition is about 15° C. In some embodiments, the gelation temperature of the pharmaceutical composition is about 20° C. In some embodiments, the gelation temperature of the pharmaceutical composition is about 24° C. In some embodiments, the gelation temperature of the pharmaceutical composition is about 26° C. In some embodiments, the gelation temperature of the pharmaceutical composition is about 28° C. In some embodiments, the gelation temperature of the pharmaceutical composition is about 30° C. In some embodiments, the gelation temperature of the pharmaceutical composition is about 32° C.

In any of the foregoing embodiments, the amount of the Valproic acid in the pharmaceutical composition is between least 2 wt % (weight Valproic acid/weight pharmaceutical composition) and 20 wt %. In some embodiments, the composition comprises at least 4 wt % Valproic acid. In other embodiments, the composition comprises at least 8 wt % Valproic acid. In some embodiments, the composition comprises at least 12 wt % Valproic acid. In some embodiments, the composition comprises at least 16 wt % Valproic acid. In still other embodiments, the composition comprises at least 20 wt % Valproic acid.

In other embodiments, the composition comprises about 4 wt % Valproic acid. In other embodiments, the composition comprises about 8 wt % Valproic acid. In other embodiments, the composition comprises about 12 wt % Valproic acid. In further embodiments, the composition comprises about 16 wt % Valproic acid. In further embodiments, the composition comprises about 20 wt % Valproic acid.

In any of the foregoing aspects and embodiments, the poloxamer can be in a concentration between 21 wt % and 40 wt % relative to the composition. In another embodiment, the poloxamer is in a concentration between 21 wt % and 30 wt % relative to the composition. In another embodiment, the poloxamer is in a concentration between 23 wt % and 29 wt % relative to the composition. In another embodiment, the poloxamer is in a concentration between 23 wt % and 27 wt % relative to the composition. In another embodiment, the poloxamer is in a concentration of 25 wt % relative to the composition.

Poloxamers are commercially available (e.g., Pluronic® polyols are available from BASF Corporation). Alternatively, poloxamers can be synthesized by known techniques.

In one or more embodiments the viscosity of the composition at about body temperature is substantially higher than the viscosity of the composition at 4° C. In some embodiments the viscosity of the composition at 4° C. is between 100 cp and 100,000 cp. In some embodiments the viscosity of the composition at 4° C. is between 100 cp and 10,000 cp. In some embodiments the viscosity of the composition at 4° C. is between 100 cp and 1,000 cp. In some embodiments the viscosity of the composition at 37° C. is between 50,000 cp and 500,000 cp. In some embodiments the viscosity of the composition at 37° C. is between 100,000 cp and 300,000 cp. In some embodiments the viscosity of the composition at 37° C. is at least 10-fold greater than the viscosity of the composition at 4° C. In some embodiments the viscosity of the composition at 37° C. is at least 50-fold greater than the viscosity of the composition at 4° C.

In other embodiments, the carboxylic acid is in a concentration between 20 and 160 mg/mL relative to the composition. In other embodiments, the carboxylic acid is in a concentration of approximately 87.5 mg/mL relative to the composition.

In some embodiments, it is desirable that the formulation be sufficiently viscous that it remain in an area of administration for a suitable period of time, e.g., 1 min, 5 min, 10 min, 30 min., 1 hour, 5 hours, 12, hours, 1 day, 2 days, 7 days. The desired area may be external to the eardrum, but in contact therewith, e.g., where it can be desired that a layer of solution remain in contact with the eardrum (e.g., not flow out of ear) when the recipient subject is upright; even if some of a viscous formulation exits the ear canal, a viscous film of layer can, in some embodiments, be let in contact with the eardrum.

In some embodiments, the final formulation is a liquid at storage temperature (4° C.), and formed a semisolid gel above its liquid-gel transition temperature (37° C.). In other embodiments, compositions have a viscosity of less than 100,000 centipoise (cps) at 25° C. Compositions also have a minimum yield stress that is sufficient for maintaining the formulation against the tympanic membrane. Yield stress is the amount of force that causes a solid material to exhibit liquid-like behavior in that it continues to deform with no further increase in stress. Minimum yield stress is dependent on the thickness of the applied gel, but is independent of the geometry of the gel and the temperature of the environment. Minimum yield stress of a composition refers to an applied gel having a thickness of 4 mm and a density of 1 g/L. Yield stress ($\sigma_0$) is represented as $\sigma_0 = \rho g h$, where p is density, g is the acceleration due to gravity, and h is the layer thickness. Typically, minimum yield stress is about 39 pascals (Pa).

Viscogenic agents are typically polymers or other chemical moieties that increase the viscosity of a fluid. Suitable viscogenic agents, when included in a composition, allow the composition to transform from a liquid-like state (e.g., flowable) at 25° C. to a solid-like state (e.g., a gel) after contact with the tympanic membrane, and can be non-biodegradable, (e.g., not broken down by chemicals or enzymes naturally present in a mammal, or biodegradable). Compositions include an amount of viscogenic agent effective to yield a viscosity of the composition of less than 100,000 cps at 25° C. (e.g., less than 90,000, 60,000, 30,000, 20,000, or 10,000 cps) and, generally, a minimum yield stress of 39 Pa after application to the tympanic membrane. Typically, a composition includes 0.05 to 50% of a viscogenic agent (e.g., 0.15 to 25, 5 to 45, 10 to 40, 12 to 37, 15 to 35, 17 to 33, or 20 to 30% of a viscogenic agent).

Exemplary viscogenic agents include gellan (GELRITE or KELCOGEL), CARBOPOL 940 with hydroxypropylmethylcellulose (HPMC), N-isopropyl acrylamide (NiPAAm) with sodium acrylate and n-N-alkylacrylamide, polyacrylic acid with polyethylene glycol (PEG) or polymethacryhc acid with PEG, cellulose acetate hydrogen phthalate latex (CAP), sodium alginate, and nonionic surfactants such as poloxamers (PLURIONIC) and polyoxamine (TETRONIC) reversible temperature-dependent gelling systems.

Among other things, the compositions provided herein are useful for the prophylaxis and/or treatment of acute and chronic ear disease and hearing loss, dizziness and balance problems especially of sudden hearing loss, acoustic trauma, hearing loss due to chronic noise exposure, presbycusis, trauma during implantation of the inner ear prosthesis (insertion trauma), dizziness due to diseases of the inner ear area, dizziness related and/or as a symptom of Meniere's disease, vertigo related and/or as a symptom of Meniere's disease, tinnitus, and hearing loss due to antibiotics and cytostatics and other drugs.

Stem cells exhibit an extraordinary ability to generate multiple cell types in the body. Besides embryonic stem cells, tissue specific stem cells serve a critical role during development as well as in homeostasis and injury repair in the adult. Stem cells renew themselves through proliferation as well as generate tissue specific cell types through differentiation. The characteristics of different stem cells vary from tissue to tissue, and are determined by their intrinsic genetic and epigenetic status. However, the balance between self-renewal and differentiation of different stem cells are all stringently controlled. Uncontrolled self-renewal may lead to overgrowth of stem cells and possibly tumor formation, while uncontrolled differentiation may exhaust the stem cell pool, leading to an impaired ability to sustain tissue homeostasis. Thus, stem cells continuously sense their environment and appropriately respond with proliferation, differentiation or apoptosis. It would be desirable to drive regeneration by controlling the timing and extent of stem cell proliferation and differentiation. Controlling the proliferation with small molecules that are cleared over time would allow for control of the timing and extent of stem cell proliferation and differentiation. Remarkably, tissue stem cells from different tissues share a limited number of signaling pathways for the regulation of their self-renewal and differentiation, albeit in a very context dependent manner. Some of these pathways are the Wnt and GSK3-beta pathways.

Lgr5 is expressed across a diverse range of tissues and has been identified as a biomarker of adult stem cells in a variety of tissues such as the gut epithelia (Barker et al. 2007), kidney, hair follicle, and stomach (Barker et al, 2010; Haegebarth & Clevers, 2009). For example, it was first published in 2011, that mammalian inner ear hair cells are derived from LGR5$^+$ cells (Chai et al, 2011, Shi et al. 2012). Lgr5 is a known component of the Wnt/beta-catenin pathway, which has been shown to play major roles in differentiation, proliferation, and inducing stem cell characteristics (Barker et al. 2007).

Permanent damage to the hair cells of the inner ear results in sensorineural hearing loss, leading to communication difficulties in a large percentage of the population. Hair cells are the receptor cells that transduce the acoustic stimulus. Regeneration of damaged hair cells would provide an avenue for the treatment of a condition that currently has no therapies other than prosthetic devices. Although hair cells do not regenerate in the mammalian cochlea, new hair cells in lower vertebrates are generated from epithelial cells, called supporting cells, that surround hair cells.

Prior work has focused on transdifferentiation of supporting cells into hair cells through activation or forced expression of genes that lead to hair cell formation, with a particular focus on mechanisms to enhance expression of Atohl (Bermingham et al., 1999; Zheng and Gao, 2000; Izumikawa et al., 2005; Mizutari et al., 2013). Interestingly, cells transduced with Atohl vectors have been shown to acquire vestibular phenotypes (Kawamoto et al., 2003; Huang et al., 2009; Yang et al., 2012, 2013), and lack complete development. As mentioned, upregulating Atohl via gene insertion has been shown to create non-cochlear cell types that behave in a manner that is not found within the native cochlea. In addition, these methods increase hair cell numbers but decrease supporting cell numbers. Since supporting cells are known to have specialized roles (Ramirez-Camancho 2006, Dale and Jagger 2010), loss of these cells could create problems in proper cochlear function.

In one aspect the present disclosure provides compositions useful for controlled proliferation of stem cells comprising administering to a cell population an effective amount of a composition herein described.

Among the various aspects of the present disclosure, therefore, may be noted a method for activating the Wnt pathway in a cell population to increase the capacity of the population for self-renewal, i.e., the capacity for repeated generation of daughter cells with equivalent proliferation and 'cell fate specification' potential, and differentiation, i.e., the capacity for generation of daughter cells specified for differentiation. In one embodiment, the cell population is a cochlear supporting cell population. The Wnt pathway may also be activated upstream of the c-myc gene in members of the population and without any genetic modification of the population. Further, the Wnt pathway can also be activated by small molecules that transiently induce such activity. Additionally, the supporting cell population includes supporting cells that are LGR5$^+$ and endogenous to the Organ of Corti.

In certain embodiments a composition includes a Notch agonist or an HDAC inhibitor selected such as Valproic acid or a prodrug, ester, salt form, or amide thereof. Optionally, the composition also includes a Stemness Driver. Optionally, the Stemness Driver is a Wnt agonist. In some embodiments, the Wnt agonist is a GSK3 inhibitor. In some embodiments the Wnt agonist is CHIR99021, LY2090314, AZD 1080, or GSK3 Inhibitor XXII.

In certain embodiments, therefore, the present disclosure provides compositions that have the capacity to induce self-renewal of a population of supporting cells. These compositions have the capacity to activate pathways and mechanisms that are known to be involved in inducing stem cell properties, such as those used to create "induced pluripotent stem cells". These pathways are activated with small molecules. For example, a composition when applied in vitro to a supporting cell population may induce the population to proliferate to a high degree and in high purity in a Stem Cell Proliferation Assay, and also allow the population to differentiate into a high purity population of hair cells in a Stem Cell Differentiation Assay. In one such embodiment, the composition induces and maintains stem cell properties by proliferating to produce stem cell that can divide for many generations and maintain the ability to have a high proportion of the resulting cells differentiate into hair cells. Further, the proliferating stem cells express stem cell markers which may include one or more of Lgr5, Sox2, Opem1, Phex, lin28, Lgr6, cyclin D1, Msx1, Myb, Kit, Gdnf3, Zic3, Dppa3, Dppa4, Dppa5, Nanog, Esrrb, Rex1, Dnmt3a, Dnmt3b, Dnmt31, Utf1, Tcl1, Oct4, Klf4, Pax6, Six2, Zic1, Zic2, Otx2, Bmi1, CDX2, STAT3, Smad1, Smad2, smad2/3, smad4, smad5, and smad7.

In certain embodiments, the disclosure provides a method of and compositions for generating hair cells, the method comprising: administering or causing to be administered to a stem cell population (e.g., of an in vitro, ex vivo, or in vivo sample/subject) a composition comprising a GSK3-beta inhibitor (or a derivative or pharmaceutically acceptable salt thereof) and/or Wnt agonist (or a derivative or pharmaceutically acceptable salt thereof), thereby proliferating stem cells in the stem cell population and resulting in an expanded population of stem cells; and exposing the expanded population of stem cells to a GSK3-beta inhibitor (or a derivative or pharmaceutically acceptable salt thereof) and/or a Wnt agonist (or a derivative or pharmaceutically acceptable salt thereof), thereby facilitating generation of inner ear hair cells from the expanded population of stem cells.

In certain embodiments, the disclosure provides methods for preventing and treating auditory dysfunction. For example, in certain embodiments, the disclosure provides methods for preventing or treating auditory impairments or restoring and improving hearing in a subject comprising administering to said subject an effective amount of a composition herein describe.

The methods and compositions of the present disclosure allow greater and thus more effective dosing with these ototoxicity-inducing pharmaceutical drugs, while concomitantly preventing or reducing ototoxic effects caused by these drugs. The methods of the present disclosure provide a safe, effective, and prolonged means for prophylactic or curative treatment of hearing impairments related to inner ear tissue damage, loss, or degeneration, particularly sound or aging-induced, and ototoxin-induced, and particularly involving inner ear hair cells. In certain embodiments, the present disclosure provides compositions and methods that address one or more of these or other goals.

This disclosure relates to compositions useful in methods for inducing, promoting, or enhancing the growth, proliferation, or regeneration of inner ear tissue, for example, inner ear supporting cells and/or inner ear hair cells.

The present disclosure relates to methods and compositions to activate the Wnt pathway or to inhibit GSK3-beta activity.

In another aspect the present disclosure provides to compositions and methods for controlled proliferation of stem cells comprising administering to a cell population an effective amount of a composition provided herein.

In another aspect the present disclosure relates to compositions and methods to prevent, reduce or treat the incidence and/or severity of disorders or diseases associated with absence or lack of certain tissue cells. In one aspect the present disclosure relates to compositions and methods to prevent, reduce or treat the incidence and/or severity of inner ear disorders and hearing impairments involving inner ear tissue, particularly inner ear hair cells, their progenitors, and optionally, the stria vascularis, and associated auditory nerves. Of particular interest are those conditions that lead to permanent hearing loss where reduced number of hair cells may be responsible and/or decreased hair cell function. Also of interest are those arising as an unwanted side-effect of ototoxic therapeutic drugs including cisplatin and its analogs, aminoglycoside antibiotics, salicylate and its analogs, or loop diuretics. In certain embodiments, the present disclosure relates to inducing, promoting, or enhancing the growth, proliferation or regeneration of inner ear tissue, particularly inner ear supporting cells and hair cells.

When cochlea supporting cell populations are treated with the compositions described herein, whether the population is in vivo or in vitro, the treated supporting cells exhibit stem-like behavior in that the treated supporting cells have the capacity to proliferate and differentiate and, more specifically, differentiate into cochlear hair cells. Alternatively, the composition induces and maintains the supporting cells to produce daughter stem cells that can divide for many generations and maintain the ability to have a high proportion of the resulting cells differentiate into hair cells. In certain embodiments, the proliferating stem cells express stem cell markers which may include Lgr5, Sox2, Opem1, Phex, lin28, Lgr6, cyclin D1, Msx1, Myb, Kit, Gdnf3, Zic3, Dppa3, Dppa4, Dppa5, Nanog, Esrrb, Rex1, Dnmt3a, Dnmt3b, Dnmt31, Utf1, Tcl1, Oct4, Klf4, Pax6, Six2, Zic1, Zic2, Otx2, Bmi1, CDX2, STAT3, Smad1, Smad2, smad2/3, smad4, smad5, and/or smad7.

In some embodiments, the method of the present disclosure may be used to maintain, or even transiently increase stemness (i.e., self-renewal) of a pre-existing supporting cell population prior to significant hair cell formation. In some embodiments, the pre-existing supporting cell population comprises inner pillar cells, outer pillar cells, inner phalangeal cells, Deiter cells, Hensen cells, Boettcher cells, and/or Claudius cells. Morphological analyses with immunostaining (including cell counts) and lineage tracing across a Representative Microscopy Samples may be used to confirm expansion of one or more of these cell-types. In some embodiments, the pre-existing supporting cells comprise Lgr5$^+$ cells. Morphological analyses with immunostaining (including cell counts) and qPCR and RNA hybridization may be used to confirm Lgr5 upregulation amongst the cell population.

Advantageously, the methods of the present disclosure achieve these goals without the use of genetic manipulation. Germ-line manipulation used in many academic studies is not a therapeutically desirable approach to treating hearing loss. In general, the therapy involves the administration of a small molecule, peptide, antibody, or other non-nucleic acid molecule or nucleic acid delivery vector unaccompanied by gene therapy. In certain embodiments, the therapy involves the administration of a small organic molecule. Alternatively, hearing protection or restoration is achieved through the use of a (non-genetic) therapeutic that is injected in the middle ear and diffuses into the cochlea.

The cochlea relies heavily on all present cell types, and the organization of these cells is important to their function. As supporting cells play an important role in neurotransmitter cycling and cochlear mechanics. Thus, maintaining a rosette patterning within the organ of Corti may be important for function. Cochlear mechanics of the basilar membrane activate hair cell transduction. Due to the high sensitivity of cochlear mechanics, it is also desirable to avoid masses of cells. In all, maintaining proper distribution and relation of hair cells and supporting cells along the basilar membrane, even after proliferation, is likely a desired feature for hearing as supporting cell function and proper mechanics is necessary for normal hearing.

In one embodiment of the present disclosure, the cell density of hair cells in a cochlear cell population is expanded in a manner that maintains, or even establishes, the rosette pattern characteristic of cochlear epithelia.

In accordance with one aspect of the present disclosure, the cell density of hair cells may be increased in a population of cochlear cells comprising both hair cells and supporting cells. The cochlear cell population may be an in vivo population (i.e., comprised by the cochlear epithelium of a subject) or the cochlear cell population may be an in vitro (ex vivo) population. If the population is an in vitro population, the increase in cell density may be determined by reference to a Representative Microscopy Sample of the population taken prior and subsequent to any treatment. If the population is an in vivo population, the increase in cell density may be determined indirectly by determining an effect upon the hearing of the subject with an increase in hair cell density correlating to an improvement in hearing.

In one embodiment, supporting cells placed in a Stem Cell Proliferation Assay in the absence of neuronal cells form ribbon synapses.

In a native cochlea, patterning of hair cells and supporting cells occurs in a manner parallel to the basilar membrane. In one embodiment of the present disclosure, the proliferation of supporting cells in a cochlear cell population is expanded in a manner that the basilar membrane characteristic of cochlear epithelia.

In one embodiment, the number of supporting cells in an initial cochlear cell population is selectively expanded by treating the initial cochlear cell population with a composition comprising the composition comprising the salt of Formula I to form an intermediate cochlear cell population and wherein the ratio of supporting cells to hair cells in the intermediate cochlear cell population exceeds the ratio of supporting cells to hair cells in the initial cochlear cell population. The expanded cochlear cell population may be, for example, an in vivo population, an in vitro population or even an in vitro explant. In one such embodiment, the ratio of supporting cells to hair cells in the intermediate cochlear cell population exceeds the ratio of supporting cells to hair cells in the initial cochlear cell population. For example, in one such embodiment the ratio of supporting cells to hair cells in the intermediate cochlear cell population exceeds the ratio of supporting cells to hair cells in the initial cochlear cell population by a factor of 1.1. By way of further example, in one such embodiment the ratio of supporting cells to hair cells in the intermediate cochlear cell population exceeds the ratio of supporting cells to hair cells in the initial cochlear cell population by a factor of 1.5. By way of further example, in one such embodiment the ratio of supporting cells to hair cells in the intermediate cochlear cell population exceeds the ratio of supporting cells to hair cells in the initial cochlear cell population by a factor of 2. By way of further example, in one such embodiment the ratio of supporting cells to hair cells in the intermediate cochlear cell population exceeds the ratio of supporting cells to hair cells in the initial cochlear cell population by a factor of 3. In each of the foregoing embodiments, the capacity of a composition of the present disclosure to expand a cochlear cell population as described in this paragraph may be determined by means of a Stem Cell Proliferation Assay.

In one embodiment, the number of stem cells in a cochlear cell population is expanded to form an intermediate cochlear cell population by treating a cochlear cell population with a composition comprising the composition comprising the composition comprising the salt of Formula I wherein the cell density of stem cells in the intermediate cochlear cell population exceeds the cell density of stem cells in the initial cochlear cell population. The treated cochlear cell population may be, for example, an in vivo population, an in vitro population or even an in vitro explant. In one such embodiment, the cell density of stem cells in the treated cochlear cell population exceeds the cell density of stem cells in the initial cochlear cell population by a factor of at least 1.1. For example, in one such embodiment the cell density of stem cells in the treated cochlear cell population exceeds the cell density of stem cells in the initial cochlear cell population by a factor of at least 1.25. For example, in one such embodiment the cell density of stem cells in the treated cochlear cell population exceeds the cell density of stem cells in the initial cochlear cell population by a factor of at least 1.5. By way of further example, in one such embodiment the cell density of stem cells in the treated cochlear cell population exceeds the cell density of stem cells in the initial cochlear cell population by a factor of at least 2. By way of further example, in one such embodiment the cell density of stem cells in the treated cochlear cell population exceeds the cell density of stem cells in the initial cochlear cell population by a factor of at least 3. In vitro cochlear cell populations may expand significantly more than in vivo populations; for example, in certain embodiments the cell density of stem cells in an expanded in vitro population of stem cells may be at least 4, 5, 6, 7, 8, 9, 10, 15, 20, 25, 30, 35, 40, 45, 50, 75, 100, 200, 300, 400, 500, 600, 700, 800, 900, 1000, 2,000 or even 3,000 times greater than the cell density of the stem cells in the initial cochlear cell population. In each of the foregoing embodiments, the capacity of a composition of the present disclosure to expand a cochlear cell population as described in this paragraph may be determined by means of a Stem Cell Proliferation Assay.

In accordance with one aspect of the present disclosure, a cochlea supporting cell population is treated with a composition comprising the composition comprising the salt of Formula I to increase the Lgr5 activity of the population. For example, in one embodiment the composition comprising the salt of Formula I has the capacity to increase and maintain the Lgr5 activity of an in vitro population of cochlea supporting cells by factor of at least 1.2. By way of further example, in one such embodiment the composition has the capacity to increase the Lgr5 activity of an in vitro population of cochlea supporting cells by factor of 1.5. By way of further example, in one such embodiment the composition has the capacity to increase the Lgr5 activity of an in vitro population of cochlea supporting cells by factor of 2, 3, 5 10, 100, 500, 1,000, 2,000 or even 3,000. Increases in Lgr5 activity may also be observed for in vivo populations but the observed increase may be somewhat more modest. For example, in one embodiment the composition has the capacity to increase the Lgr5 activity of an in vivo population of cochlea supporting cells by at least 5%. By way of further example, in one such embodiment the composition has the capacity to increase the Lgr5 activity of an in vivo population of cochlea supporting cells by at least 10%. By way of further example, in one such embodiment the composition has the capacity to increase the Lgr5 activity of an in vivo population of cochlea supporting cells by at least 20%. By way of further example, in one such embodiment the composition has the capacity to increase the Lgr5 activity of an in vivo population of cochlea supporting cells by at least 30%. In each of the foregoing embodiments, the capacity of the composition for such an increase in Lgr5 activity may be demonstrated, for example, in an In vitro Lgr5[+] Activity Assay and in an in vivo population may be demonstrated, for example, in an In vivo Lgr5[+] Activity Assay, as measured by isolating the organ and performing morphological analyses using immunostaining, endogenous fluorescent protein expression of Lgr5 (e.g.,Lgr5, Sox2), and qPCR for Lgr5.

In addition to increasing the Lgr5 activity of the population, the number of Lgr5[+] supporting cells in a cochlea cell population may be increased by treating a cochlea cell population containing Lgr5+ supporting cells (whether in vivo or in vitro) with a composition comprising the composition comprising the salt of Formula I. In general, the cell density of the stem/progenitor supporting cells may expand relative to the initial cell population via one or more of several mechanisms. For example, in one such embodiment, newly generated Lgr5+ supporting cells may be generated that have increased stem cell propensity (i.e., greater capacity to differentiate into hair cell). By way of further example, in one such embodiment no daughter Lgr5+ cells are generated by cell division, but pre-existing Lgr5+ supporting cells are induced to differentiate into hair cells. By way of further example, in one such embodiment no daughter cells are generated by cell division, but Lgr5− supporting cells are activated to a greater level of Lgr5 activity and the activated supporting cells are then able to differentiate into hair cells. Regardless of the mechanism, in one embodiment the composition of the present disclosure has the capacity to increase the cell density of Lgr5+ supporting cells in an in vitro isolated cell population of cochlea supporting cells by factor of at least 5. By way of further example, in one such embodiment the composition has the capacity to increase the cell density of Lgr5+ supporting cells in an in vitro population of cochlea supporting cells by factor of at least 10. By way of further example, in one such embodiment the composition has the capacity to increase the cell density of Lgr5+ supporting cells in an in vitro population of cochlea supporting cells by factor of at least 100, at least 500, at least 1,000 or even at least 2,000. Increases in the cell density of Lgr5+ supporting cells may also be observed for in vivo populations but the observed increase may be somewhat more modest. For example, in one embodiment the composition has the capacity to increase the cell density of Lgr5+ supporting cells in an in vivo population of cochlea supporting cells by at least 5%. By way of further example, in one such embodiment the composition has the capacity to increase the cell density of Lgr5+ supporting cells in an in vivo population of cochlea supporting cells by at least 10%. By way of further example, in one such embodiment the composition has the capacity to increase the cell density of Lgr5+ supporting cells in an in vivo population of cochlea supporting cells by at least 20%. By way of further example, in one such embodiment the composition has the capacity to increase the cell density of Lgr5+ supporting cells in an in vivo population of cochlea supporting cells by at least 30%. The capacity of the composition for such an increase in Lgr5+ supporting cells in an in vitro population may be demonstrated, for example, in a Stem Cell Proliferation Assay or in an appropriate in vivo assay. In one embodiment, a composition of the present disclosure has the capacity to increase the number of Lgr5+ cells in the cochlea by inducing expression of Lgr5 in cells with absent or low detection levels of the protein, while maintaining Native Morphology. In one embodiment, a composition of the present disclosure has the capacity to increase the number of Lgr5+ cells in the cochlea by inducing expression of Lgr5 in cells with absent or low detection levels of the protein, while maintaining Native Morphology and without producing Cell Aggregates.

In addition to increasing the cell density of Lgr5+ supporting cells, in one embodiment the method of the present disclosure has the capacity to increase the ratio of Lgr5+ cells to hair cells in a cochlear cell population. In one embodiment, the number of Lgr5+ supporting cells in an initial cochlear cell population is selectively expanded by treating the initial cochlear cell population with a composition of the present disclosure to form an expanded cell population and wherein the number of Lgr5+ supporting cells in the expanded cochlear cell population at least equals the number of hair cells. The expanded cochlear cell population may be, for example, an in vivo population, an in vitro population or even an in vitro explant. In one such embodiment, the ratio of Lgr5+ supporting cells to hair cells in the expanded cochlear cell population is at least 1:1. For example, in one such embodiment the ratio of Lgr5+ supporting cells to hair cells in the expanded cochlear cell population is at least 1.5:1. By way of further example, in one such embodiment the ratio of Lgr5+ supporting cells to hair cells in the expanded cochlear cell population is at least 2:1. By way of further example, in one such embodiment the ratio of Lgr5+ supporting cells to hair cells in the expanded cochlear cell population is at least 3:1. By way of further example, in one such embodiment the ratio of Lgr5+ supporting cells to hair cells in the expanded cochlear cell population is at least 4:1. By way of further example, in one such embodiment the ratio of Lgr5+ supporting cells to hair cells in the expanded cochlear cell population is at least 5:1. In each of the foregoing embodiments, the capacity of the composition of the present disclosure to expand a cochlear cell population as described in this paragraph may be determined by means of a Stem Cell Proliferation Assay.

In certain embodiments, the method increases the fraction of the Lgr5+ cells to total cells on the sensory epithelium by at least 10%, 20%, 50%, 100%, 250% 500%, 1,000% or 5000%.

In certain embodiments, the method increases the Lgr5+ cells until they become at least 10, 20, 30, 50, 70, or 85% of the cells on the sensory epithelium, e.g., the Organ of Corti.

In general, excessive proliferation of supporting cells in the cochlea is avoided. In one embodiment, the method of the present disclosure has the capacity to expand a cochlear cell population without creating a protrusion of new cells beyond the native surface of the cochlea, e.g., a Cell Aggregate. In some embodiments, 30 days after placing a composition comprising the composition comprising the salt of Formula I on the round or oval window membrane, the cochlear tissue has Native Morphology. In some embodiments, 30 days after placing the composition on the round or oval window membrane, the cochlear tissue has Native Morphology and lacks Cell Aggregates. In some embodiments, 30 days after placing the composition on the round or oval window membrane, the cochlear tissue has Native Morphology and at least 10, 20, 30, 50, 75, 90, 95, 98, or even at least 99% of the Lgr5+ cells in the Organ of Corti are not part of Cell Aggregates.

In addition to expanding supporting cell populations, generally, and Lgr5+ supporting cells, specifically, as described above, the method of the present disclosure has the capacity to maintain, in the daughter cells, the capacity to differentiate into hair cells. In in vivo populations, the maintenance of this capacity may be indirectly observed by an improvement in a subject's hearing. In in vitro populations, the maintenance of this capacity may be directly observed by an increase in the number of hair cells relative to a starting population or indirectly by measuring LGR5 activity, SOX2 activity or one or more of the other stem cell markers identified elsewhere herein.

In one embodiment, the capacity of the method to increase the stemness of a population of cochlear supporting cells, in general, or a population of Lgr5+ supporting cells, in particular, may be correlated with an increase of Lgr5 activity of an in vitro population of isolated Lgr5+ cells as determined by an Lgr5 Activity Assay. As previously noted, in one such embodiment, the composition has the capacity to increase the Lgr5 activity of stem cells in the intermediate cell population by a factor of 5 on average relative to the Lgr5 activity of the cells in the initial cell population. By way of further example, in one such embodiment the method has the capacity to increase the Lgr5 activity of the stem cells genes in the intermediate cell population by a factor of 10 relative to the Lgr5 activity of the cells in the initial cell population. By way of further example, in one such embodiment the method has the capacity to increase the Lgr5 activity of the stem cells in the intermediate cell population by a factor of 100 relative to the Lgr5 activity of the cells in the initial cell population. By way of further example, in one such embodiment the method has the capacity to increase the Lgr5 activity of the stem cells in the intermediate cell population by a factor of 1000 relative to the Lgr5 activity of the cells in the initial cell population. In each of the foregoing embodiments, the increase in the activity of stem cells in the cell population may be determined in vitro by immunostaining or endogenous fluorescent protein expression for target genes and analysis of their relative intensities via imaging analysis or flowcytometry, or using qPCR for target stem cell genes. The identity of the resulting stem cell population may optionally be further determined by stem cell assays including stem cell marker expression assay, colony forming assay, self-renewal assay and differentiation assay as defined in Stem cell assay.

In some embodiments, the method applied to an adult mammal produces a population of adult mammalian Lgr5$^+$ cells that are in S-phase.

In one embodiment, after applying the composition comprising the composition comprising the salt of Formula I to the round or oval window of a mouse, the in vivo Lgr5$^+$ Activity of a cell population in the Organ of Corti increases 1.3×, 1.5×, up to 20× over baseline for a population that has not been exposed to the composition. In some embodiments, applying the composition to the round or oval window of a mouse increases the average In vivo Lgr5$^+$ Activity for cells in the Organ of Corti is increased 1.3×, 1.5×, up to 20× over baseline for a population that has not been exposed to the composition.

In certain embodiments, the method increases the Lgr5$^+$ cells until they become at least 10%, 7.5%, 10%, up to 100% of the supporting cell population by number.

In certain embodiments, the composition has the capacity to increase the percentage of Lgr5$^+$ cell in a cochlea by 5%, 10%, 25%, 50%, or 80%.

In certain embodiments, the stem cell population is of an in vivo subject, and the method is a treatment for hearing loss and/or vestibular dysfunction (e.g., wherein the generation of inner ear hair cells from the expanded population of stem cells results in partial or full recovery of hearing loss and/or improved vestibular function). In certain embodiments, the stem cell population is of an in vivo subject, and the method further comprises delivering a drug to the subject (e.g., for treatment of a disease and/or disorder unrelated to hearing loss and/or vestibular dysfunction) at a higher concentration than a known safe maximum dosage of the drug for the subject (e.g., the known safe maximum dosage if delivered in the absence of the generation of inner ear hair cells resulting from the method) (e.g., due to a reduction or elimination of a dose-limiting ototoxicity of the drug).

In certain embodiments, the method further comprises performing high throughput screening using the generated inner ear hair cells. In certain embodiments, the method comprises using the generated inner ear hair cells to screen molecules for toxicity against inner ear hair cells. In certain embodiments, the method comprises using the generated inner ear hair cells to screen molecules for ability to improve survival of inner ear hair cells (e.g., inner ear hair cells exposed to said molecules).

In another aspect, the disclosure is directed to a method of producing an expanded population of stem cells, the method comprising: administering or causing to be administered to a stem cell population (e.g., of an in vitro, ex vivo, or in vivo sample/subject) a composition comprising the composition comprising the salt of Formula I.

In certain embodiments, the administering step is carried out by performing one or more injections into the ear (e.g., transtympanically into the middle ear and/or inner ear).

In certain embodiments, the administering step comprises administering the GSK3-beta inhibitor and/or Wnt agonist in a sustained manner.

In certain embodiments, the stem cells are inner ear stem cells and/or supporting cells.

In certain embodiments, the method further comprises performing high throughput screening using the generated expanded population of stem cells. In certain embodiments, the method further comprises using the generated stem cells to screen molecules for toxicity against stem cells and/or their progeny. In certain embodiments, the method comprises using the generated stem cells to screen molecules for ability to improve survival of stem cells and/or their progeny.

In another aspect, the disclosure is directed to a method of treating a subject who has, or is at risk of developing, hearing loss and/or vestibular dysfunction, the method comprising: identifying a subject who has experienced, or is at risk for developing, hearing loss and/or vestibular dysfunction, administering or causing to be administered a composition comprising any of the compositions or compounds provided herein.

In certain embodiments, the stem cell population comprises Lgr5$^+$ cells. In certain embodiments, the stem cell population comprises post-natal cells. In certain embodiments, the stem cell population comprises epithelial stem cells. In certain embodiments, stem cells include progenitor cells.

In certain embodiments, the step of administering is carried out by performing one or more injections into the ear (e.g., transtympanically into the middle ear and/or inner ear).

In another aspect, the disclosure is directed to a method of generating inner ear hair cells, the method comprising: proliferating stem cells in an initial stem cell population (e.g., of an in vitro, ex vivo, or in vivo sample/subject), resulting in an expanded population of stem cells (e.g., such that the expanded population is a factor of at least 1.25, 1.5, 1.75, 2, 3, 5, 10, or 20 greater than the initial stem cell population); and facilitating generation of inner ear hair cells from the expanded population of stem cells.

In another aspect, the disclosure is directed to a method of generating inner ear hair cells, the method comprising administering a composition comprising the composition comprising the salt of Formula I (e.g., in a pharmaceutically acceptable form (e.g., salt)) to a cell population in an inner ear of a subject, thereby facilitating generation of inner ear hair cells.

In another aspect, the disclosure is directed to a method of generating inner ear hair cells, the method comprising: proliferating post-natal LGR5+ cells in an initial population (e.g., of an in vitro, ex vivo, or in vivo sample/subject), resulting in an expanded population of LGR5+ cells (e.g., such that the expanded population is a factor of at least 1.25, 1.5, 1.75, 2, 3, 5, 10, or 20 greater than the initial stem cell population), said expanded population of LGR5+ cells resulting in generation of inner ear hair cells. In certain embodiments, stem cells include progenitor cells.

In another aspect, the disclosure is directed to a method of treating a disease or disorder, the method comprising: proliferating post-natal Lgr5+ epithelial cells in an initial population of a subject (in vivo), resulting in an expanded population of Lgr5+ epithelial cells (e.g., such that the expanded population is a factor of at least 1.25, 1.5, 1.75, 2, 3, 5, 10, or 20 greater than the initial post-natal Lgr5+ epithelial cell population).

In some embodiments, Lgr5+ cells are differentiated into hair cells.

In some embodiments of the compositions described herein, the Wnt agonist, GSK-3 alpha inhibitor or GSK-3 beta inhibitor is used at a concentration of about 0.01 uM to about 1,000 mM and optionally in combination with other agents. In other embodiments, the Wnt agonist, GSK-3 alpha inhibitor or GSK-3 beta inhibitor is used at a concentration of about 0.1 uM to about 1,000 mM and optionally in combination with other agents. In other embodiments, the Wnt agonist, GSK-3 alpha inhibitor or GSK-3 beta inhibitor is used at a concentration of about 1 uM to about 100 mM and optionally in combination with other agents. In other embodiments, the Wnt agonist, GSK-3 alpha inhibitor or GSK-3 beta inhibitor is used at a concentration of about 10 uM to about 10 mM and optionally in combination with other agents. In other embodiments, the Wnt agonist, GSK-3 alpha inhibitor or GSK-3 beta inhibitor is used at a concentration of about 1 uM to about 10 uM and optionally in combination with other agents. In other embodiments, the Wnt agonist, GSK-3 alpha inhibitor or GSK-3 beta inhibitor is used at a concentration of about 10 uM to about 100 uM and optionally in combination with other agents. In other embodiments, the Wnt agonist, GSK-3 alpha inhibitor or GSK-3 beta inhibitor is used at a concentration of about 100 uM to about 1000 uM and optionally in combination with other agents. In other embodiments, the Wnt agonist, GSK-3 alpha inhibitor or GSK-3 beta inhibitor is used at a concentration of about 1 mM to about 10 mM and optionally in combination with other agents. In other embodiments, the Wnt agonist, GSK-3 alpha inhibitor or GSK-3 beta inhibitor is used at a concentration of about 10 mM to about 100 mM and optionally in combination with other agents.

In some embodiments of the compositions described herein, the GSK-3 inhibitor is CHIR99021 used at a concentration of about 1 uM to about 1,000 mM and optionally in combination with other agents. In other embodiments, the GSK-3 inhibitor is CHIR99021 used at a concentration of about 10 uM to about 100 mM and optionally in combination with other agents. In other embodiments, the GSK-3 inhibitor is CHIR99021 used at a concentration of about 100 uM to about 100 mM and optionally in combination with other agents. In other embodiments, the GSK-3 inhibitor is CHIR99021 used at a concentration of about 1 mM to about 10 mM and optionally in combination with other agents.

In some embodiments of the compositions described herein, the GSK-3 inhibitor is LY2090314 used at a concentration of about 0.01 uM to about 1,000 mM and optionally in combination with other agents. In other embodiments, the GSK-3 inhibitor is LY2090314 used at a concentration of about 0.1 uM to about 10 mM and optionally in combination with other agents. In other embodiments, the GSK-3 inhibitor is LY2090314 used at a concentration of about 1 uM to about 1 mM and optionally in combination with other agents. In other embodiments, the GSK-3 inhibitor is LY2090314 used at a concentration of about 1 uM to about 100 uM and optionally in combination with other agents. In other embodiments, the GSK-3 inhibitor is LY2090314 used at a concentration of about 10 uM and optionally in combination with other agents.

In some embodiments of the compositions described herein, the GSK-3 inhibitor is GSK inhibitor XXII used at a concentration of about 0.1 uM to about 1,000 mM and optionally in combination with other agents. In other embodiments, the GSK-3 inhibitor is GSK inhibitor XXII used at a concentration of about 1 uM to about 100 mM and optionally in combination with other agents. In other embodiments, the GSK-3 inhibitor is GSK inhibitor XXII used at a concentration of about 10 uM to about 10 mM and optionally in combination with other agents. In other embodiments, the GSK-3 inhibitor is GSK inhibitor XXII used at a concentration of about 100 uM to about 10 mM and optionally in combination with other agents. In other embodiments, the GSK-3 inhibitor is GSK inhibitor XXII used at a concentration of about 100 uM to about 1 mM and optionally in combination with other agents.

In some embodiments of the compositions described herein, the GSK-3 inhibitor is AZD 1080 used at a concentration of about 0.1 uM to about 1,000 mM and optionally in combination with other agents. In other embodiments, the GSK-3 inhibitor is AZD 1080 used at a concentration of about 1 uM to about 1,000 mM and optionally in combination with other agents. In other embodiments, the GSK-3 inhibitor is AZD 1080 used at a concentration of about 10 uM to about 100 mM and optionally in combination with other agents. In other embodiments, the GSK-3 inhibitor is AZD 1080 used at a concentration of about 100 uM to about 10 mM and optionally in combination with other agents. In other embodiments, the GSK-3 inhibitor is AZD 1080 used at a concentration of about 1 mM to about 10 mM and optionally in combination with other agents.

In some embodiments of the compositions described herein, the HDAC inhibitor is used at a concentration of about 0.01 uM to about 100,000 mM and optionally in combination with other agents. In other embodiments, the HDAC inhibitor is used at a concentration of about 1 uM to about 10,000 mM and optionally in combination with other agents. In other embodiments, the HDAC inhibitor is used at a concentration of about 10 uM to about 10000 mM and optionally in combination with other agents. In other embodiments, the HDAC inhibitor is used at a concentration of about 100 uM to about 1000 mM and optionally in combination with other agents. In other embodiments, the HDAC inhibitor is used at a concentration of about 1 uM to about 10 uM and optionally in combination with other agents. In other embodiments, the HDAC inhibitor is used at a concentration of about 10 uM to about 100 uM and optionally in combination with other agents. In other embodiments, the HDAC inhibitor is used at a concentration of about 100 uM to about 1000 uM and optionally in combination with other agents. In other embodiments, the HDAC inhibitor is used at a concentration of about 1000 uM to about 10 mM and optionally in combination with other agents. In other embodiments, the HDAC inhibitor is used at a concentration of about 10 mM to about 100 mM and optionally in combination with other agents. In other embodiments, the HDAC inhibitor is used at a concentration of about 100 mM to about 1000 mM and optionally in combination with other agents. In other embodiments, the HDAC inhibitor is used at a concentration of about 1000 mM to about 10,000 mM and optionally in combination with other agents.

In some embodiments of the compositions described herein, the HDAC inhibitor is Valproic Acid used at a concentration of about 10 uM to about 100,000 mM and optionally in combination with other agents. In other embodiments, the HDAC inhibitor is Valproic Acid used at a concentration of about 1 mM to about 10,000 mM and optionally in combination with other agents. In other embodiments, the HDAC inhibitor is Valproic Acid used at a concentration of about 10 mM to about 10,000 mM and optionally in combination with other agents. In other embodiments, the HDAC inhibitor is Valproic Acid used at a concentration of about 100 mM to about 10,000 mM and optionally in combination with other agents. In other embodiments, the HDAC inhibitor is Valproic Acid used at a concentration of about 200 mM to about 2,000 mM and optionally in combination with other agents. In other embodiments, the HDAC inhibitor is Valproic Acid used at a concentration of about 1,000 mM and optionally in combination with other agents.

In some embodiments of the compositions described herein, the Wnt agonist, GSK-3 alpha inhibitor, or GSK-3 beta inhibitor is used at a concentration ratio of about 0.01 to about 1,000,000-fold the activity in Effective Stemness Driver Concentration and optionally in combination with other agents. In other embodiments, the Wnt agonist, GSK-3 alpha inhibitor, or GSK-3 beta inhibitor is used at a concentration ratio of about 0.1 to about 100,000-fold the Effective Stemness Driver Concentration and optionally in combination with other agents. In other embodiments, the Wnt agonist, GSK-3 alpha inhibitor, or GSK-3 beta inhibitor is used at a concentration ratio of about 1 to about 10,000-fold the Effective Stemness Driver Concentration and optionally in combination with other agents. In other embodiments, the Wnt agonist, GSK-3 alpha inhibitor, or GSK-3 beta inhibitor is used at a concentration ratio of about 100 to about 5000-fold the Effective Stemness Driver Concentration and optionally in combination with other agents. In other embodiments, the Wnt agonist, GSK-3 alpha inhibitor, or GSK-3 beta inhibitor is used at a concentration ratio of about 50 to about 2000-fold the Effective Stemness Driver Concentration and optionally in combination with other agents. In other embodiments, the Wnt agonist, GSK-3 alpha inhibitor, or GSK-3 beta inhibitor is used at a concentration ratio of about 100 to about 1000-fold the Effective Stemness Driver Concentration and optionally in combination with other agents. In other embodiments, the Wnt agonist, GSK-3 alpha inhibitor, or GSK-3 beta inhibitor is used at a concentration ratio of about 1,000-fold the Effective Stemness Driver Concentration and optionally in combination with other agents.

In some embodiments of the compositions described herein, the HDAC inhibitor is used at a concentration ratio of about 0.1 to about 1,000,000-fold the Effective Concentration and optionally in combination with other agents. In other embodiments, the HDAC inhibitor is used at a concentration ratio of about 1 to about 100,000-fold the Effective Concentration and optionally in combination with other agents. In other embodiments, the HDAC inhibitor is used at a concentration ratio of about 10 to about 10,000-fold the Effective Concentration and optionally in combination with other agents. In other embodiments, the HDAC inhibitor is used at a concentration ratio of about 100 to about 1000-fold the Effective Concentration and optionally in combination with other agents. In other embodiments, the HDAC inhibitor is used at a concentration ratio of about 1,000-fold the Effective Concentration and optionally in combination with other agents.

In some embodiments of the compositions described herein, the Wnt agonist, GSK-3 alpha inhibitors or GSK-3 beta inhibitor is used at a concentration of about 0.01 nM to about 1,000 uM and optionally in combination with other agents. In other embodiments, the Wnt agonist, GSK-3 alpha inhibitors or GSK-3 beta inhibitor is used at a concentration of about 0.1 nM to about 1,000 uM and optionally in combination with other agents. In other embodiments, the Wnt agonist, GSK-3 alpha inhibitors or GSK-3 beta inhibitor is used at a concentration of about 1 nM to about 100 uM and optionally in combination with other agents. In other embodiments, the Wnt agonist, GSK-3 alpha inhibitors or GSK-3 beta inhibitor is used at a concentration of about 10 nM to about 10 uM and optionally in combination with other agents. In other embodiments, the Wnt agonist, GSK-3 alpha inhibitors or GSK-3 beta inhibitor is used at a concentration of about 1 nM to about 10 nM and optionally in combination with other agents. In other embodiments, the Wnt agonist, GSK-3 alpha inhibitors or GSK-3 beta inhibitor is used at a concentration of about 10 nM to about 100 nM and optionally in combination with other agents. In other embodiments, the Wnt agonist, GSK-3 alpha inhibitors or GSK-3 beta inhibitor is used at a concentration of about 100 nM to about 1000 nM and optionally in combination with other agents. In other embodiments, the Wnt agonist, GSK-3 alpha inhibitors or GSK-3 beta inhibitor is used at a concentration of about 1 uM to about 10 uM and optionally in combination with other agents. In other embodiments, the Wnt agonist, GSK-3 alpha inhibitors or GSK-3 beta inhibitor is used at a concentration of about 10 uM to about 100 uM and optionally in combination with other agents.

In some embodiments of the compositions described herein, the GSK-3 inhibitor is CHIR99021 used at a concentration of about 1 nM to about 1,000 uM and optionally in combination with other agents. In other embodiments, the GSK-3 inhibitor is CHIR99021 used at a concentration of about 10 nM to about 100 uM and optionally in combination with other agents. In other embodiments, the GSK-3 inhibitor is CHIR99021 used at a concentration of about 100 nM to about 100 uM and optionally in combination with other agents. In other embodiments, the GSK-3 inhibitor is CHIR99021 used at a concentration of about 1 uM to about 10 uM and optionally in combination with other agents.

In some embodiments of the compositions described herein, the GSK-3 inhibitor is LY2090314 used at a concentration of about 0.01 nM to about 1,000 uM and optionally in combination with other agents. In other embodiments, the GSK-3 inhibitor is LY2090314 used at a concentration of about 0.1 nM to about 10 uM and optionally in combination with other agents. In other embodiments, the GSK-3 inhibitor is LY2090314 used at a concentration of about 1 nM to about 1 uM and optionally in combination with other agents. In other embodiments, the GSK-3 inhibitor is LY2090314 used at a concentration of about 1 nM to about 100 nM and optionally in combination with other agents. In other embodiments, the GSK-3 inhibitor is LY2090314 used at a concentration of about 10 nM and optionally in combination with other agents.

In some embodiments of the compositions described herein, the GSK-3 inhibitor is GSK inhibitor XXII used at a concentration of about 0.1 nM to about 1,000 uM and optionally in combination with other agents. In other embodiments, the GSK-3 inhibitor is GSK inhibitor XXII used at a concentration of about 1 nM to about 100 uM and optionally in combination with other agents. In other embodiments, the GSK-3 inhibitor is GSK inhibitor XXII used at a concentration of about 10 nM to about 10 uM and optionally in combination with other agents. In other embodiments, the GSK-3 inhibitor is GSK inhibitor XXII used at a concentration of about 100 nM to about 1 uM and optionally in combination with other agents.

In some embodiments of the compositions described herein, the GSK-3 inhibitor is AZD 1080 used at a concentration of about 1 nM to about 1,000 uM and optionally in combination with other agents. In other embodiments, the GSK-3 inhibitor is AZD 1080 used at a concentration of about 10 nM to about 1,000 uM and optionally in combination with other agents. In other embodiments, the GSK-3 inhibitor is AZD 1080 used at a concentration of about 100 nM to about 100 uM and optionally in combination with other agents. In other embodiments, the GSK-3 inhibitor is AZD 1080 used at a concentration of about 1 uM to about 10 uM and optionally in combination with other agents.

In some embodiments of the compositions described herein, the HDAC inhibitor is used at a concentration of about 0.01 nM to about 100,000 uM and optionally in combination with other agents. In other embodiments, the HDAC inhibitor is used at a concentration of about 1 nM to about 10,000 uM and optionally in combination with other agents. In other embodiments, the HDAC inhibitor is used at a concentration of about 10 nM to about 10,000 uM and optionally in combination with other agents. In other embodiments, the HDAC inhibitor is used at a concentration of about 100 nM to about 1000 uM and optionally in combination with other agents. In other embodiments, the HDAC inhibitor is used at a concentration of about 1 nM to about 10 nM and optionally in combination with other agents. In other embodiments, the HDAC inhibitor is used at a concentration of about 10 nM to about 100 nM and optionally in combination with other agents. In other embodiments, the HDAC inhibitor is used at a concentration of about 100 nM to about 1000 nM and optionally in combination with other agents. In other embodiments, the HDAC inhibitor is used at a concentration of about 1 uM to about 10 uM and optionally in combination with other agents. In other embodiments, the HDAC inhibitor is used at a concentration of about 10 uM to about 100 uM and optionally in combination with other agents. In other embodiments, the HDAC inhibitor is used at a concentration of about 100 uM to about 1000 uM and optionally in combination with other agents. In other embodiments, the HDAC inhibitor is used at a concentration of about 1,000 uM to about 10,000 uM and optionally in combination with other agents.

In some embodiments of the compositions described herein, the HDAC inhibitor is Valproic Acid used at a concentration of about 10 nM to about 100,000 uM and optionally in combination with other agents. In other embodiments, the HDAC inhibitor is Valproic Acid used at a concentration of about 1 uM to about 10,000 uM and optionally in combination with other agents. In other embodiments, the HDAC inhibitor is Valproic Acid used at a concentration of about 10 uM to about 10,000 uM and optionally in combination with other agents. In other embodiments, the HDAC inhibitor is Valproic Acid used at a concentration of about 100 uM to about 10,000 uM and optionally in combination with other agents. In other embodiments, the HDAC inhibitor is Valproic Acid used at a concentration of about 200 uM to about 2,000 uM and optionally in combination with other agents. In other embodiments, the HDAC inhibitor is Valproic Acid used at a concentration of about 1,000 uM and optionally in combination with other agents.

Administration

The membrane of the round or oval window is the biological barrier to the inner ear space and represents the major obstacle for the local treatment of hearing impairment. The administered drug must overcome this membrane to reach the inner ear space. The drug can operatively (e.g., injection through the tympanic membrane) be placed locally to the round or oval window membrane and can then penetrate through the round or oval window membrane. Substances that penetrate the round or oval window typically distribute in the perilymph and thus reach the hair cells and supporting cells.

In certain embodiments, pharmaceutical compositions are adapted to administer the drug locally to the round or oval window membrane. The pharmaceutical compositions may also contain a membrane penetration enhancer, which supports the passage of the agents mentioned herein through the round or oval window membrane. Accordingly, liquid, gel or foam compositions may be used. It is also possible to apply the active ingredient orally or to employ a combination of delivery approaches.

Intratympanic (IT) delivery of drugs to the ear is increasingly used for both clinical and research purposes. Some groups have applied drugs in a sustained manner using microcatheters and microwicks, while the majority have applied them as single or as repeated IT injections (up to 8 injections over periods of up to 2 weeks) 8.

Intratympanically applied drugs are thought to enter the fluids of the inner ear primarily by crossing the round or oval window (RW) membrane. Calculations show that a major factor controlling both the amount of drug entering the ear and the distribution of drug long the length of the ear is the duration the drug remains in the middle ear space. Single, 'one-shot' applications or applications of aqueous solutions for few hours' duration result in steep drug gradients for the applied substance along the length of the cochlea and rapidly declining concentration in the basal turn of the cochlea as the drug subsequently becomes distributed throughout the ear.

Other injection approaches include by osmotic pump, or, by combination with implanted biomaterial, by injection or infusion. Biomaterials that can aid in controlling release kinetics and distribution of drug include hydrogel materials, degradable materials. One class of materials that is used includes in situ gelling materials. All potential materials and methodologies mentioned in these references are included herein by reference (Almeida H, Amaral M H, Lobao P, Lobo J M. In situ gelling systems: a strategy to improve the bioavailability of ophthalmic pharmaceutical compositions. *Drug Discovery Today* 2014; 19:400-12; Wise A K, Gillespie L N. Drug delivery to the inner ear. *Journal of Neural Engineering* 2012; 9:065002; Surovtseva E V, Johnston A H, Zhang W, et al. Prestin binding peptides as ligands for targeted polymersome mediated drug delivery to outer hair cells in the inner ear. *International Journal of Pharmaceutics* 2012; 424:121-7; Roy S, Glueckert R, Johnston A H, et al. Strategies for drug delivery to the human inner ear by multifunctional nanoparticles. *Nanomedicine* 2012; 7:55-63; Rivera T, Sanz L, Camarero G, Varela-Nieto I. Drug delivery to the inner ear: strategies and their therapeutic implications for sensorineural hearing loss. *Current Drug Delivery* 2012; 9:231-42; Pararas E E, Borkholder D A, Borenstein J T. Microsystems technologies for drug delivery to the inner ear. Advanced drug delivery reviews 2012; 64:1650-60; Li M L, Lee L C, Cheng Y R, et al. A novel aerosol-mediated drug delivery system for inner ear therapy: intratympanic aerosol methylprednisolone can attenuate acoustic trauma. *IEEE Transactions on Biomedical Engineering* 2013; 60:2450-60; Lajud S A, Han Z, Chi F L, et al. A regulated delivery system for inner ear drug application. *Journal of controlled release: official journal of the Controlled Release*

*Society* 2013; 166:268-76; Kim D K, Park S N, Park K H, et al. Development of a drug delivery system for the inner ear using poly(amino acid)-based nanoparticles. *Drug delivery* 2014; Kanzaki S, Fujioka M, Yasuda A, et al., *PloS ONE* 2012; 7:e48480; Engleder E, Honeder C, Klobasa J, Wirth M, Arnoldner C, Gabor F. Preclinical evaluation of thermoreversible triamcinolone acetonide hydrogels for drug delivery to the inner ear. *International Journal of Pharmaceutics* 2014; 471:297-302; Bohl A, Rohm H W, Ceschi P, et al. Development of a specially tailored local drug delivery system for the prevention of fibrosis after insertion of cochlear implants into the inner ear. *Journal of Materials Science: Materials in Medicine* 2012; 23:2151-62; Hoskison E, Daniel M, Al-Zahid S, Shakesheff K M, Bayston R, Birchall J P. Drug delivery to the ear. *Therapeutic Delivery* 2013; 4:115-24; Staecker H, Rodgers B., *Expert Opin Drug Deliv* 2013; 10:639-50; Pritz C O, Dudas J, Rask-Andersen H, Schrott-Fischer A, Glueckert R. Nanomedicine strategies for drug delivery to the ear. *Nanomedicine* 2013; 8:1155-72), which are included herein by reference in their entirety. Other materials include collagen or other natural materials including fibrin, gelatin, and decellularized tissues. Gelfoam may also be suitable.

Delivery may also be enhanced via alternate means including but not limited to agents added to the delivered composition such as penetration enhancers, or could be through devices via ultrasound, electroporation, or high speed jet.

Methods described herein can also be used for inner ear cell types that may be produced using a variety of methods know to those skilled in the art including those cell types described in PCT Application No. WO2012103012 A1.

With regard to human and veterinary treatment, the amount of a particular agent(s) that is administered may be dependent on a variety of factors, including the disorder being treated and the severity of the disorder; activity of the specific agent(s) employed; the age, body weight, general health, sex and diet of the patient; the time of administration, route of administration, and rate of excretion of the specific agent(s) employed; the duration of the treatment; drugs used in combination or coincidental with the specific agent(s) employed; the judgment of the prescribing physician or veterinarian; and like factors known in the medical and veterinary arts.

The agents described herein may be administered in a therapeutically effective amount to a subject in need of treatment. Administration of compositions described herein can be via any of suitable route of administration, particularly by intratympanically. Other routes include ingestion, or alternatively parenterally, for example intravenously, intra-arterially, intraperitoneally, intrathecally, intraventricularly, intraurethrally, intrasternally, intracranially, intramuscularly, intranasally, subcutaneously, sublingually, transdermally, or by inhalation or insufflations, or topical by ear instillation for absorption through the skin of the ear canal and membranes of the eardrum. Such administration may be as a single or multiple oral doses, defined number of ear drops, or a bolus injection, multiple injections, or as a short- or long-duration infusion. Implantable devices (e.g., implantable infusion pumps) may also be employed for the periodic parenteral delivery over time of equivalent or varying dosages of the particular composition. For such parenteral administration, the composition s are formulated as a sterile solution in water or another suitable solvent or mixture of solvents. The solution may contain other substances such as salts, sugars (particularly glucose or mannitol), to make the solution isotonic with blood, buffering agents such as acetic, citric, and/or phosphoric acids and their sodium salts, and preservatives. The preparation of suitable and sterile parenteral compositions is described in detail in the section entitled "Compositions" above.

Compositions described herein can be administered by a number of methods sufficient to deliver the composition to the inner ear. Delivering a composition to the inner ear includes administering the composition to the middle ear, such that the composition may diffuse across the round or oval window to the inner ear and administering a composition to the inner ear by direct injection through the round or oval window membrane. Such methods include, but are not limited to auricular administration, by transtympanic wicks or catheters, or parenteral administration, for example, by intraauricular, transtympanic, or intracochlear injection.

In particular embodiments, the compositions and compositions of the disclosure are locally administered, meaning that they are not administered systemically.

In one embodiment, a syringe and needle apparatus is used to administer compositions to a subject using auricular administration. A suitably sized needle is used to pierce the tympanic membrane and a wick or catheter comprising the composition is inserted through the pierced tympanic membrane and into the middle ear of the subject. The device may be inserted such that it is in contact with the round or oval window or immediately adjacent to the round or oval window. Exemplary devices used for auricular administration include, but are not limited to, transtympanic wicks, transtympanic catheters, round or oval window microcatheters (small catheters that deliver medicine to the round or oval window), and Silverstein Microwicks™ (small tube with a "wick" through the tube to the round or oval window, allowing regulation by subject or medical professional).

In another embodiment, a syringe and needle apparatus is used to administer compositions to a subject using transtympanic injection, injection behind the tympanic membrane into the middle and/or inner ear. The composition may be administered directly onto the round or oval window membrane via transtympanic injection or may be administered directly to the cochlea via intracochlear injection or directly to the vestibular organs via intravestibular injection.

In some embodiments, the delivery device is an apparatus designed for administration of compositions to the middle and/or inner ear. By way of example only: GYRUS Medical Gmbh offers micro-otoscopes for visualization of and drug delivery to the round or oval window niche; Arenberg has described a medical treatment device to deliver fluids to inner ear structures in U.S. Pat. Nos. 5,421,818; 5,474,529; and 5,476,446, each of which is incorporated by reference herein for such disclosure. U.S. patent application Ser. No. 08/874,208, which is incorporated herein by reference for such disclosure, describes a surgical method for implanting a fluid transfer conduit to deliver compositions to the inner ear. U.S. Patent Application Publication 2007/0167918, which is incorporated herein by reference for such disclosure, further describes a combined otic aspirator and medication dispenser for transtympanic fluid sampling and medicament application.

In some embodiments, a composition disclosed herein is administered to a subject in need thereof once. In some embodiments, a composition disclosed herein is administered to a subject in need thereof more than once. In some embodiments, a first administration of a composition disclosed herein is followed by a second, third, fourth, or fifth administration of a composition disclosed herein.

The number of times a composition is administered to a subject in need thereof depends on the discretion of a medical professional, the disorder, the severity of the disorder, and the subject's response to the composition. In some embodiments, a composition disclosed herein is administered once to a subject in need thereof with a mild acute condition. In some embodiments, a composition disclosed herein is administered more than once to a subject in need thereof with a moderate or severe acute condition. In the case wherein the subject's condition does not improve, upon the doctor's discretion the composition may be administered chronically, that is, for an extended period of time, including throughout the duration of the subject's life in order to ameliorate or otherwise control or limit the symptoms of the subject's disease or condition.

In the case wherein the subject's status does improve, upon the doctor's discretion the composition may administered continuously; alternatively, the dose of drug being administered may be temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once the subject's hearing and/or balance has improved, a maintenance dose can be administered, if necessary. Subsequently, the dosage or the frequency of administration, or both, is optionally reduced, as a function of the symptoms, to a level at which the improved disease, disorder or condition is retained. In certain embodiments, subjects require intermittent treatment on a long-term basis upon any recurrence of symptoms

EXAMPLES

Example 1: Effects of Poloxamer and Valproate on CHIR99021 Dihydrochloride (diHCl)

A 23.75% (w/v) poloxamer solution was prepared in 1×PBS containing 1M (166.2 mg/ml) Valproic acid sodium salt, 5% (v/v) DMSO, and 2.77 mM (1.39 mg/ml) CHIR99021 freebase. The poloxamer was fully soluble in the solutions at this concentration and the solution retained fluidity at 4° C. as judged by passage through a micropipette with a 100 uM opening. The solution also retained poloxamer polymerization capacity at 37° C. as judged by gelling of 10 ul of solution pipetted onto coverglass warmed to 37° C. in less than 20 seconds. The final pH of this solution is around 9.

Example 2: Effects on Solubility at Various Concentrations of Poloxamer

P407 solubility was studied at 16.7%, 20%, 23.1%, 25.9%, 28.7%, 33.3%, 37.5%, 41.2%, and 50% w/w in 1M Valproic acid sodium salt and 5% dimethylsulfoxide (DMSO). Valproic acid sodium salt (NaVal) stock solution was prepared by dissolving 16.62 g Valproic acid sodium salt+5.0 g DMSO+78.37 g Water. Poloxamer 407 (P407) was weighed and added to containers containing 10 g each of the 1M Valproic acid sodium salt+5% w/w DMSO solution. The solutions were stored overnight in refrigerator at 0-2° C. and observed for any undissolved poloxamer. Poloxamer levels of up to 28.6% are acceptable when formulated with 1 M valproic acid sodium salt and 5% dimethyl sulfoxide.

Results

Figure 2:
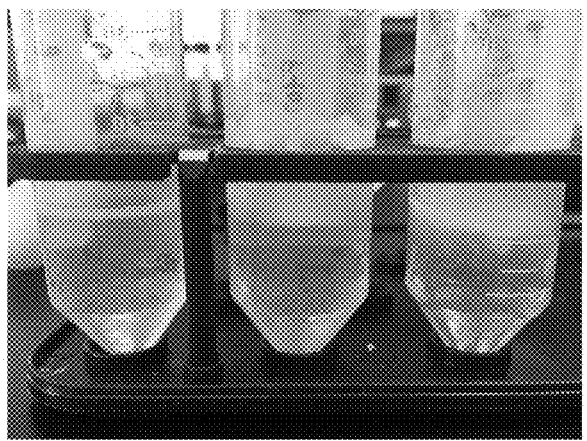
FIG. 2 is a photograph showing the solubility of Poloxamer 407 (P407) at 20% w/w, 23.1% w/w, and 25.9% w/w Poloxamer 407 in 1M Valproic acid sodium salt and 5% dimethylsulfoxide (DMSO). Percent w/w of P407 left to right as shown: 20% w/w, 23.1% w/w, and 25.9% w/w.

Samples at a concentration of 16.7% to 23.1% w/w P407 were clear and fluid in cold conditions while solutions at a concentration of 25.9% to 28.6% w/w P407 were clear but viscous. (FIGS. 1 and 2) Concentrations above 33.3% w/w P407 remained undissolved and formed a thick swollen mass. The results demonstrated that poloxamer levels of up to 28.6% are acceptable when formulated with 1 M valproic acid sodium salt and 5% dimethyl sulfoxide. Table 1 below shows the results and observations of the samples at various concentrations of P407.

TABLE 1

| Composition | % P407 (w/w) | 18+ Hours Observations | 40+ Hours Observations |
| --- | --- | --- | --- |
| 2 g P407; 10 g 1M NaVal and 5% DMSO Stock | 16.70% | Clear, dissolved solution | Clear, dissolved solution |
| 4 g P407; 10 g 1M NaVal and 5% DMSO Stock | 28.60% | Almost clear, small white globs | Clear, dissolved, viscous gel |
| 5 g P407; 10 g 1M NaVal and 5% DMSO Stock | 33.30% | Slightly swollen white glob | Swollen white glob |
| 6 g P407; 10 g 1M NaVal and 5% DMSO Stock | 37.50% | Swollen white glob | Swollen white glob |
| 7 g P407; 10 g 1M NaVal and 5% DMSO Stock | 41.20% | Swollen white glob | Swollen white glob |
| 10 g P407; 10 g 1M NaVal and 5% DMSO Stock | 50% | Extremely swollen white glob | Extremely swollen white glob |
| 2.5 g P407; 10 g 1M NaVal and 5% DMSO Stock | 20% | n/a | Clear, dissolved solution |
| 3 g P407; 10 g 1M NaVal and 5% DMSO Stock | 23.10% | n/a | Clear, dissolved solution |
| 3.5 g P407; 10 g 1M NaVal and 5% DMSO Stock | 25.90% | n/a | Clear, dissolved, slightly viscous solution |

From the foregoing description, it will be apparent that variations and modifications may be made to the invention described herein to adopt it to various usages and conditions. Methods and materials are described herein for use in the present invention; other, suitable methods and materials known in the art can also be used. The materials, methods, and examples are illustrative only and not intended to be limiting. Such embodiments are also within the scope of the following claims. The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof. The teachings of all patents, published applications and references cited herein are incorporated by reference in their entirety. While this invention has been particularly shown and described with references to example embodiments thereof, it will be understood by those skilled in the art that various changes in form and details may be made therein without departing from the scope of the invention encompassed by the appended claims

The invention claimed is:

1. A poloxamer containing pharmaceutical composition comprising:
    a) a 1,2,3,4-tetrahydro-[1,4]diazepino[6,7,1-hi]indole containing compound;
    b) Poloxamer 407 at a concentration of greater than or equal to 21 wt % of the pharmaceutical composition; and
    c) a carboxylic acid containing compound being valproic acid or a pharmaceutically acceptable salt thereof;
    wherein the pharmaceutical composition has a gelation temperature of greater than 10° C.

2. The pharmaceutical composition of claim 1, wherein the 1,2,3,4-tetrahydro-[1,4]diazepino[6,7,1-hi]indole containing compound is a 3-(1,2,3,4-tetrahydro-[1,4]diazepino[6,7,1-hi]indol-7-yl)-1H-pyrrole-2,5-dione containing compound.

3. The pharmaceutical composition of claim 1, wherein the 1,2,3,4-tetrahydro-[1,4]diazepino[6,7,1-hi]indole containing compound is a 3-(imidazo[1,2-a]pyridin-3-yl)-4-(1,2,3,4-tetrahydro-[1,4]diazepino[6,7,1-hi]indol-7-yl)-1H-pyrrole-2,5-dione containing compound.

4. The pharmaceutical composition of claim 1, wherein the 1,2,3,4-tetrahydro-[1,4]diazepino[6,7,1-hi]indole containing compound is 3-(9-fluoro-2-(piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione represented by Formula III or a pharmaceutically acceptable salt thereof:

Formula III

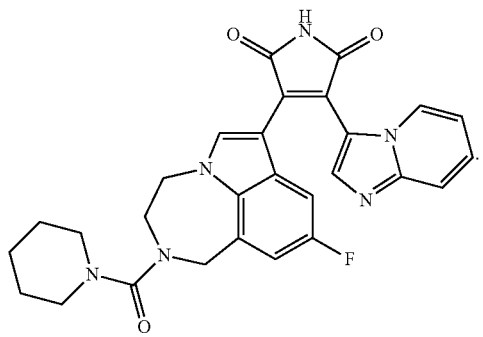

5. The pharmaceutical composition of claim 1, wherein the concentration of the Poloxamer 407 is between about 21 wt % and about 40 wt % relative to the pharmaceutical composition.

6. The pharmaceutical composition of claim 1, wherein the gelation temperature of the pharmaceutical composition is between about 11° C. and about 32° C.

7. The pharmaceutical composition of claim 1, wherein the carboxylic acid containing compound is the pharmaceutically acceptable salt of valproic acid.

8. The pharmaceutical composition of claim 1, wherein the carboxylic acid containing compound is valproic acid sodium salt.

9. The pharmaceutical composition of claim 1, wherein the Poloxamer 407 is in a concentration between about 21 wt % and about 30 wt %, between about 23 wt % and about 29 wt %, or between about 23 wt % and about 27 wt % relative to the pharmaceutical composition.

10. The pharmaceutical composition of claim 1, wherein the Poloxamer 407 is in a concentration of about 25 wt % relative to the pharmaceutical composition.

11. The pharmaceutical composition of claim 1, wherein the gelation temperature of the pharmaceutical composition is between about 15° C. and about 30° C., between about 20° C. and about 28° C., or between about 24° C. and about 26° C.

12. The pharmaceutical composition of claim 1, wherein the gelation temperature of the pharmaceutical composition is about 15° C., about 20° C., about 24° C., about 26° C., about 28° C., about 30° C., or about 32° C.

13. The pharmaceutical composition of claim 1, wherein the carboxylic acid containing compound is in a concentration between about 2 wt % and about 20 wt % relative to the pharmaceutical composition.

14. The pharmaceutical composition of claim 1, wherein the carboxylic acid containing compound is in a concentration of at least 4 wt %, at least 8 wt %, at least 12 wt %, at least 16 wt %, or at least 20 wt % relative to the pharmaceutical composition.

15. The pharmaceutical composition of claim 1, wherein the carboxylic acid containing compound is in a concentration of about 4 wt %, about 8 wt %, about 12 wt %, about 16 wt %, or about 20 wt % relative to the pharmaceutical composition.

16. A method of expanding a population of cochlear cells in a cochlear tissue comprising a parent population of cells, the method comprising contacting the cochlear tissue with the pharmaceutical composition of claim 1.

17. A method of facilitating generation of tissue cells, the method comprising administering or causing to be administered to a stem cell population the pharmaceutical composition of claim 1.

18. A method of treating a subject who has, or is at risk of developing hearing loss, the method comprising administering to the subject the pharmaceutical composition of claim 1.

* * * * *